United States Patent
Bluestone et al.

(10) Patent No.: US 12,421,302 B2
(45) Date of Patent: Sep. 23, 2025

(54) CAR-T CELLS AND AUTOIMMUNE DISEASES

(71) Applicant: THE REGENTS OF THE UNIVERSITY OF CALIFORNIA, Oakland, CA (US)

(72) Inventors: Jeffrey A. Bluestone, San Francisco, CA (US); Caroline Raffin, San Francisco, CA (US)

(73) Assignee: The Regents of the University of California, Oakland, CA (US)

(*) Notice: Subject to any disclaimer, the term of this patent is extended or adjusted under 35 U.S.C. 154(b) by 1062 days.

(21) Appl. No.: 16/968,794

(22) PCT Filed: Feb. 11, 2019

(86) PCT No.: PCT/US2019/017532
§ 371 (c)(1),
(2) Date: Aug. 10, 2020

(87) PCT Pub. No.: WO2019/157461
PCT Pub. Date: Aug. 15, 2019

(65) Prior Publication Data
US 2020/0399355 A1    Dec. 24, 2020

Related U.S. Application Data

(60) Provisional application No. 62/629,103, filed on Feb. 11, 2018.

(51) Int. Cl.
| | | |
|---|---|---|
| *C07K 16/18* | (2006.01) | |
| *A61K 38/17* | (2006.01) | |
| *A61K 39/395* | (2006.01) | |
| *A61K 40/11* | (2025.01) | |
| *A61K 40/22* | (2025.01) | |
| *A61K 40/31* | (2025.01) | |
| *A61K 40/41* | (2025.01) | |
| *A61P 19/02* | (2006.01) | |
| *A61P 37/06* | (2006.01) | |
| *C07K 14/705* | (2006.01) | |
| *C07K 14/725* | (2006.01) | |
| *C12N 5/0783* | (2010.01) | |
| *A61K 35/12* | (2015.01) | |

(52) U.S. Cl.
CPC .......... *C07K 16/18* (2013.01); *A61K 38/177* (2013.01); *A61K 38/1774* (2013.01); *A61K 39/3955* (2013.01); *A61K 40/11* (2025.01); *A61K 40/22* (2025.01); *A61K 40/31* (2025.01); *A61K 40/416* (2025.01); *A61P 19/02* (2018.01); *A61P 37/06* (2018.01); *C07K 14/7051* (2013.01); *C07K 14/70521* (2013.01); *C07K 14/70578* (2013.01); *C12N 5/0636* (2013.01); *C12N 5/0637* (2013.01); *A61K 2035/124* (2013.01); *C07K 2317/569* (2013.01); *C07K 2317/622* (2013.01); *C07K 2317/76* (2013.01); *C07K 2317/92* (2013.01); *C07K 2319/02* (2013.01); *C07K 2319/03* (2013.01); *C07K 2319/30* (2013.01); *C07K 2319/33* (2013.01); *C12N 2510/00* (2013.01)

(58) Field of Classification Search
None
See application file for complete search history.

(56) References Cited

U.S. PATENT DOCUMENTS

2016/0159922 A1  6/2016  Klareskog et al.
2016/0333422 A1  11/2016  Feldman et al.

FOREIGN PATENT DOCUMENTS

| WO | WO-2016/033331 | 3/2016 | |
|---|---|---|---|
| WO | WO-2017/079694 | 5/2017 | |
| WO | WO-2017100428 A1 * | 6/2017 | ............. A61K 35/17 |

OTHER PUBLICATIONS

Minchin, Steve, and Julia Lodge. "Understanding biochemistry: structure and function of nucleic acids." Essays in biochemistry vol. 63,4 (2019): 433-456. doi: 10.1042/EBC20180038 (Year: 2019).*
Miko, I. & LeJeune, L., eds. Essentials of Genetics. Cambridge, MA: NPG Education, 2009 (Year: 2009).*
Stryer, Biochemistry 4th, WH Freeman, New York. 1995 (Year: 1995).*
Wood, L et al. "Vimentin cDNA clones covering the complete intermediate-filament protein are found in an EHS tumor cDNA library." Gene vol. 76,1 (1989): 171-5. doi:10.1016/0378-1119(89)90020-6 (Year: 1989).*
Ferrari, S et al. "Coding sequence and growth regulation of the human vimentin gene." Molecular and cellular biology vol. 6, 11 ( 1986): 3614-20. doi:10.1128/mcb.6.11.3614-3620.1986 (Year: 1986).*
Janeway, Charles A. "Immunobiology: The Immune System in Health and Disease." 2001 (Year: 2001).*
Haque, M. et al. (Aug. 8, 2014). "Utilizing regulatory T cells against rheumatoid arthritis," *Front Oncol* 4:209.
James, E.A. et al. (Jul. 2014). "Citrulline-specific Th1 cells are increased in rheumatoid arthritis and their frequency is influenced by disease duration and therapy," *Arthritis Rheumatology* 66(7):1712-1722.
Pozsgay, J. et al. (Sep. 2017, e-published Jul. 13, 2017). "Antigen-specific immunotherapies in rheumatic diseases," *Nature Reviews Rheumatology* 13(9):525-537.

(Continued)

*Primary Examiner* — Zachariah Lucas
*Assistant Examiner* — Lia E Taylor
(74) *Attorney, Agent, or Firm* — Mintz, Levin, Cohn, Ferris, Glovsky and Popeo, P.C.

(57) ABSTRACT

Chimeric antigen receptor (CAR)-expressing Tregs specifically target an antigen present in the joint of RA patients to induce a localized and effective immunosuppressive response.

20 Claims, 25 Drawing Sheets
Specification includes a Sequence Listing.

(56) References Cited

OTHER PUBLICATIONS

Burmester, G. et al. (Jun. 8, 2017). "Novel treatment strategies in rheumatoid arthritis," *The Lancet* 389(10086):2338-2348.
Extended European Search Report mailed on Oct. 12, 2021, for EP Patent Application No. 19751596.8, 11 pages.
Feitsma, A.L. et al. (Jan. 2010). "Identification of citrullinated vimentin peptides as T cell epitopes in HLA-DR4-positive patients with rheumatoid arthritis," *Arthritis Rheum* 62(1):117-125.
Oldham, R.A.A. et al. (Aug. 2017, e-published Jun. 16, 2017). "Practical considerations for chimeric antigen receptor design and delivery," *Expert Opin Biol Ther* 17(8):961-978.
Posey, A.D. et al. (Jun. 21, 2016). "Engineered CAR T Cells Targeting the Cancer-Associated Tn-Glycoform of the Membrane Mucin MUC1 Control Adenocarcinoma," *Immunity* 44(6):1444-1454.
Raffin, C. et al. (May 1, 2016). "Development of citrullinated-vimentin-specific CAR for targeting Tregs to treat autoimmune rheumatoid arthritis," *The Journal of Immunology* 196(1 Supplement) 210.19, 4 pages.
Raffin, C. et al. (May 1, 2018). "Development of citrullinated-vimentin-specific CAR for targeting Tregs to treat autoimmune rheumatoid arthritis," *The Journal of Immunology* 200(1 Supplement) 176.17, 4 pages.
Shirasu, N. et al. (Jul. 2010). "Construction and molecular characterization of human chimeric T-cell antigen receptors specific for carcinoembryonic antigen," *Anticancer Res* 30(7):2731-2738.
Van Steendam, K. et al. (2010, e-published Jul. 7, 2010). "Citrullinated vimentin as an important antigen in immune complexes from synovial fluid of rheumatoid arthritis patients with antibodies against citrullinated proteins," *Arthritis Res Ther* 12(4):R132.
Wang, Y. et al. (Dec. 22, 2017). "New Chimeric Antigen Receptor Design for Solid Tumors," *Front Immunol* 8:1934.
International Search Report mailed on Jul. 12, 2019, for PCT Application No. PCT/US2019/017532, filed Feb. 11, 2019, 5 pages.
Written Opinion mailed on Jul. 12, 2019, for PCT Application No. PCT/US2019/017532, filed Feb. 11, 2019, 7 pages.

\* cited by examiner

CV.28z CAR Tregs
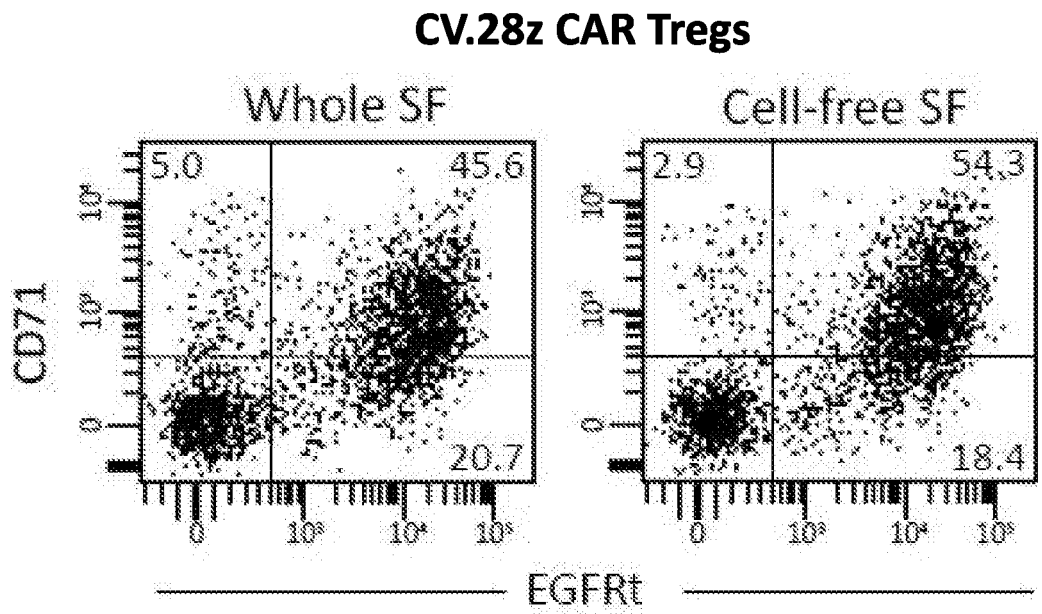
FIG. 22A
FIG. 22B
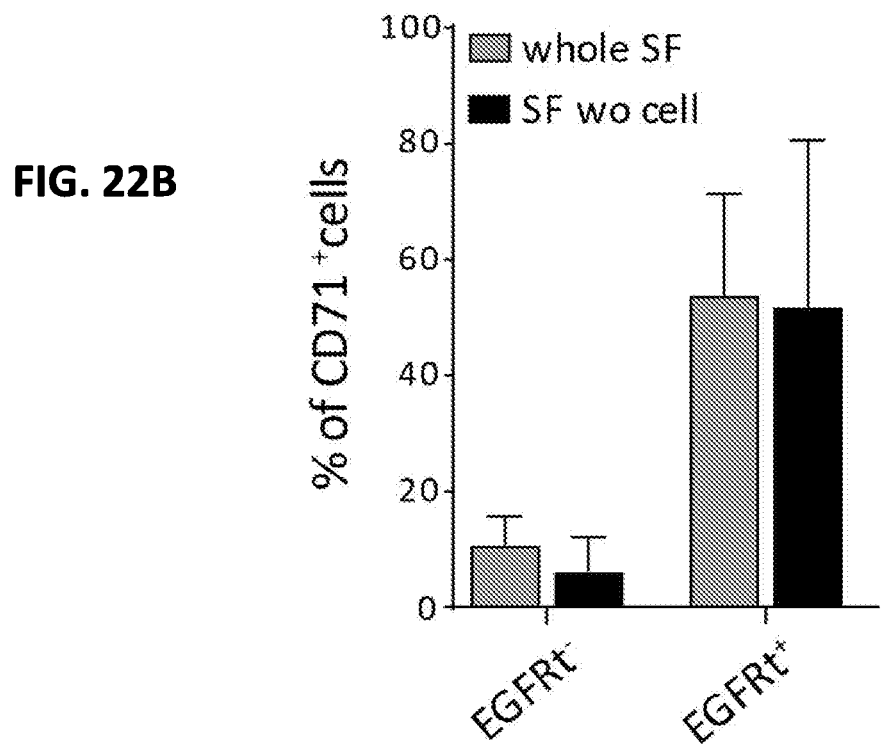

CAR-T CELLS AND AUTOIMMUNE DISEASES

CROSS-REFERENCE TO RELATED APPLICATIONS

This application is a National Stage Application filed under 35 U.S.C. § 371, of International Patent Application No PCT/US2019/017532, filed on Feb. 11, 2019, which claims the benefit of and priority to U.S. Provisional Application No. 62/629,103, filed on Feb. 11, 2018. The entire contents of which are incorporated herein by reference in their entirety.

INCORPORATION BY REFERENCE OF SEQUENCE LISTING

The contents of the sequence listing text file named "048536-613N01USWO_Sequence_Listing_txt", which was created on Mar. 20, 2019 and is 47,028 bytes in size, are incorporated herein by reference in its entirety.

FIELD OF THE INVENTION

Embodiments of the invention are directed to chimeric antigen receptors (CAR), chimeric antigen receptor T cells (CAR-T) and use in treatment of diseases, such as autoimmune diseases.

BACKGROUND

Traditionally, antigen-specific T-cells have been generated by selective expansion of peripheral blood T-cells natively specific for the target antigen. However, it is difficult and quite often impossible to select and expand large numbers of T-cells specific for most cancer and autoantigens. Gene-therapy with integrating vectors affords a solution to this problem as transgenic expression of Chimeric Antigen Receptor (CAR) allows generation of large numbers of T-cells specific to any surface antigen by ex vivo viral vector transduction of a bulk population of peripheral blood T-cells.

SUMMARY

Embodiments of the invention are directed, in part, to chimeric antigen receptors (CAR) which specifically recognize antigens associated with autoimmune diseases. In particular, the CAR are specific for post-translationally modified antigens. The CARs are transduced into T cells, such as, regulatory T cells, which suppress the autoimmune response or cytotoxic T cells.

Accordingly, in one aspect of the present invention there is provided a chimeric antigen receptor (CAR) comprising an antigen specific binding domain, a hinge domain, a transmembrane domain, co-stimulatory domain, and a CD3ζ signaling domain, wherein the antigen specific binding domain specifically binds to modified polypeptides or peptides thereof, including, citrullinated proteins such as citrullinated extracellular matrix proteins and citrullinated cell-surface proteins.

In a second aspect of the present invention there is provided a chimeric antigen receptor (CAR) comprising an antigen specific binding domain, a hinge domain, a transmembrane domain, co-stimulatory domain, and a CD3ζ signaling domain, wherein the antigen specific binding domain specifically binds to citrullinated-vimentin (CV) polypeptides or peptides thereof.

In a third aspect, the present invention provides an isolated T cell that is modified to express: a chimeric antigen receptor (CAR) comprising an antigen binding domain linked to at least one co-stimulatory domain and CD3ζ signaling domain, wherein the antigen binding domain comprises a single chain variable fragment (scFv) which specifically binds to citrullinated-vimentin (CV). In certain embodiments, the antigen binding domain comprises an antibody, antibody fragment, camelid nanobody or aptamer.

In certain embodiments, the hinge domain is encoded by a nucleic acid sequence having at least 50% sequence identity to SEQ ID NO: 8; the transmembrane domain is encoded by a nucleic acid sequence having at least 50% sequence identity to SEQ ID NO: 9; the CD3ζ signaling domain is encoded by a nucleic acid sequence having at least 50% sequence identity to SEQ ID NO: 10; and/or; the CD28 co-stimulatory domain is encoded by a nucleic acid sequence having at least 50% sequence identity to SEQ ID NO: 11.

In certain embodiments, the hinge domain is encoded by a nucleic acid sequence having at least 75% sequence identity to SEQ ID NO: 8; the transmembrane domain is encoded by a nucleic acid sequence having at least 75% sequence identity to SEQ ID NO: 9; the CD3ζ signaling domain is encoded by a nucleic acid sequence having at least 75% sequence identity to SEQ ID NO: 10; and/or; the CD28 co-stimulatory domain is encoded by a nucleic acid sequence having at least 75% sequence identity to SEQ ID NO: 11.

In certain embodiments, the hinge domain is encoded by a nucleic acid sequence having at least 95% sequence identity to SEQ ID NO: 8; the transmembrane domain is encoded by a nucleic acid sequence having at least 95% sequence identity to SEQ ID NO: 9; the CD3ζ signaling domain is encoded by a nucleic acid sequence having at least 95% sequence identity to SEQ ID NO: 10; and/or; the CD28 co-stimulatory domain is encoded by a nucleic acid sequence having at least 95% sequence identity to SEQ ID NO: 11.

In certain embodiments, the hinge domain is encoded by the nucleic acid sequence of SEQ ID NO: 8; the transmembrane domain is encoded by the nucleic acid sequence of SEQ ID NO: 9; the CD3ζ signaling domain is encoded by the nucleic acid sequence of SEQ ID NO: 10; and/or; the CD28 co-stimulatory domain is encoded by the nucleic acid sequence of SEQ ID NO: 11.

In certain embodiments, the hinge domain is encoded by a nucleic acid sequence having at least 50% sequence identity to SEQ ID NO: 8; the transmembrane domain is encoded by a nucleic acid sequence having at least 50% sequence identity to SEQ ID NO: 9; the CD3ζ signaling domain is encoded by a nucleic acid sequence having at least 50% sequence identity to SEQ ID NO: 10; and/or; the 41BB co-stimulatory domain is encoded by a nucleic acid sequence having at least 50% sequence identity to SEQ ID NO: 12.

In certain embodiments, the hinge domain is encoded by a nucleic acid sequence having at least 75% sequence identity to SEQ ID NO: 8; the transmembrane domain is encoded by a nucleic acid sequence having at least 75% sequence identity to SEQ ID NO: 9; the CD3ζ signaling domain is encoded by a nucleic acid sequence having at least 75% sequence identity to SEQ ID NO: 10; and/or; the 41BB co-stimulatory domain is encoded by a nucleic acid sequence having at least 75% sequence identity to SEQ ID NO: 12.

In certain embodiments, the hinge domain is encoded by a nucleic acid sequence having at least 95% sequence identity to SEQ ID NO: 8; the transmembrane domain is encoded by a nucleic acid sequence having at least 95% sequence identity to SEQ ID NO: 9; the CD3ζ signaling domain is encoded by a nucleic acid sequence having at least 95% sequence identity to SEQ ID NO: 10; and/or; the 41BB co-stimulatory domain is encoded by a nucleic acid sequence having at least 95% sequence identity to SEQ ID NO: 12.

In certain embodiments, the hinge domain is encoded by the nucleic acid sequence of SEQ ID NO: 8; the transmembrane domain is encoded by the nucleic acid sequence of SEQ ID NO: 9; the CD3ζ signaling domain is encoded by the nucleic acid sequence of SEQ ID NO: 10; and/or; the 41BB co-stimulatory domain is encoded by the nucleic acid sequence of SEQ ID NO: 12.

In certain embodiments, the CV-CAR specifically binds to a CV peptide having at least a 50% sequence identity to SEQ ID NO: 3 or 4. In certain embodiments, the CV-CAR specifically binds to a CV peptide having at least a 75% sequence identity to SEQ ID NO: 3 or 4.

In certain embodiments, the CV-CAR specifically binds to a CV peptide having at least a 95% sequence identity to SEQ ID NO: 3 or 4.

In certain embodiments, the CV-CAR specifically binds to a CV peptide comprising SEQ ID NO: 3 or 4.

In certain embodiments, the CV-CAR specifically binds to a CV peptide having at least a 50% sequence identity to SEQ ID NO: 21 or 22. In certain embodiments, the CV-CAR specifically binds to a CV peptide having at least a 75% sequence identity to SEQ ID NO: 21 or 22.

In certain embodiments, the CV-CAR specifically binds to a CV peptide having at least a 95% sequence identity to SEQ ID NO: 21 or 22.

In certain embodiments, the CV-CAR specifically binds to a CV peptide comprising SEQ ID NO: 21 or 22.

In a fourth aspect, the present invention provides an isolated T cell that is modified to express: a chimeric antigen receptor (CAR) comprising an antigen binding domain linked to at least one co-stimulatory domain and a CD3ζ signaling domain, wherein the antigen binding domain comprises a single chain variable fragment (scFv) which specifically binds to citrullinated-vimentin (CV). In certain embodiments, the co-stimulatory domain comprises a CD28 or a 41BB polypeptide. In certain embodiments, the CAR comprises a hinge domain encoded by a nucleic acid sequence having at least 50% sequence identity to SEQ ID NO: 8; the CAR comprises a transmembrane domain encoded by a nucleic acid sequence having at least 50% sequence identity to SEQ ID NO: 9; the CD3ζ signaling domain is encoded by a nucleic acid sequence having at least 50% sequence identity to SEQ ID NO: 10; and/or; the CD28 co-stimulatory domain is encoded by a nucleic acid sequence having at least 50% sequence identity to SEQ ID NO: 11. In certain embodiments, the CAR comprises a hinge domain encoded by a nucleic acid sequence having at least 75% sequence identity to SEQ ID NO: 8; the CAR comprises a transmembrane domain encoded by a nucleic acid sequence having at least 75% sequence identity to SEQ ID NO: 9; the CD3ζ signaling domain is encoded by a nucleic acid sequence having at least 75% sequence identity to SEQ ID NO: 10; and/or; the CD28 co-stimulatory domain is encoded by a nucleic acid sequence having at least 75% sequence identity to SEQ ID NO: 11. In certain embodiments, the CAR comprises a hinge domain encoded by a nucleic acid sequence having at least 95% sequence identity to SEQ ID NO: 8; the CAR comprises a transmembrane domain encoded by a nucleic acid sequence having at least 95% sequence identity to SEQ ID NO: 9; the CD3ζ signaling domain is encoded by a nucleic acid sequence having at least 95% sequence identity to SEQ ID NO: 10; and/or; the CD28 co-stimulatory domain is encoded by a nucleic acid sequence having at least 95% sequence identity to SEQ ID NO: 11. In certain embodiments, the CAR comprises a hinge domain encoded by the nucleic acid sequence of SEQ ID NO: 8; the CAR comprises a transmembrane domain encoded by the nucleic acid sequence of SEQ ID NO: 9; the CD3ζ signaling domain is encoded by the nucleic acid sequence of SEQ ID NO: 10; and/or; the CD28 co-stimulatory domain is encoded by the nucleic acid sequence of SEQ ID NO: 11. In certain embodiments, the CAR comprises a hinge domain encoded by a nucleic acid sequence having at least 50% sequence identity to SEQ ID NO: 8; the CAR comprises a transmembrane domain encoded by a nucleic acid sequence having at least 50% sequence identity to SEQ ID NO: 9; the CD3ζ signaling domain is encoded by a nucleic acid sequence having at least 50% sequence identity to SEQ ID NO: 10; and/or; the 41BB co-stimulatory domain is encoded by a nucleic acid sequence having at least 50% sequence identity to SEQ ID NO: 12. In certain embodiments, the CAR comprises a hinge domain encoded by a nucleic acid sequence having at least 75% sequence identity to SEQ ID NO: 8; the CAR comprises a transmembrane domain encoded by a nucleic acid sequence having at least 75% sequence identity to SEQ ID NO: 9; the CD3ζ signaling domain is encoded by a nucleic acid sequence having at least 75% sequence identity to SEQ ID NO: 10; and/or; the 41BB co-stimulatory domain is encoded by a nucleic acid sequence having at least 75% sequence identity to SEQ ID NO: 12. In certain embodiments, the CAR comprises a hinge domain encoded by a nucleic acid sequence having at least 95% sequence identity to SEQ ID NO: 8; the CAR comprises a transmembrane domain encoded by a nucleic acid sequence having at least 95% sequence identity to SEQ ID NO: 9; the CD3ζ signaling domain is encoded by a nucleic acid sequence having at least 95% sequence identity to SEQ ID NO: 10; and/or; the 41BB co-stimulatory domain is encoded by a nucleic acid sequence having at least 95% sequence identity to SEQ ID NO: 12. In certain embodiments, the CAR comprises a hinge domain encoded by the nucleic acid sequence of SEQ ID NO: 8; the CAR comprises a transmembrane domain encoded by the nucleic acid sequence of SEQ ID NO: 9; the CD3ζ signaling domain is encoded by the nucleic acid sequence of SEQ ID NO: 10; and/or; the 41BB co-stimulatory domain is encoded by the nucleic acid sequence of SEQ ID NO: 12.

In certain embodiments, the T cell is a mammalian regulatory T cell (Treg). In certain embodiments, the Treg cell is $CD4^+CD25^+CD127^-$, $FOXP3^+$.

In certain embodiments, an expression vector encodes a chimeric antigen receptor (CAR).

In a fifth aspect, the present invention provides a pharmaceutical composition comprising a chimeric antigen receptor (CAR), an expression vector encoding a chimeric antigen receptor (CAR) or an isolated T cell that is modified to express a chimeric antigen receptor (CAR).

In a sixth aspect, the present invention provides method of treating a subject diagnosed with rheumatoid arthritis, comprising administering an isolated T cell that is modified to express a chimeric antigen receptor (CAR), wherein the CAR specifically binds to a citrullinated-vimentin (CV) antigen. In certain aspects, anti-inflammatory agents and/or therapeutic agents are also administered to the subject. In certain embodiments, a method of treating a subject diagnosed with rheumatoid arthritis, comprises isolating T lymphocytes from a biological sample obtained from the subject; separating CD4+ T regulatory Cells (Treg) from conventional T cells (Tconv), wherein the Treg cells are CD4+CD25+CD127− and the Tconv are CD4+CD25−CD127+; transducing the Treg cells with an expression vector encoding a chimeric antigen receptor (CAR) which specifically binds to a citrullinated-vimentin (CV) antigen; expanding the transduced Treg with anti-CD3/CD28 beads at least once ex vivo to obtain expanded Treg cells specific for the CV antigen; and reinfusing the Treg into the subject, thereby treating the subject. In certain embodiments, the CAR comprises an antigen binding domain linked to at least one co-stimulatory domain and a CD3ζ signaling domain, wherein the antigen binding domain comprises a single chain variable fragment (scFv) which specifically binds to citrullinated-vimentin (CV). In certain embodiments, the co-stimulatory domain comprises a CD28 or a 41BB polypeptide. In certain embodiments, the CAR comprises a hinge domain encoded by a nucleic acid sequence having at least 50% sequence identity to SEQ ID NO: 8; the CAR comprises a transmembrane domain encoded by a nucleic acid sequence having at least 50% sequence identity to SEQ ID NO: 9; the CD3ζ signaling domain is encoded by a nucleic acid sequence having at least 50% sequence identity to SEQ ID NO: 10; and/or; the CD28 co-stimulatory domain is encoded by a nucleic acid sequence having at least 50% sequence identity to SEQ ID NO: 11. In certain embodiments, the CAR comprises a hinge domain encoded by a nucleic acid sequence having at least 50% sequence identity to SEQ ID NO: 8; the CAR comprises a transmembrane domain encoded by a nucleic acid sequence having at least 50% sequence identity to SEQ ID NO: 9; the CD3ζ signaling domain is encoded by a nucleic acid sequence having at least 50% sequence identity to SEQ ID NO: 10; and/or; the 41BB co-stimulatory domain is encoded by a nucleic acid sequence having at least 50% sequence identity to SEQ ID NO: 12.

In a seventh aspect, the present invention there is provided chimeric antigen receptors (CARs) wherein the CARs are transduced into various types of cell including T cells, such as regulatory T cells (Treg), cytotoxic T cells (CTL), conventional T cells (Tconv); other types of cells of the immune system, such as natural killer cells (NK); stem cells, cell lines and the like. The CARs comprise antigen binding domains generated to specific disease target antigens, such as extracellular antigens, cell-surface antigens, viral antigens, post-translationally modified antigens and the like.

Other aspects are described infra.

DEFINITIONS

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value or range. Alternatively, particularly with respect to biological systems or processes, the term can mean within an order of magnitude within 5-fold, and also within 2-fold, of a value. Where particular values are described in the application and claims, unless otherwise stated the term "about" meaning within an acceptable error range for the particular value should be assumed.

As used herein, the term "affinity" is meant as a measure of binding strength. Without being bound to theory, affinity depends on the closeness of stereochemical fit between antibody combining sites and antigen determinants, on the size of the area of contact between them, and on the distribution of charged and hydrophobic groups. Affinity also includes the term "avidity," which refers to the strength of the antigen-antibody bond after formation of reversible complexes. Methods for calculating the affinity of an antibody for an antigen are known in the art, including use of binding experiments to calculate affinity. Antibody activity in functional assays (e.g., flow cytometry assay) is also reflective of antibody affinity. Antibodies and affinities can be phenotypically characterized and compared using functional assays (e.g., flow cytometry assay).

As used herein, the term "agent" is meant to encompass any molecule, chemical entity, composition, drug, therapeutic agent, chemotherapeutic agent, or biological agent capable of preventing, ameliorating, or treating a disease or other medical condition. The term includes small molecule compounds, antisense oligonucleotides, siRNA reagents, antibodies, antibody fragments bearing epitope recognition sites, such as Fab, Fab', F(ab')₂ fragments, Fv fragments, single chain antibodies, antibody mimetics (such as DARPins, affibody molecules, affilins, affitins, anticalins, avimers, fynomers, Kunitz domain peptides and monobodies), peptoids, aptamers; enzymes, peptides organic or inorganic molecules, natural or synthetic compounds and the like. An agent can be assayed in accordance with the methods of the invention at any stage during clinical trials, during pre-trial testing, or following FDA-approval.

By "ameliorate" is meant decrease, suppress, attenuate, diminish, arrest, or stabilize the development or progression of a disease.

As used herein, the term "antibody" means not only intact antibody molecules, but also fragments of antibody molecules that retain immunogen-binding ability. Such fragments are also well known in the art and are regularly employed both in vitro and in vivo. Accordingly, as used herein, the term "antibody" means not only intact immunoglobulin molecules but also the well-known active fragments F(ab')₂, and Fab. F(ab')₂, and Fab fragments that lack the Fc fragment of intact antibody, clear more rapidly from the circulation, and may have less non-specific tissue binding of an intact antibody (Wahl et al., *J. Nucl. Med.* 24:316-325 (1983). The antibodies of the invention comprise whole native antibodies, bispecific antibodies; chimeric antibodies; Fab, Fab', single chain V region fragments (scFv), fusion polypeptides, and unconventional antibodies.

As used in this specification and the appended claims, the term "or" is generally employed in its sense including "and/or" unless the content clearly dictates otherwise.

The term "chimeric antigen receptor" or "CAR" as used herein refers to an antigen-binding domain that is fused to an intracellular signaling domain capable of activating or stimulating an immune cell, and in certain embodiments, the CAR also comprises a transmembrane domain. In certain embodiments the CAR's extracellular antigen-binding domain is composed of a single chain variable fragment (scFv) derived from fusing the variable heavy and light regions of a murine or humanized monoclonal antibody. Alternatively, scFvs may be used that are derived from Fab's (instead of from an antibody, e.g., obtained from Fab libraries). In various embodiments, the scFv is fused to the transmembrane domain and then to the intracellular signaling domain. "First-generation" CARs include those that solely provide CD3ζ signals upon antigen binding, "Second-generation" CARs include those that provide both co-stimulation (e.g., CD28 or CD137) and activation (CD3ζ). "Third-generation" CARs include those that provide multiple co-stimulation (e.g. CD28 and CD137) and activation (CD3ζ). A fourth generation of CARs have been described, CAR T cells redirected for cytokine killing (TRUCKS) where the vector containing the CAR construct possesses a cytokine cassette. When the CAR is ligated, the CAR T cell deposits a pro-inflammatory cytokine into the tumor lesion. A CAR-T cell is a T cell that expresses a chimeric antigen receptor. The phrase "chimeric antigen receptor (CAR)," as used herein and generally used in the art, refers to a recombinant fusion protein that has an antigen-specific extracellular domain coupled to an intracellular domain that directs the cell to perform a specialized function upon binding of an antigen to the extracellular domain. The terms "artificial T-cell receptor," "chimeric T-cell receptor," and "chimeric immunoreceptor" may each be used interchangeably herein with the term "chimeric antigen receptor."

As used herein, the terms "comprising," "comprise" or "comprised," and variations thereof, in reference to defined or described elements of an item, composition, apparatus, method, process, system, etc. are meant to be inclusive or open ended, permitting additional elements, thereby indicating that the defined or described item, composition, apparatus, method, process, system, etc. includes those specified elements—or, as appropriate, equivalents thereof—and that other elements can be included and still fall within the scope/definition of the defined item, composition, apparatus, method, process, system, etc.

"Diagnostic" or "diagnosed" means identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

A "disease" is a state of health of an animal wherein the animal cannot maintain homeostasis, and wherein if the disease is not ameliorated then the animal's health continues to deteriorate. Examples of diseases include autoimmune diseases such as, rheumatoid arthritis (RA), inflammatory bowel disease (IBD), Crohn's disease (CD), ankylosing spondylitis (AS), and the like.

The term "hinge" or "hinge region" refers to a flexible connector region, e.g. natural or synthetic polypeptides, or any other type of molecule, providing structural flexibility and spacing to flanking polypeptide regions.

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses.

The term "linker", also referred to as a "spacer" or "spacer domain" as used herein, refers to an amino acid or sequence of amino acids that that is optionally located between two amino acid sequences in a fusion protein of the invention.

"Parenteral" administration of an immunogenic composition includes, e.g., subcutaneous (s.c.), intravenous (i.v.), intramuscular (i.m.), or intrasternal injection, or infusion techniques.

The terms "patient" or "individual" or "subject" are used interchangeably herein, and refers to a mammalian subject to be treated, with human patients being preferred. In some cases, the methods of the invention find use in experimental animals, in veterinary application, and in the development of animal models for disease, including, but not limited to, rodents including mice, rats, and hamsters, and primates.

As used herein, the term "single-chain variable fragment" or "scFv" is a fusion protein of the variable regions of the heavy (VH) and light chains (VL) of an immunoglobulin. The heavy (VH) and light chains (VL) are either joined directly or joined by a peptide-encoding linker (e.g., 10, 15, 20, 25 amino acids), which connects the N-terminus of the VH with the C-terminus of the VL, or the C-terminus of the VH with the N-terminus of the VL. The linker is usually rich in glycine for flexibility, as well as serine or threonine for solubility. Despite removal of the constant regions and the introduction of a linker, scFv proteins retain the specificity of the original immunoglobulin. Single chain Fv polypeptide antibodies can be expressed from a nucleic acid including VH- and VL-encoding sequences as described by Huston, et al. (*Proc. Nat. Acad. Sci. USA*, 85:5879-5883, 1988). See, also, U.S. Pat. Nos. 5,091,513, 5,132,405 and 4,956,778; and U.S. Patent Publication Nos. 20050196754 and 20050196754. Antagonistic scFvs having inhibitory activity have been described (see, e.g., Zhao et al., *Hyrbidoma* (Larchmt) 2008 27(6):455-51; Peter et al., *J Cachexia Sarcopenia Muscle* 2012 Aug. 12; Shieh et al., *J Imunol* 2009 183(4):2277-85; Giomarelli et al., *Thromb Haemost* 2007 97(6):955-63; Fife et al., *J Clin Invst* 2006 116(8): 2252-61; Brocks et al., *Immunotechnology* 1997 3(3): 173-84; Moosmayer et al., *Ther Immunol* 1995 2(10:31-40). Agonistic scFvs having stimulatory activity have been described (see, e.g., Peter et al., *J Bioi Chem* 2003 25278 (38):36740-7; Xie et al., *Nat Biotech* 1997 15(8):768-71; Ledbetter et al., *Crit Rev Immunol* 1997 17(5-6):427-55; Ho et al., *BioChim Biophys Acta* 2003 1638(3):257-66).

As used herein, the terms "treat," "treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

A "vector" is a composition of matter which comprises an isolated nucleic acid and which can be used to deliver the isolated nucleic acid to the interior of a cell. Examples of vectors include but are not limited to, linear polynucleotides, polynucleotides associated with ionic or amphiphilic compounds, plasmids, and viruses. Thus, the term "vector" includes an autonomously replicating plasmid or a virus. The term is also construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

All genes, gene names, and gene products disclosed herein are intended to correspond to homologs from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context in which it appears clearly indicates. Thus, for example, for the genes or gene products disclosed herein, which in some embodiments relate to mammalian nucleic acid and amino acid sequences, are intended to encompass homologous and/or orthologous genes and gene products from other animals including, but not limited to other mammals, fish, amphibians, reptiles, and birds. In preferred embodiments, the genes, nucleic acid sequences, amino acid sequences, peptides, polypeptides and proteins are human. The term "gene" is also intended to include variants.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, Molecular Cloning (Cold Spring Harbor Laboratory Press, Cold Spring Harbor, N.Y.); Sambrook et al., 1989, Molecular Cloning, 2nd Ed. (Cold Spring Harbor Laboratory Press, Cold Spring Harbor, N.Y.); Sambrook and Russell, 2001, Molecular Cloning, 3rd Ed. (Cold Spring Harbor Laboratory Press, Cold Spring Harbor, N.Y.); Ausubel et al., 1992), Current Protocols in Molecular Biology (John Wiley & Sons, including periodic updates); Glover, 1985, DNA Cloning (IRL Press, Oxford); Anand, 1992; Guthrie and Fink, 1991; Harlow and Lane, 1988, Antibodies, (Cold Spring Harbor Laboratory Press, Cold Spring Harbor, N.Y.); Jakoby and Pastan, 1979; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Riott, Essential Immunology, 6th Edition, Blackwell Scientific Publications, Oxford, 1988; Hogan et al., Manipulating the Mouse Embryo, (Cold Spring Harbor Laboratory Press, Cold Spring Harbor, N.Y., 1986); Westerfield, M., The zebrafish book. A guide for the laboratory use of zebrafish (*Danio rerio*), (4th Ed., Univ. of Oregon Press, Eugene, 2000).

BRIEF DESCRIPTION OF THE DRAWINGS

FIG. 10A. Analysis of expression of the activation markers CD71 and CD25 at day 3 after re-stimulation. FIG. 10B. Analysis of cell expansion at day 5 after re-stimulation.

FIG. 12A. Assessment of surface expression of the reporter EGFRt in Tregs and Tconv by flow cytometry at day 4 after transduction with the different CAR constructs. Summary of the data for all donors (n=4) FIG. 12B. Representative dot plots of surface expression of the reporter EGFRt in Tregs and Tconv by flow cytometry at day 4 after transduction with the different CAR constructs. FIG. 12C. Schematic representation of a biotinylated-CV peptide (pep)/SA-FITC complex. FIG. 12D. Assessment of surface expression of the reporter EGFRt and CV-CAR in Tregs. The Treg cells were stained for the CV-CAR using a biotinylated-CV-peptide/Streptavidin tetramer conjugated with FITC (CVpep-SA-FITC) and EGFRt antibody at day 5 after transduction. Dot plots are representative of 4 independent experiments;

FIG. 14A. Assessment of cell clustering at day 1. FIG. 14B. Assessment of expression of the activation markers CD71 and CD25 at day 3. FIG. 14C. Assessment of the expansion fold of the different CAR Treg populations in all of the conditions measured at day 5 after re-stimulation;

FIG. 15A. Assessment of the cells by flow cytometry for CD25 and CD127 surface expression, at day 18. FIG. 15B. Assessment of the cells by flow cytometry for FOXP3 and Helios intranuclear expression, at day 18. FIG. 15C. Assessment of the cytokine production profile of the expanded Tregs after the cells were stimulated with PMA/ionomycin for 4 hours, the last 2 hours in presence of brefeldin A. Cells were then fixed and stained with antibodies targeting IFN-g, IL-2, IL-10 and IL-17;

FIG. 16A. Assessment of the expression of CD71 and EGFRt (dot plots). Numbers in red (in the upper right corner of each graph) represent the percentage of CD71+ cells among the EGFRt+ fraction. FIG. 16B. Percentages of CD71+ cells among the EGFRt− and EGFRt+ fractions in the different CAR Treg populations;

FIG. 17A. Assessment of expression of CAR and EGFRt at the surface of Non-transduced Tregs, CV/CD28t CAR' Tregs, and CV/41BBζ CAR$^+$ Tregs. FIG. 17B. Percentage of CAR$^+$ cells in various experiments;

FIG. 18A. Expression of CD71 and EGFRt in CV.28ζ-CAR Treg population after co-culture in various conditions. FIG. 18B. Representative dot plots showing the expression of CD71 against EGFRt in 19.28ζ-CAR Tregs and CV.28ζ-CAR Tregs in presence of SF from Gout negative control patient or RA SF. FIG. 18C. Summary of the percentages of CD71$^+$ cells among the EGFRt$^-$ and EGFRt$^+$ fractions in the different CAR Treg populations after co-culture in presence of SF from RA patients n=4).

FIG. 20A. Three days after transduction, GFP expression in SKNBE2C cells was assessed by flow cytometry. FIG. 20B. Presence of citrullinated vimentin in wild type (WT) and PAD2-GFP transduced SKNBE2C cells was assessed by immunofluorescence staining.

FIGS. 22A-22B. Assessment of the CAR-mediated stimulation in CV-specific CAR Tregs in presence of cell-free synovial fluid from patients with RA. FIG. 22A. Representative dot plots displaying the expression of CD71 against EGFRt after 3 days of culture in presence of whole or cell-free synovial fluid supernatant from RA patient. FIG. 22B. Percentages of CD71$^+$ cells among the EGFRt− and EGFRt+ fractions in CV.28z-CAR Tregs after co-culture with whole or cell-free synovial fluids from RA patients.

FIG. 23A. Schematic representation of the protocol to generate TCR$^{KO}$ CV.28z-CAR$^+$ Tregs. FIG. 23B. CV.28z-CAR$^+$ Treg cell purity after enrichment by flow cytometry at day 9. Top dot plot show cells that did not undergo CRISPR/Cas9 TCR knockout at day 0, whereas cells in the bottom dot plot did.

FIG. 24A. TCR$^{KO}$ CV.28z-CAR$^+$ Tregs were co-cultured with responder CD4$^+$ T cells at the indicated Responder-to-suppressor cell ratio in the presence of plate bound anti-CD3 antibody and CV-pep-SA beads (CVb). 3H-thymidine was added at day 3. Results are shown as percentage of suppression calculated based on the average count per minute (CPM), measured by the incorporation of 3H thymidine, obtained in co-culture of responders and Treg cells and the one obtained in the condition responders alone (experiment was performed in duplicate). FIG. 24B. TCR$^{KO}$ CV.28z-CAR$^+$ Tregs were responder CD4$^+$ T cells at ratio 2:1 (responder:Tregs) in the presence of plate bound anti-CD3 antibody and CVb or Vimentin beads. 19.28z-CAR$^+$ Tregs were co-cultured with CF SE-labeled responder CD4$^+$ T cells at ratio 2:1 (responder:Tregs) in the presence of plate bound anti-CD3 antibody and CVb. Data were analyzed as in FIG. 24A.

DETAILED DESCRIPTION

There is an unmet need to provide therapies for autoimmune diseases. For example, no treatment has yet been discovered to cure rheumatoid arthritis. RA patients undergo life-long treatment with all the associated costs, potential for adverse effects and inconvenience. This first unmet need is addressed by the inventions embodied herein, for curing RA patients by restoring an appropriate immune tolerance. More generally, while the use of CAR T cells in cancer is intensively studied and has shown very promising results in clinical trials, the use of CAR T cells has not yet been tested in autoimmune disorders, nor in other disease states such as tumors or chronic obstructive pulmonary disease (COPD) where citrullinated vimentin (CV) plays a role. Thus, the second unmet need addressed by the invention embodied herein is to apply CAR T cell therapy for the treatment of autoimmune diseases by using Tregs instead of T effectors cells.

Accordingly, as described in detail in the Examples section which follows, a chimeric antigen receptor (CAR) was engineered to specifically target a post-translationally modified protein named citrullinated vimentin (CV) that is expressed in the extracellular matrix of inflamed joints in patients with Rheumatoid Arthritis (RA) and on some tumor cells. The single chain fragment variable (scFv) part of the CV-CAR was obtained from an antibody highly specific for CV protein isolated from the peripheral blood of an RA patient. The CV-specific scFv chain was inserted into a second-generation CAR construct cloned in a lentiviral vector. This CAR construct was introduced into both T effector cells and regulatory T cells. The CV-CAR Tregs were able to specifically recognize their target antigen in presence of CV peptide tetramers and when co-cultured with synovial fluid from RA patients. After recognition of the antigen, CAR-CV Tregs were activated and expanded while maintaining a Treg phenotype.

Chimeric Antigen Receptors and T Cells

Chimeric antigen receptors (CARs) are engineered transmembrane chimeric proteins designed to assign antigen specificity to T-cells. They are recombinant receptors comprising an antigen binding region, a transmembrane region and an intracellular signaling region.

Figure 1:
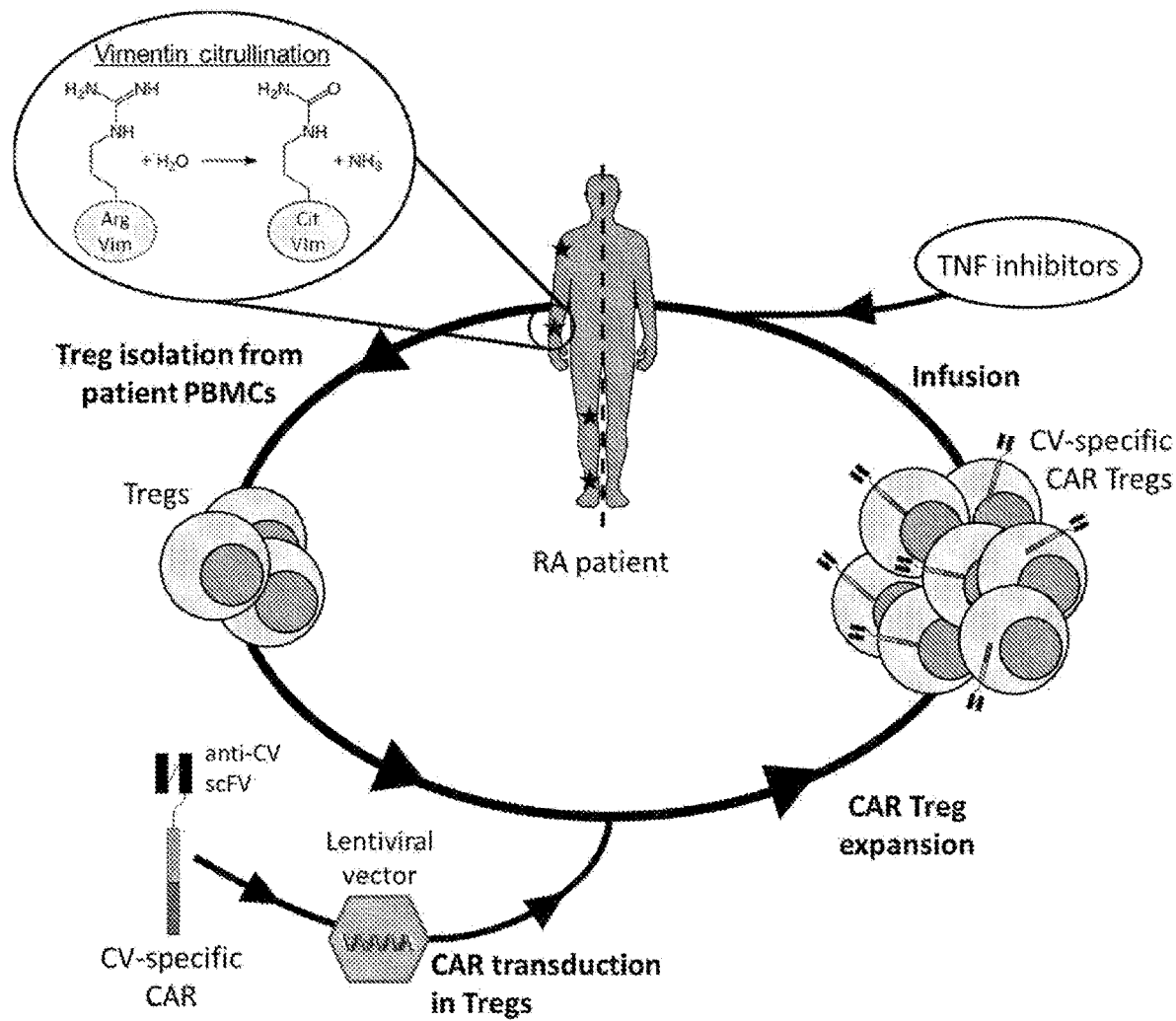
FIG. 1 is a schematic diagram illustrating processes implemented in accordance with some embodiments.
Figure 2:
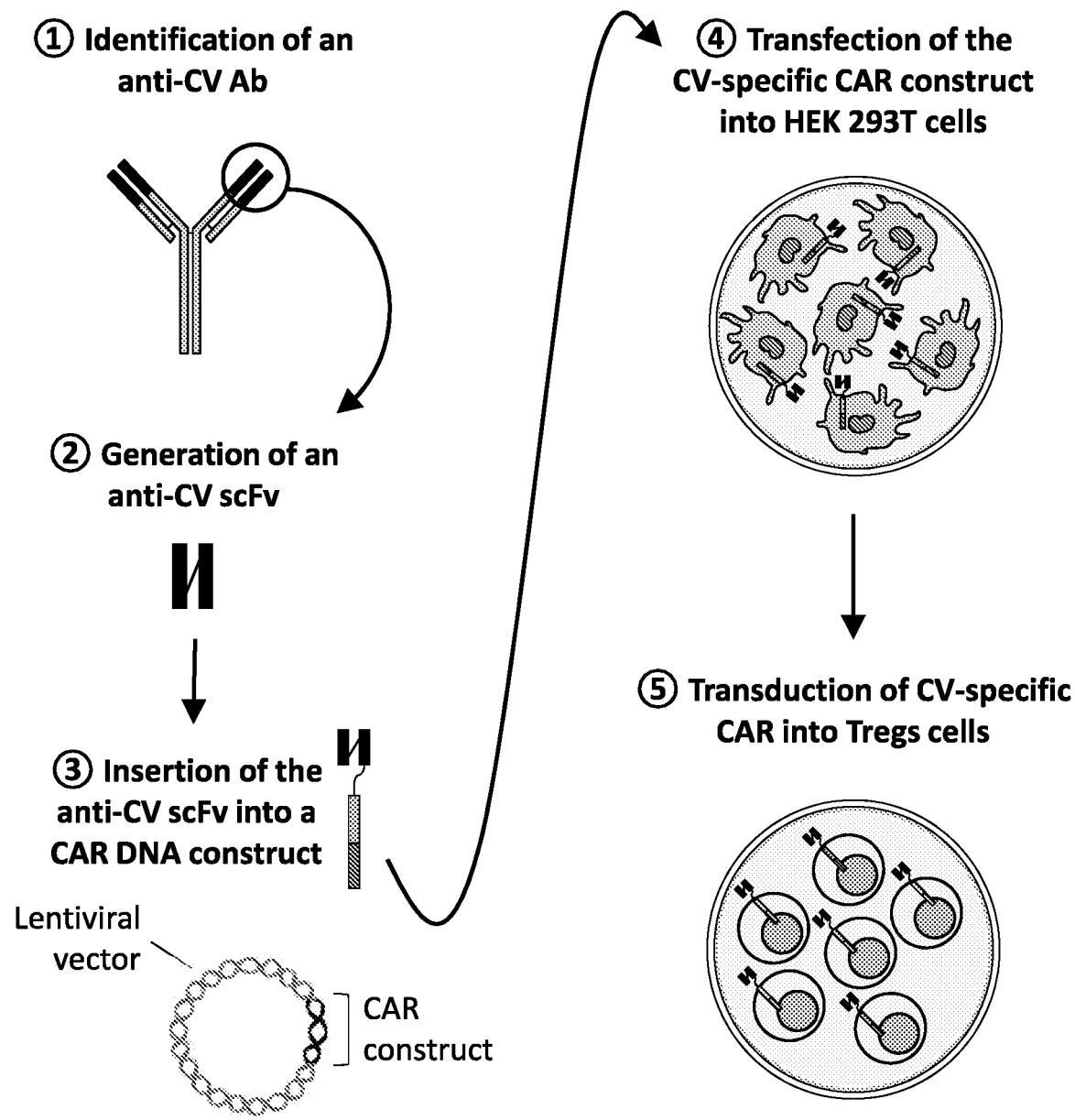
FIG. 2 is a schematic diagram illustrating processes implemented in accordance with some embodiments to generate (CV)-CAR Tregs.

In general, the CV-CAR Tregs were generated to be used in the development of a cell therapy for RA patient. See, for example, FIG. 2. The therapeutic approach taken is to use the Tregs of the patient (autologous) by isolating the cells from a blood sample. Then, the isolated Tregs are genetically reengineered using the lentiviral vector carrying the CV-CAR transgene. CV-CAR Tregs undergo two rounds of expansion in vitro and then are infused to the patient in combination, or not, with anti-TNF treatment to optimize the efficiency of the Tregs at the sites of the disease. See, for example, FIG. 1.

Figure 3:
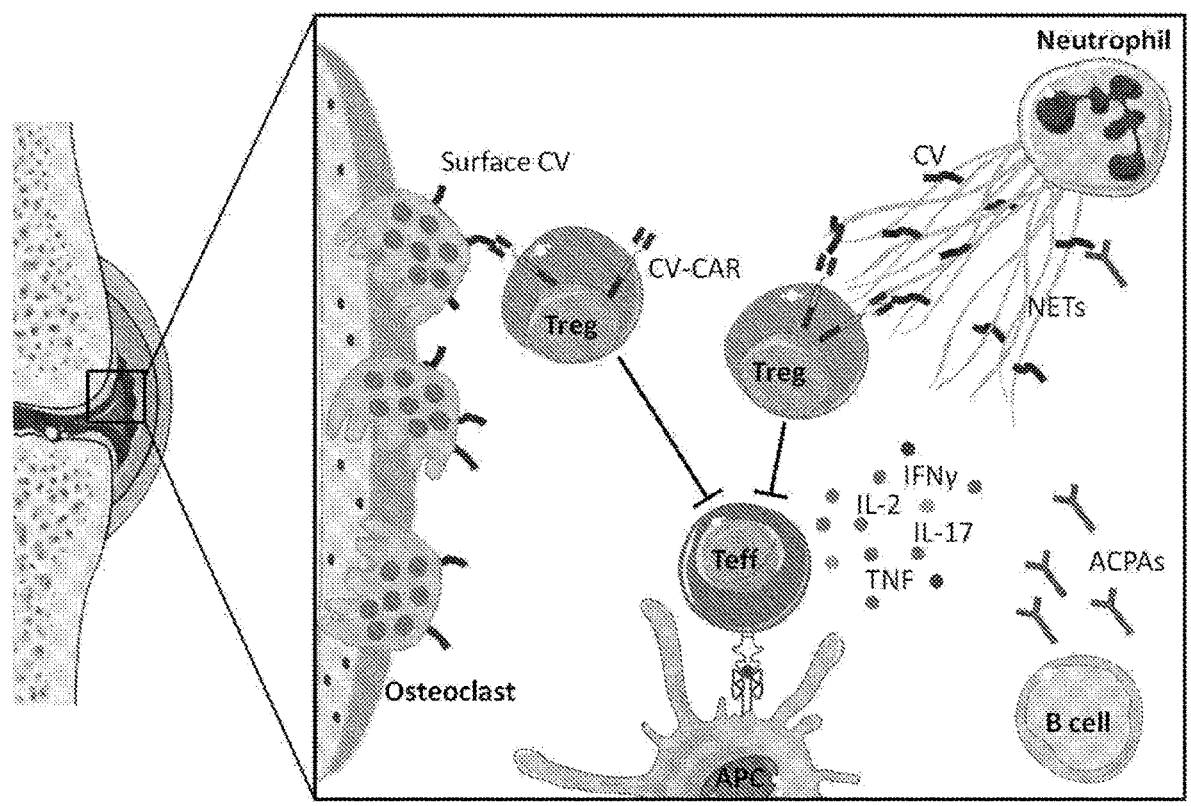
FIG. 3 is a schematic diagram illustrating CV-CAR Tregs targeting antigens in a patient.
Figure 4:
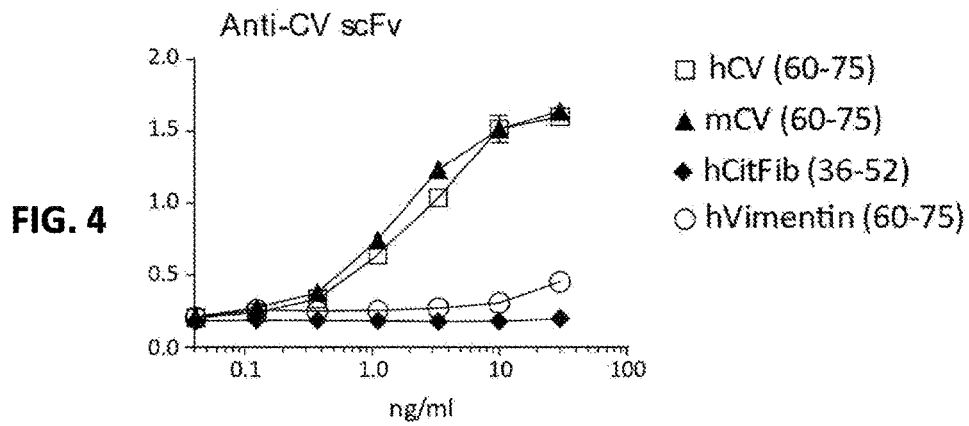
FIG. 4 Assessment of the specificity and affinity for CV of the single-chain variable fragment (scFv) synthesized from BVCA1 antibody. Human and murine samples were assessed. The enzyme-linked immunosorbent assay (ELISA) was used. The results show that, as BVCA1 antibody (described in FIG. 7), BVCA1 scFv is specific for citrullinated vimentin.
Figure 5A:
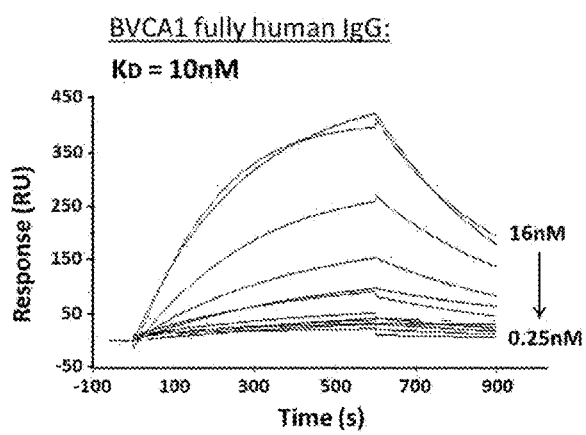
FIG. 5A, 5B. Assessment of the specificity and affinity for CV of the single-chain variable fragment (scFv) synthesized from BVCA1 antibody. The dissociation constant ($K_D$) was measured by using surface plasmon resonance (Biacore system). The results show that (FIG. 5A) $K_D$ between the BVCA1 fully human IgG and the human CV peptide is of 10 nM, and that (FIG. 5B) $K_D$ between the BVCA1 scf and the human CV peptide is of 198 nM. The results show that, as BVCA1 antibody, BVCA1 scFv is specific for citrullinated vimentin.
Figure 5B:
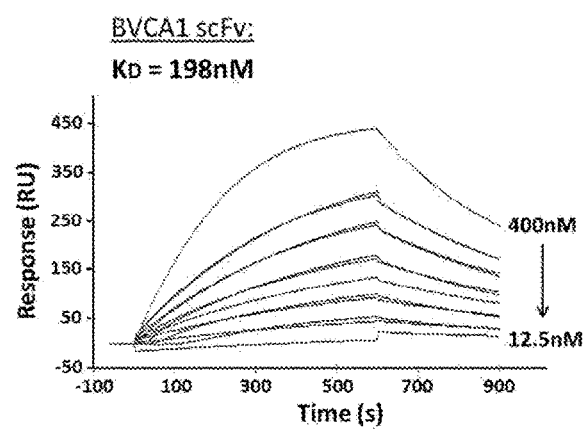
Figure 6:
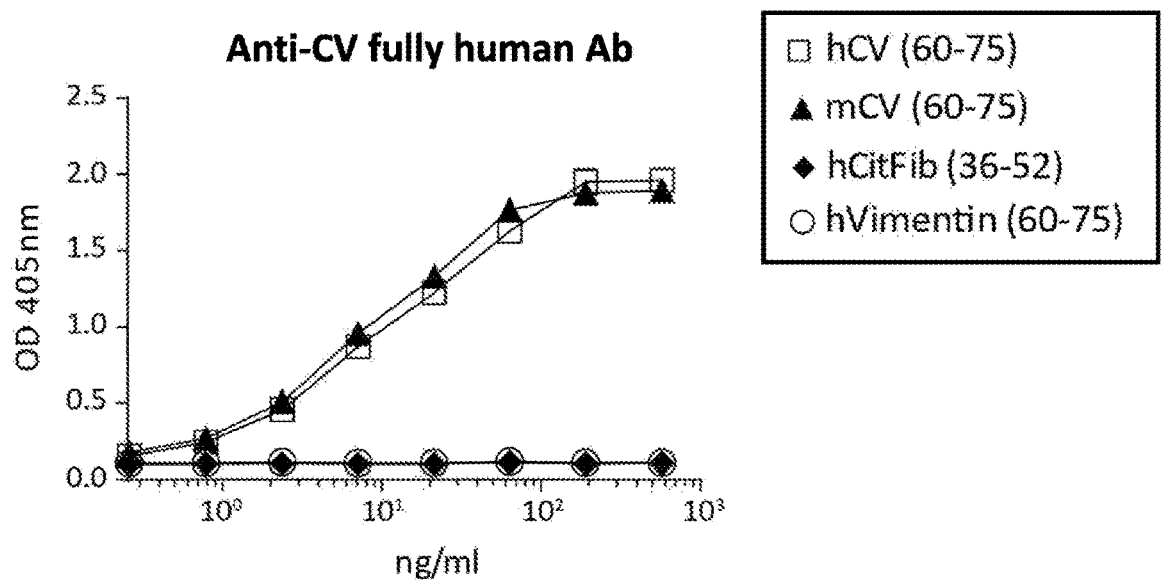
FIG. 6. Comparison of sequences of human and murine vimentin peptide 60-75 showing that the sequences are highly similar and that the three arginine amino acids (abbreviated as R), that are modified into citrulline after citrullination, are in identical locations in both species.
Figure 7:
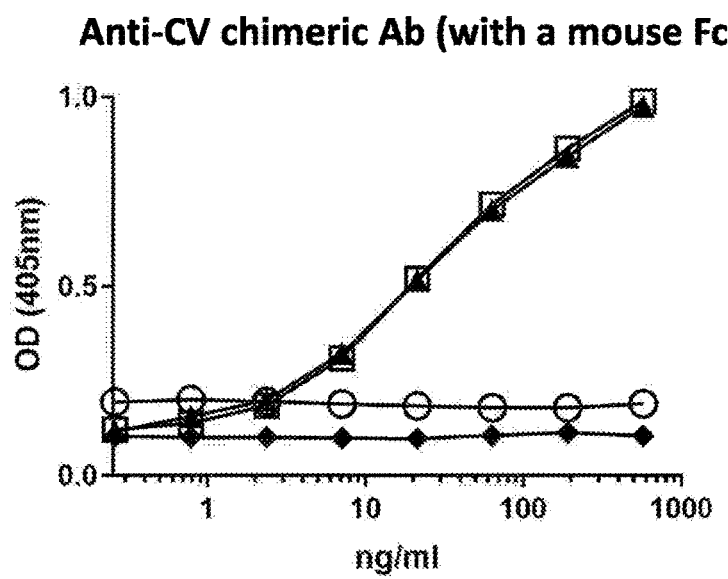
FIG. 7. Assessment of the specificity and affinity for CV by BVCA1 antibody. The enzyme-linked immunosorbent assay (ELISA) was used. The results show that both human and murine BVCA1 antibodies are specific for both human and murine citrullinated vimentin.
Figure 8A:
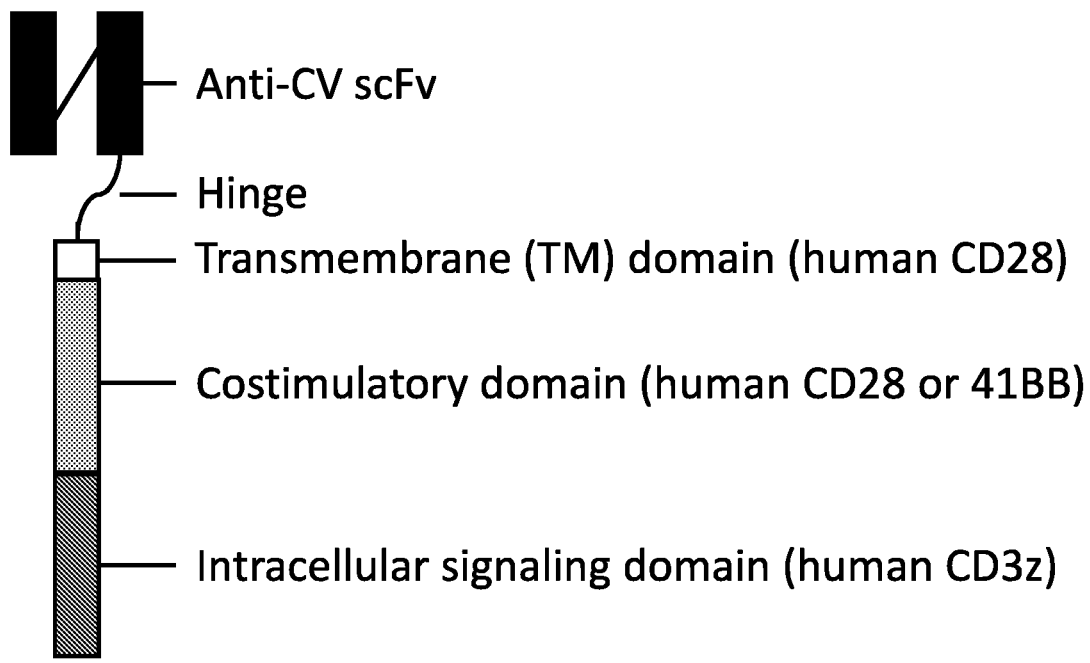
FIG. 8A. Schematic representation of CV-CAR, showing domains of CV-CAR.
Figure 8B:
FIG. 8B. Schematic representation of one example of certain domains of CV-CAR created in accordance with some embodiments. CV-CAR includes αCV scFv, the hinge region and transmembrane motif (TM), a co-stimulatory domain (either CD28 (CV.28z-CAR) or 41BB (CV.41BBz-CAR)), CD3ζ. The native TM portion of CD28 is used; A truncated version of the epidermal growth factor receptor (EGFRt) is in C-terminus to be used as a reporter and is separated from the CAR sequence by a T2A peptide enabling the cleavage of EGFRt reporter.
Figure 9:
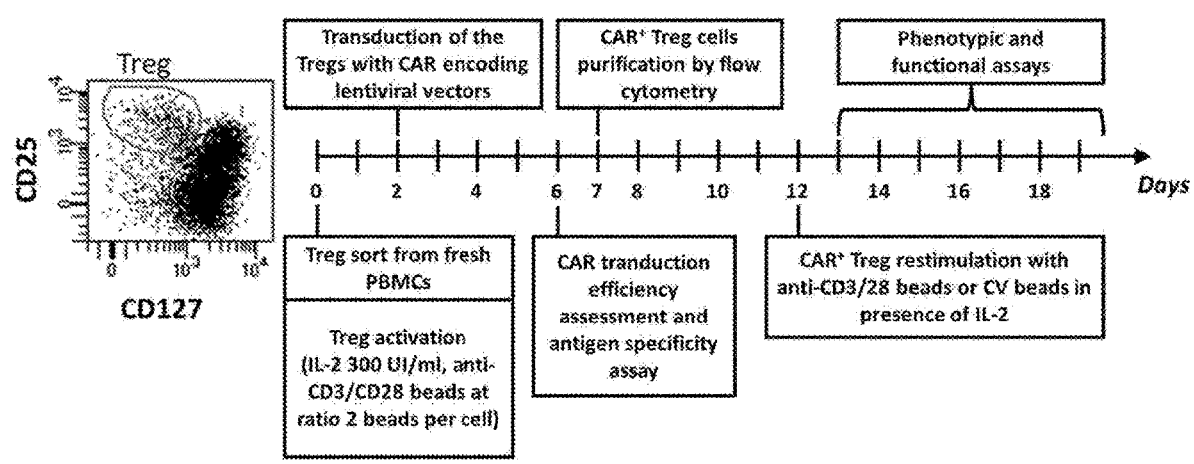
FIG. 9 illustrates an example of a timeline for in vitro generation, expansion and assessment of CV-specific CAR introduced into Tregs.

The antigen-targeted by the CV-CAR is a post-translationally modified antigen and binds the citrullinated version of the protein but not its native form. The CV-CAR is the first CAR developed targeting a citrullinated antigen. The results described in the Examples section, show that CAR targeting a post-translationally modified antigen can successfully recognize their target and activate the cells providing evidence that post-translationally modified antigens represent very interesting therapeutic tools in the development of novel therapeutic strategies in autoimmune disorders and even in some cancers. Moreover, this CAR targets an extracellular matrix protein secreted by some cells into a multimeric complex which may represent a novel use of CARs. The citrullinated vimentin (CV) is present in the extracellular matrix of inflamed joints in patients with Rheumatoid Arthritis (RA) and expressed on some tumor cells. Vimentin is a type III intermediate filament protein and its citrullinated form is abundantly present in the joint microenvironment. CV expression is limited to human spleen, placenta in healthy individual. 50% of RA patients have CV highly present in the synovial tissue. See, for example, FIG. 3.

Accordingly, in certain embodiments, a chimeric antigen receptor (CAR) comprises an antigen specific binding domain, a hinge domain, a transmembrane domain, co-stimulatory domain, and a CD3ζ signaling domain, wherein the antigen specific binding domain specifically binds to citrullinated-vimentin (CV) polypeptides or peptides thereof. The CV polypeptides or peptides thereof are post-translationally modified. In certain embodiments, the co-stimulatory domain comprises a CD28 or a 41BB polypeptide. In certain embodiments, the antigen specific binding domain comprises an antibody, antibody fragment or aptamer. In certain embodiments, the antibody fragment is a single chain fragment. For example, the single chain fragment is a single chain variable fragment (scFv).

In certain embodiments, a chimeric antigen receptor specific for citrullinated-vimentin (CV) polypeptides or peptides comprises SEQ ID NO: 1 or 2.

In certain embodiments, a chimeric antigen receptor comprising a CD28 co-stimulatory domain is encoded by a nucleic acid sequence having at least a 50% sequence identity to a nucleic acid sequence set forth as SEQ ID NO: 1. In certain embodiments, a chimeric antigen receptor comprising a CD28 co-stimulatory domain is encoded by a nucleic acid sequence having at least a 75% sequence identity to a nucleic acid sequence set forth as SEQ ID NO: 1. In certain embodiments, a chimeric antigen receptor comprising a CD28 co-stimulatory domain is encoded by a nucleic acid sequence having at least a 95% sequence identity to a nucleic acid sequence set forth as SEQ ID NO:

1. In certain embodiments, the chimeric antigen receptor comprising the CD28 co-stimulatory domain is encoded by a nucleic acid sequence comprising SEQ ID NO: 1.

In some embodiments, the chimeric antigen receptor comprising the CD28 co-stimulatory domain has a sequence that has at least 50%, 55%, 60%, 65%, 70%, 75%, 80%, 85%, 86%, 87%, 88%, 89%, 90%, 91%, 92%, 93%, 94%, 95%, 96%, 97%, 98%, 99% sequence identity to SEQ ID NO: 1.

In other embodiments, the chimeric antigen receptor comprising the 41BB co-stimulatory domain is encoded by a nucleic acid sequence having at least a 50% sequence identity to a nucleic acid sequence set forth as SEQ ID NO: 2. In certain embodiments, the chimeric antigen receptor comprising the 41BB co-stimulatory domain is encoded by a nucleic acid sequence having at least a 75% sequence identity to a nucleic acid sequence set forth as SEQ ID NO: 2. In certain embodiments, the chimeric antigen receptor comprising the 41BB co-stimulatory domain is encoded by a nucleic acid sequence having at least a 95% sequence identity to a nucleic acid sequence set forth as SEQ ID NO: 2. In certain embodiments, the chimeric antigen receptor comprising the 41BB co-stimulatory domain is encoded by a nucleic acid sequence comprising SEQ ID NO: 2.

In some embodiments, the chimeric antigen receptor comprising the 41BB co-stimulatory domain has a sequence that has at least 50%, 55%, 60%, 65%, 70%, 75%, 80%, 85%, 86%, 87%, 88%, 89%, 90%, 91%, 92%, 93%, 94%, 95%, 96%, 97%, 98%, 99% sequence identity to SEQ ID NO: 2.

In certain embodiments, a chimeric antigen receptor specific for citrullinated-vimentin (CV) polypeptides or peptides comprises one or more chimeric antigen receptor components (e.g., a CV-specific binding domain, a hinge domain, a transmembrane domain, a co-stimulatory domain, and/or a CD3ζ signaling domain) encoded by SEQ ID NO: 1 or 2 or variants thereof having at least about 70% (such as at least about 75%, 80%, 85%, 90%, 91%, 92%, 93%, 94%, 95%, 96%, 97%, 98%, 99%, or greater) sequence identity thereto. For example, in some embodiments, the chimeric antigen receptor comprises an anti-CV scFv encoded by SEQ ID NO: 1 or 2, such as an scFv encoded by the nucleic acid sequence of SEQ ID NO: 7 or a variant thereof having at least about 70% (such as at least about 75%, 80%, 85%, 90%, 91%, 92%, 93%, 94%, 95%, 96%, 97%, 98%, 99%, or greater) sequence identity thereto. In some embodiments, the chimeric antigen receptor comprises a human CD28 spacer domain encoded by SEQ ID NO: 1 or 2, such as a human CD28 spacer domain encoded by the nucleic acid sequence of SEQ ID NO: 8 or a variant thereof having at least about 70% (such as at least about 75%, 80%, 85%, 90%, 91%, 92%, 93%, 94%, 95%, 96%, 97%, 98%, 99%, or greater) sequence identity thereto. In some embodiments, the chimeric antigen receptor comprises a CD28 transmembrane domain encoded by SEQ ID NO: 1 or 2, such as a CD28 transmembrane domain encoded by the nucleic acid sequence of SEQ ID NO: 9 or a variant thereof having at least about 70% (such as at least about 75%, 80%, 85%, 90%, 91%, 92%, 93%, 94%, 95%, 96%, 97%, 98%, 99%, or greater) sequence identity thereto. In some embodiments, the chimeric antigen receptor comprises a CD3ζ signaling domain encoded by SEQ ID NO: 1 or 2, such as a CD3ζ signaling domain encoded by the nucleic acid sequence of SEQ ID NO: 10 or a variant thereof having at least about 70% (such as at least about 75%, 80%, 85%, 90%, 91%, 92%, 93%, 94%, 95%, 96%, 97%, 98%, 99%, or greater) sequence identity thereto. In some embodiments, the chimeric antigen receptor comprises co-stimulatory domain encoded by SEQ ID NO: 1 or 2, such as a co-stimulator domain encoded by the nucleic acid sequence of SEQ ID NO: 11 or 12 or a variant thereof having at least about 70% (such as at least about 75%, 80%, 85%, 90%, 91%, 92%, 93%, 94%, 95%, 96%, 97%, 98%, 99%, or greater) sequence identity thereto.

In certain embodiments, a chimeric antigen receptor comprising a CD28 co-stimulatory domain is encoded by a nucleic acid sequence having at least a 50% sequence identity to a nucleic acid sequence set forth in SEQ ID NO: 1, such as the nucleic acid sequence of SEQ ID NO: 5. Thus, in some embodiments, the chimeric antigen receptor is encoded by a nucleic acid sequence having at least a 50% (such as at least about 55%, 60%, 65%, 70%, 75%, 80%, 85%, 86%, 87%, 88%, 89%, 90%, 91%, 92%, 93%, 94%, 95%, 96%, 97%, 98%, 99%, or greater) sequence identity to SEQ ID NO: 5. In certain embodiments, a chimeric antigen receptor comprising a CD28 co-stimulatory domain is encoded by a nucleic acid sequence having at least a 75% sequence identity to a nucleic acid sequence set forth as SEQ ID NO: 5. In certain embodiments, a chimeric antigen receptor comprising a CD28 co-stimulatory domain is encoded by a nucleic acid sequence having at least a 95% sequence identity to a nucleic acid sequence set forth as SEQ ID NO: 5. In certain embodiments, the chimeric antigen receptor comprising the CD28 co-stimulatory domain is encoded by a nucleic acid sequence comprising SEQ ID NO: 5.

In some embodiments, the chimeric antigen receptor comprising the CD28 co-stimulatory domain is encoded by a nucleic acid sequence that has at least 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to SEQ ID NO: 5.

In certain embodiments, a chimeric antigen receptor comprising a CD28 co-stimulatory domain comprises an amino acid sequence having at least about 70% (such as at least about 75%, 80%, 85%, 90%, 91%, 92%, 93%, 94%, 95%, 96%, 97%, 98%, 99%, or greater) sequence identity to SEQ ID NO: 13. In some embodiments, the chimeric antigen receptor comprises an amino acid sequence having at least about 80% sequence identity to SEQ ID NO: 13. In some embodiments, the chimeric antigen receptor comprises an amino acid sequence having at least about 90% sequence identity to SEQ ID NO: 13. In some embodiments, the chimeric antigen receptor comprises an amino acid sequence having at least about 95% sequence identity to SEQ ID NO: 13. In some embodiments, the chimeric antigen receptor comprises the amino acid sequence of SEQ ID NO: 13.

In other embodiments, the chimeric antigen receptor comprising the 41BB co-stimulatory domain is encoded by a nucleic acid sequence having at least a 50% sequence identity to a nucleic acid sequence set forth in SEQ ID NO: 2, such as the nucleic acid sequence of SEQ ID NO: 6. Thus, in some embodiments, the chimeric antigen receptor is encoded by a nucleic acid sequence having at least a 50% (such as at least about 55%, 60%, 65%, 70%, 75%, 80%, 85%, 86%, 87%, 88%, 89%, 90%, 91%, 92%, 93%, 94%, 95%, 96%, 97%, 98%, 99%, or greater) sequence identity to SEQ ID NO: 6. In certain embodiments, the chimeric antigen receptor comprising the 41BB co-stimulatory domain is encoded by a nucleic acid sequence having at least a 75% sequence identity to a nucleic acid sequence set forth as SEQ ID NO: 6. In certain embodiments, the chimeric antigen receptor comprising the 41BB co-stimulatory domain is encoded by a nucleic acid sequence having at least a 95% sequence identity to a nucleic acid sequence set forth as SEQ ID NO: 6. In certain embodiments, the chimeric antigen receptor comprising the 41BB co-stimulatory domain is encoded by a nucleic acid sequence comprising SEQ ID NO: 6.

In some embodiments, the chimeric antigen receptor comprising the 41BB co-stimulatory domain is encoded by a nucleic acid sequence that has at least 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to SEQ ID NO: 6.

In certain embodiments, a chimeric antigen receptor comprising a 41BB co-stimulatory domain comprises an amino acid sequence having at least about 70% (such as at least about 75%, 80%, 85%, 90%, 91%, 92%, 93%, 94%, 95%, 96%, 97%, 98%, 99%, or greater) sequence identity to SEQ ID NO: 14. In some embodiments, the chimeric antigen receptor comprises an amino acid sequence having at least about 80% sequence identity to SEQ ID NO: 14. In some embodiments, the chimeric antigen receptor comprises an amino acid sequence having at least about 90% sequence identity to SEQ ID NO: 14. In some embodiments, the chimeric antigen receptor comprises an amino acid sequence having at least about 95% sequence identity to SEQ ID NO: 14. In some embodiments, the chimeric antigen receptor comprises the amino acid sequence of SEQ ID NO: 14.

In certain embodiments, the CAR comprises one or more co-stimulatory domains comprising: CD28, ICOS, OX-40 or 41BB. The intracellular signaling region of a CAR or cell of the invention may comprise signaling regions from one, two, three, four or all five of these proteins in addition to the other regions specified herein. In some embodiments, the CD28 co-stimulatory domain is encoded by the nucleic acid sequence of SEQ ID NO: 11 or a variant thereof having at least about 50% (such as at least about any of 55%, 60%, 65%, 70%, 75%, 80%, 85%, 86%, 87%, 88%, 89%, 90%, 91%, 92%, 93%, 94%, 95%, 96%, 97%, 98%, 99%, or greater) sequence identity to SEQ ID NO: 11. In some embodiments, the CD28 co-stimulatory domain has the amino acid sequence of SEQ ID NO: 19 or a variant thereof having at least about 70% (such as at least about 75%, 80%, 85%, 90%, 91%, 92%, 93%, 94%, 95%, 96%, 97%, 98%, 99%, or greater) sequence identity to SEQ ID NO: 19. In some embodiments, the 41BB co-stimulatory domain is encoded by the nucleic acid sequence of SEQ ID NO: 12 or a variant thereof having at least about 50% (such as at least about any of 55%, 60%, 65%, 70%, 75%, 80%, 85%, 86%, 87%, 88%, 89%, 90%, 91%, 92%, 93%, 94%, 95%, 96%, 97%, 98%, 99%, or greater) sequence identity to SEQ ID NO: 12. In some embodiments, the 41BB co-stimulatory domain has the amino acid sequence of SEQ ID NO: 20 or a variant thereof having at least about 70% (such as at least about 75%, 80%, 85%, 90%, 91%, 92%, 93%, 94%, 95%, 96%, 97%, 98%, 99%, or greater) sequence identity to SEQ ID NO: 20.

The co-stimulatory domains of a CAR or cell of the invention may comprise co-stimulatory domains from both 41BB and CD28. The 41BB co-stimulatory domain can be downstream of the CD28 co-stimulatory domains In certain embodiments, the CAR comprises a CD3ζ signaling domain. In some embodiments, the CD3ζ signaling domain is encoded by the nucleic acid sequence of SEQ ID NO: 10 or a variant thereof having at least about 50% (such as at least about any of 55%, 60%, 65%, 70%, 75%, 80%, 85%, 86%, 87%, 88%, 89%, 90%, 91%, 92%, 93%, 94%, 95%, 96%, 97%, 98%, 99%, or greater) sequence identity to SEQ ID NO: 10. In some embodiments, the CD3ζ signaling domain has the amino acid sequence of SEQ ID NO: 18 or a variant thereof having at least about 70% (such as at least about 75%, 80%, 85%, 90%, 91%, 92%, 93%, 94%, 95%, 96%, 97%, 98%, 99%, or greater) sequence identity to SEQ ID NO: 18.

In certain embodiments, the CAR comprises a transmembrane domain from CD28. In some embodiments, the CD28 transmembrane domain is encoded by the nucleic acid sequence of SEQ ID NO: 9 or a variant thereof having at least about 50% (such as at least about any of 55%, 60%, 65%, 70%, 75%, 80%, 85%, 86%, 87%, 88%, 89%, 90%, 91%, 92%, 93%, 94%, 95%, 96%, 97%, 98%, 99%, or greater) sequence identity to SEQ ID NO: 9. In some embodiments, the CD28 transmembrane domain has the amino acid sequence of SEQ ID NO: 17 or a variant thereof having at least about 70% (such as at least about 75%, 80%, 85%, 90%, 91%, 92%, 93%, 94%, 95%, 96%, 97%, 98%, 99%, or greater) sequence identity to SEQ ID NO: 17.

The CAR may also comprise a spacer or hinge region situated between the antigen binding region and T cell plasma membrane. Commonly a spacer or hinge is a sequence derived from IgG subclass IgG1, IgG4, IgD or CD8. In certain embodiments, the hinge region comprises a CD28 motif. The hinge region can have any length. In some embodiments, the hinge region comprises 1 amino acid or 10 amino acids or 20 amino acids or 50 amino acids or 60 amino acids or 70 amino acids or 80 amino acids or 100 amino acids or 120 amino acids or 140 amino acids or 160 amino acids or 180 amino acids or 200 amino acids or 250 amino acids or 300 amino acids or any number therebetween. In some embodiments, the spacer is encoded by the nucleic acid sequence of SEQ ID NO: 8 or a variant thereof having at least about 50% (such as at least about any of 55%, 60%, 65%, 70%, 75%, 80%, 85%, 86%, 87%, 88%, 89%, 90%, 91%, 92%, 93%, 94%, 95%, 96%, 97%, 98%, 99%, or greater) sequence identity to SEQ ID NO: 8. In some embodiments, the spacer has the amino acid sequence of SEQ ID NO: 16 or a variant thereof having at least about 70% (such as at least about 75%, 80%, 85%, 90%, 91%, 92%, 93%, 94%, 95%, 96%, 97%, 98%, 99%, or greater) sequence identity to SEQ ID NO: 16.

A CAR may further comprise a linker region. This may be rich in glycine for flexibility. The linker region may be rich in serine and threonine for solubility. The linker region can connect to N-terminus of variable heavy (VH) chain with the C-terminus of the variable light (VL) chain or vice versa.

Antigen Binding Domain

In certain embodiments, the antigen binding domain is or comprises an antibody or antibody fragment. In certain embodiments, the antibodies are human antibodies, including any known to bind a targeting molecule. The term "antibody" herein is used in the broadest sense and includes polyclonal and monoclonal antibodies, including intact antibodies and functional (antigen-binding) antibody fragments, including fragment antigen binding (Fab) fragments, F(ab')$_2$ fragments, Fab' fragments, Fv fragments, recombinant IgG (rIgG) fragments, variable heavy chain ($V_H$) regions capable of specifically binding the antigen, single chain antibody fragments, including single chain variable fragments (scFv), and single domain antibodies (e.g., sdAb, sdFv, nanobody, camelid nanobody) or fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific, antibodies, diabodies, triabodies, and tetrabodies, tandem di-scFv, tandem tri-scFv. Unless otherwise stated, the term "antibody" should be understood to encompass functional antibody fragments thereof. The term also encompasses intact or full-length antibodies, including antibodies of any class or sub-class, including IgG and sub-classes thereof, IgM, IgE, IgA, and IgD.

In some embodiments, the antigen-binding domain is a humanized antibody of fragments thereof. A "humanized" antibody is an antibody in which all or substantially all CDR amino acid residues are derived from non-human CDRs and all or substantially all FR amino acid residues are derived from human FRs. A humanized antibody optionally may include at least a portion of an antibody constant region derived from a human antibody. A "humanized form" of a non-human antibody, refers to a variant of the non-human antibody that has undergone humanization, typically to reduce immunogenicity to humans, while retaining the specificity and affinity of the parental non-human antibody. In some embodiments, some FR residues in a humanized antibody are substituted with corresponding residues from a non-human antibody (e.g., the antibody from which the CDR residues are derived), e.g., to restore or improve antibody specificity or affinity In some embodiments, the heavy and light chains of an antibody can be full-length or can be an antigen-binding portion (a Fab, F(ab')2, Fv or a single chain Fv fragment (scFv)). In other embodiments, the antibody heavy chain constant region is chosen from, e.g., IgG1, IgG2, IgG3, IgG4, IgM, IgA1, IgA2, IgD, and IgE, particularly chosen from, e.g., IgG1, IgG2, IgG3, and IgG4, more particularly, IgG1 (e.g., human IgG1). In another embodiment, the antibody light chain constant region is chosen from, e.g., kappa or lambda, particularly kappa.

Among the provided antibodies are antibody fragments. An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; variable heavy chain ($V_H$) regions, single-chain antibody molecules such as scFvs and single-domain $V_H$ single antibodies; and multispecific antibodies formed from antibody fragments. In particular embodiments, the antibodies are single-chain antibody fragments comprising a variable heavy chain region and/or a variable light chain region, such as scFvs.

The term "variable region" or "variable domain", when used in reference to an antibody, such as an antibody fragment, refers to the domain of an antibody heavy or light chain that is involved in binding the antibody to antigen. The variable domains of the heavy chain and light chain ($V_H$ and $V_L$, respectively) of a native antibody generally have similar structures, with each domain comprising four conserved framework regions (FRs) and three CDRs. (See, e.g., Kindt et al. Kuby Immunology, 6th ed., W.H. Freeman and Co., page 91 (2007). A single $V_H$ or $V_L$ domain may be sufficient to confer antigen-binding specificity. Furthermore, antibodies that bind a particular antigen may be isolated using a $V_H$ or $V_L$ domain from an antibody that binds the antigen to screen a library of complementary $V_L$ or $V_H$ domains, respectively. See, e.g., Portolano et al., *J. Immunol.* 150: 880-887 (1993); Clarkson et al., *Nature* 352:624-628 (1991).

Single-domain antibodies are antibody fragments comprising all or a portion of the heavy chain variable domain or all or a portion of the light chain variable domain of an antibody. In certain embodiments, a single-domain antibody is a human single-domain antibody.

Antibody fragments can be made by various techniques, including but not limited to proteolytic digestion of an intact antibody as well as production by recombinant host cells. In some embodiments, the antibodies are recombinantly-produced fragments, such as fragments comprising arrangements that do not occur naturally, such as those with two or more antibody regions or chains joined by synthetic linkers, e.g., peptide linkers, and/or that are may not be produced by enzyme digestion of a naturally-occurring intact antibody. In some aspects, the antibody fragments are scFvs.

In certain embodiments, the antibody or antibody fragments of the CAR have high binding affinity for a specific target antigen or post-translationally modified target antigens. In embodiments, the increased binding affinity is greater than effected by a reference antigen.

In certain embodiments, the chimeric antigen specifically binds to a CV peptide having at least a 50% sequence identity to SEQ ID NO: 3 or 4. In certain embodiments, the chimeric antigen specifically binds to a CV peptide having at least a 75% sequence identity to SEQ ID NO: 3 or 4. In certain embodiments, the chimeric antigen specifically binds to a CV peptide having at least a 95% sequence identity to SEQ ID NO: 3 or 4.

In certain embodiments, the chimeric antigen specifically binds to a CV peptide having at least a 50% sequence identity to SEQ ID NO: 21 or 22. In certain embodiments, the chimeric antigen specifically binds to a CV peptide having at least a 75% sequence identity to SEQ ID NO: 21 or 22. In certain embodiments, the chimeric antigen specifically binds to a CV peptide having at least a 95% sequence identity to SEQ ID NO: 21 or 22.

In certain embodiments, the chimeric antigen specifically binds to a CV peptide.

T cells: Regulatory T cells (Tregs) are important in the maintenance of immune cell homeostasis as evidenced by the catastrophic consequences of genetic or physical ablation of the Treg population. Specifically, Treg cells maintain order in the immune system by enforcing a dominant negative regulation on other immune cells. Broadly classified into natural or adaptive (induced) Tregs; natural Tregs are CD4$^+$CD25$^+$ T-cells which develop and emigrate from the thymus to perform their key role in immune homeostasis. Adaptive Tregs are non-regulatory CD4$^+$ T-cells which acquire CD25 (IL-2R alpha) expression outside of the thymus, and are typically induced by inflammation and disease processes, such as autoimmunity and cancer.

There is increasing evidence that Tregs manifest their function through a myriad of mechanisms that include the secretion of immunosuppressive soluble factors such as IL-9, IL-10 and TGF beta, cell-contact-mediated regulation via the high affinity TCR and other costimulatory molecules such as CTLA-4, GITR, and cytolytic activity. Under the influence of TGF beta, adaptive Treg cells mature in peripheral sites, including mucosa-associated lymphoid tissue (MALT), from CD4$^+$ Treg precursors, where they acquire the expression of markers typical of Tregs, including CD25, CTLA4 and GITR/AITR. Upon up-regulation of the transcription factor Foxp3, Treg cells begin their suppressive effect. This includes the secretion of cytokines including IL-10 and TGF beta which may induce cell-cycle arrest or apoptosis in effector T cells, and blocking co-stimulation and maturation of dendritic cells.

Isolation of Viable Treg Cells

The procedures used to isolate Treg cells are provided in detail in the Examples section which follows.

In general, T regulatory cells were originally identified as a CD4$^+$CD25$^+$ T cell population with the capacity to suppress an immune response. The identification of Foxp3 as the "master-regulator" of Tregs was a critical step in defining Tregs as a distinct T cell lineage. The identification of additional antigenic markers on the surface of Tregs has enabled identification and FACS sorting of viable Tregs to greater purity, resulting in a more highly-enriched and suppressive Treg population. In addition to CD4 and CD25, it is now known that both mouse and human Tregs express GITR/AITR, CTLA-4, but express only low levels of CD127 (IL-7Ra). Moreover, Tregs can exist in different states which can be identified based on their expression of surface markers. Tregs which develop in the thymus from $CD4^+$ thymocytes are known as "natural" Tregs, however Tregs can also be induced in the periphery from naïve $CD4^+$ T cells in response to low-dose engagement of the TCR, TGF beta and IL-2. These "induced" Tregs secrete the immunosuppressive cytokine IL-10. The phenotype of Tregs changes again as they become activated, and markers including GARP in mouse and human, and CD103 in mouse have been shown to be useful for the identification of activated Tregs. CD45RO and CD45RA are exclusively expressed by distinct subsets of human CD4 cells, and can be used to divide human $CD4H^+FoxP3^+$ T cells into three phenotypically and functionally distinct subpopulations: $CD45RA^+CD25^+FoxP3^{low}$ resting Treg cells and $CD45RO^+CD25^{high}FoxP3^{high}$ activated Treg cells, both of which were suppressive in vitro, and proinflammatory cytokine-producing $CD45RO^+CD25^+FoxP3^{low}$ nonsuppressive effector T cells (Teffs).

Accordingly, in certain embodiments, an isolated T cell is modified to express: a chimeric antigen receptor (CAR) comprising an antigen binding domain linked to at least one co-stimulatory domain and CD3ζ signaling domain, wherein the antigen binding domain comprises a single chain variable fragment (scFv) which specifically binds to citrullinated-vimentin (CV). In certain embodiments, the co-stimulatory domain comprises a CD28 or a 41BB polypeptide. In certain embodiments, the chimeric antigen receptor comprising the CD28 co-stimulatory domain has a sequence that has at least 50%, 55%, 60%, 65%, 70%, 75%, 80%, 85%, 86%, 87%, 88%, 89%, 90%, 91%, 92%, 93%, 94%, 95%, 96%, 97%, 98%, 99% sequence identity to SEQ ID NO: 1. In some embodiments, the chimeric antigen receptor comprising the 41BB co-stimulatory domain has a sequence that has at least 50%, 55%, 60%, 65%, 70%, 75%, 80%, 85%, 86%, 87%, 88%, 89%, 90%, 91%, 92%, 93%, 94%, 95%, 96%, 97%, 98%, 99% sequence identity to SEQ ID NO: 2. In certain embodiments, the chimeric antigen receptor comprising the CD28 co-stimulatory domain comprises one or more CAR components (e.g., a CV-specific binding domain, a hinge domain, a transmembrane domain, a co-stimulatory domain, and/or a CD3ζ signaling domain) encoded by a nucleic acid sequence that has at least 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to SEQ ID NO: 5. In certain embodiments, the chimeric antigen receptor comprising the CD28 co-stimulatory domain comprises one or more CAR components (e.g., a CV-specific binding domain, a hinge domain, a transmembrane domain, a co-stimulatory domain, and/or a CD3ζ signaling domain) selected from an amino acid sequence that has at least 70% (such as at least about 75%, 80%, 85%, 90%, 91%, 92%, 93%, 94%, 95%, 96%, 97%, 98%, 99%, or greater) sequence identity to SEQ ID NO: 13. In some embodiments, the chimeric antigen receptor comprising the 41BB co-stimulatory domain comprises one or more CAR components (e.g., a CV-specific binding domain, a hinge domain, a transmembrane domain, a co-stimulatory domain, and/or a CD3ζ signaling domain) encoded by a nucleic acid sequence that has at least 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to SEQ ID NO: 6. In some embodiments, the chimeric antigen receptor comprising the 41BB co-stimulatory domain comprises one or more CAR components (e.g., a CV-specific binding domain, a hinge domain, a transmembrane domain, a co-stimulatory domain, and/or a CD3ζ signaling domain) selected from an amino acid sequence that has at least 70% (such as at least about 75%, 80%, 85%, 90%, 91%, 92%, 93%, 94%, 95%, 96%, 97%, 98%, 99%, or greater) sequence identity to SEQ ID NO: 14. In certain embodiments, the chimeric antigen receptor comprising the CD28 co-stimulatory domain is encoded by a nucleic acid sequence that has at least 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to SEQ ID NO: 5. In certain embodiments, the chimeric antigen receptor comprising the CD28 co-stimulatory domain comprises an amino acid sequence that has at least 70% (such as at least about 75%, 80%, 85%, 90%, 91%, 92%, 93%, 94%, 95%, 96%, 97%, 98%, 99%, or greater) sequence identity to SEQ ID NO: 13. In some embodiments, the chimeric antigen receptor comprising the 41BB co-stimulatory domain is encoded by a nucleic acid sequence that has at least 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to SEQ ID NO: 6. In some embodiments, the chimeric antigen receptor comprising the 41BB co-stimulatory domain comprises an amino acid sequence that has at least 70% (such as at least about 75%, 80%, 85%, 90%, 91%, 92%, 93%, 94%, 95%, 96%, 97%, 98%, 99%, or greater) sequence identity to SEQ ID NO: 14.

In certain embodiments, the T cell is a mammalian regulatory T cell (Treg), wherein the Treg cell is $CD4^+$, $CD25^+$, $CD127^-$, $FOXP3^+$ and/or $Helios^{+/-}$. In other embodiments, the T cell is a mammalian regulatory T cell (Treg), wherein the Treg cell is $CD4^+$, $CD25^+$, $CD127^-$, and/or $FOXP3^+$.

Methods for Isolation of Cells

Any number of methods known in the art can be used to isolate cells, such as Tregs, or any other cell type that may be used in carrying out the treatment of a subject. Thus, also provided are various other genetically engineered cells expressing the chimeric antigen receptors e.g., CARs. The cells generally are eukaryotic cells, such as mammalian cells, and typically are human cells. In some embodiments, the cells are derived from the blood, bone marrow, lymph, or lymphoid organs, are cells of the immune system, such as cells of the innate or adaptive immunity, e.g., myeloid or lymphoid cells, including lymphocytes, typically T cells and/or NK cells. Other exemplary cells include stem cells, such as multipotent and pluripotent stem cells, including induced pluripotent stem cells (iPSCs). The cells typically are primary cells, such as those isolated directly from a subject and/or isolated from a subject and frozen. In some embodiments, the cells include one or more subsets of T cells or other cell types, such as whole T cell populations, $CD4^+$ cells, $CD8^+$ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to the subject to be treated, the cells may be allogeneic and/or autologous. Among the methods include off-the-shelf methods. In some aspects, such as for off-the-shelf technologies, the cells are pluripotent and/or multipotent, such as stem cells, such as induced pluripotent stem cells (iPSCs). In some embodiments, the methods include isolating cells from the subject, preparing, processing, culturing, and/or engineering them, as described herein, and re-introducing them into the same patient, before or after cryopreservation.

Among the sub-types and subpopulations of T cells and/or of CD4+ and/or of CD8+ T cells are naive T ($T_N$) cells, effector T cells ($T_{EFF}$), memory T cells and sub-types thereof, such as stem cell memory T ($T_{SCM}$), central memory T ($T_{CM}$ effector memory T ($T_{EM}$), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as $T_H1$ cells, $T_H2$ cells, $T_H3$ cells, $T_H17$ cells, $T_H9$ cells, $T_H22$ cells, follicular helper T cells, alpha/beta T cells, and delta/gamma T cells.

In some embodiments, the cells are natural killer (NK) cells. In some embodiments, the cells are monocytes or granulocytes, e.g., myeloid cells, macrophages, neutrophils, dendritic cells, mast cells, eosinophils, and/or basophils.

In some embodiments, the cells include one or more nucleic acids introduced via genetic engineering, and thereby express recombinant or genetically engineered products of such nucleic acids. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature, including one comprising chimeric combinations of nucleic acids encoding various domains from multiple different cell types.

Exemplary methods of isolating cells and engineering these cells with a CAR are described in the Examples section which follows.

In some embodiments, preparation of the engineered cells includes one or more culture and/or preparation steps. The cells for introduction of the CAR, may be isolated from a sample, such as a biological sample, e.g., one obtained from or derived from a subject. In some embodiments, the subject from which the cell is isolated is one having the disease or condition or in need of a cell therapy or to which cell therapy will be administered. The subject in some embodiments is a human in need of a particular therapeutic intervention, such as the adoptive cell therapy for which cells are being isolated, processed, and/or engineered.

Accordingly, the cells in some embodiments are primary cells, e.g., primary human cells. The samples include tissue, fluid, and other samples taken directly from the subject, as well as samples resulting from one or more processing steps, such as separation, centrifugation, genetic engineering (e.g. transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some aspects, the sample from which the cells are derived or isolated is blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some embodiments, the cells are derived from cell lines, e.g., T cell lines. The cells in some embodiments are obtained from a xenogeneic source, for example, from mouse, rat, non-human primate, or pig.

In some embodiments, isolation of the cells includes one or more preparation and/or non-affinity-based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components.

In some examples, cells from the circulating blood of a subject are obtained, e.g., by apheresis or leukapheresis. The samples, in some aspects, contain lymphocytes, including T cells, monocytes, granulocytes, B cells, other nucleated white blood cells, red blood cells, and/or platelets, and in some aspects contains cells other than red blood cells and platelets.

In some embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In some embodiments, the wash solution lacks calcium and/or magnesium and/or many or all divalent cations. In some aspects, a washing step is accomplished a semi-automated "flow-through" centrifuge (for example, the Cobe 2991 cell processor, Baxter) according to the manufacturer's instructions. In some aspects, a washing step is accomplished by tangential flow filtration (TFF) according to the manufacturer's instructions. In some embodiments, the cells are resuspended in a variety of biocompatible buffers after washing, such as, for example, $Ca^{++}/Mg^{++}$ free PBS. In certain embodiments, components of a blood cell sample are removed and the cells directly resuspended in culture media.

In some embodiments, the methods include density-based cell separation methods, such as the preparation of white blood cells from peripheral blood by lysing the red blood cells and centrifugation through a Percoll or Ficoll gradient.

In some embodiments, the isolation methods include the separation of different cell types based on the expression or presence in the cell of one or more specific molecules, such as surface markers, e.g., surface proteins, intracellular markers, or nucleic acid. In some embodiments, any known method for separation based on such markers may be used. In some embodiments, the separation is affinity- or immunoaffinity-based separation. For example, the isolation in some aspects includes separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

Such separation steps can be based on positive selection, in which the cells having bound the reagents are retained for further use, and/or negative selection, in which the cells having not bound to the antibody or binding partner are retained. In some examples, both fractions are retained for further use. In some aspects, negative selection can be particularly useful where no antibody is available that specifically identifies a cell type in a heterogeneous population, such that separation is best carried out based on markers expressed by cells other than the desired population.

The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In some examples, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types. For example, in some aspects, specific subpopulations of T cells, such as cells positive or expressing one or more markers, e.g., $CD4^+$, $CD25^+$, $CD127^-$, $FOXP3^+$ and/or $Helios^+$.

T cells, are isolated by positive or negative selection techniques. For example, $CD3^+$, $CD28^+$ T cells can be positively selected using anti-CD3/anti-CD28 conjugated magnetic beads (e.g., DYNABEADS® M-450 CD3/CD28 T Cell Expander).

In some embodiments, isolation is carried out by enrichment for a particular cell population by positive selection, or depletion of a particular cell population, by negative selection. In some embodiments, positive or negative selection is accomplished by incubating cells with one or more antibodies or other binding agent that specifically bind to one or more surface markers expressed or expressed (marker"1") at a relatively higher level (marker "$1^{high}$") on the positively or negatively selected cells, respectively.

In some embodiments, T cells are separated from a PBMC sample by negative selection of markers expressed on non-T cells, such as B cells, monocytes, or other white blood cells, such as CD 14. In some aspects, a $CD4^+$ or $CD8^+$ selection step is used to separate $CD4^+$ helper and $CD8^+$ cytotoxic T cells. Such $CD4^+$ and $CD8^+$ populations can be further sorted into sub-populations by positive or negative selection for markers expressed or expressed to a relatively higher degree on one or more naive, memory, and/or effector T cell subpopulations.

In some embodiments, $CD8^+$ cells are further enriched for or depleted of naïve, central memory, effector memory, and/or central memory stem cells, such as by positive or negative selection based on surface antigens associated with the respective subpopulation. In some embodiments, enrichment for central memory T ($T_{CM}$) cells is carried out to increase efficacy, such as to improve long-term survival, expansion, and/or engraftment following administration, which in some aspects is particularly robust in such sub-populations. See Terakura et al. (2012) *Blood.* 1:72-82; Wang et al. (2012) *J Immunother.* 35(9):689-701. In some embodiments, combining $T_{CM}$-enriched $CD8^+$ T cells and $CD4^+$ T cells further enhances efficacy.

In some embodiments, the enrichment for central memory T ($T_{CM}$) cells is based on positive or high surface expression of CD45RO, CD62L, CCR7, CD28, CD3, and/or CD127; in some aspects, it is based on negative selection for cells expressing or highly expressing CD45RA and/or granzyme B.

In some aspects, a CD4 expression-based selection step is used to generate the $CD4^+$ cell population or sub-population, such that both the positive and negative fractions from the CD4-based separation are retained and used in subsequent steps of the methods, optionally following one or more further positive or negative selection steps.

In one example, a sample of PBMCs or other white blood cell sample is subjected to selection of $CD4^+$ cells, where both the negative and positive fractions are retained. The negative fraction then is subjected to negative selection based on expression o, for example, CD14 and CD45RA, and positive selection based on a marker characteristic of central memory T cells, such as CD62L or CCR7, where the positive and negative selections are carried out in either order.

$CD4^+$ T helper cells are sorted into naïve, central memory, and effector cells by identifying cell populations that have cell surface antigens. $CD4^+$ lymphocytes can be obtained by standard methods. In some embodiments, naïve $CD4^+$ T lymphocytes are $CD45RO^+$, $CD45RA^+$, $CD62L^+$, $CD4^+$ T cells. In some embodiments, central memory $CD4^+$ cells are $CD62L^+$ and $CD45RO^+$.

In one example, to enrich for $CD4^+$ cells by negative selection, a monoclonal antibody cocktail typically includes antibodies to CD14, CD20, CD11b, CD16, HLA-DR, and CD8. In some embodiments, the antibody or binding partner is bound to a solid support or matrix, such as a magnetic bead or paramagnetic bead, to allow for separation of cells for positive and/or negative selection. For example, in some embodiments, the cells and cell populations are separated or isolated using immunomagnetic (or affinity magnetic) separation techniques (reviewed in Methods in Molecular Medicine, vol. 58: Metastasis Research Protocols, Vol. 2: Cell Behavior In Vitro and In Vivo, p 17-25 Edited by: S. A. Brooks and U. Schumacher© Humana Press Inc., Totowa, NJ).

In some aspects, the sample or composition of cells to be separated is incubated with small, magnetizable or magnetically responsive material, such as magnetically responsive particles or microparticles, such as paramagnetic beads (e.g., such as Dynabeads or MACS beads). The magnetically responsive material, e.g., particle, generally is directly or indirectly attached to a binding partner, e.g., an antibody, that specifically binds to a molecule, e.g., surface marker, present on the cell, cells, or population of cells that it is desired to separate, e.g., that it is desired to negatively or positively select.

In some embodiments, the magnetic particle or bead comprises a magnetically responsive material bound to a specific binding member, such as an antibody or other binding partner. There are many well-known magnetically responsive materials used in magnetic separation methods. Suitable magnetic particles include those described in Molday, U.S. Pat. No. 4,452,773, and in European Patent Specification EP 452342 B, which are hereby incorporated by reference. Colloidal sized particles, such as those described in Owen U.S. Pat. No. 4,795,698, and Liberti et al., U.S. Pat. No. 5,200,084 are other examples.

The incubation generally is carried out under conditions whereby the antibodies or binding partners, or molecules, such as secondary antibodies or other reagents, which specifically bind to such antibodies or binding partners, which are attached to the magnetic particle or bead, specifically bind to cell surface molecules if present on cells within the sample.

In some aspects, the sample is placed in a magnetic field, and those cells having magnetically responsive or magnetizable particles attached thereto will be attracted to the magnet and separated from the unlabeled cells. For positive selection, cells that are attracted to the magnet are retained; for negative selection, cells that are not attracted (unlabeled cells) are retained. In some aspects, a combination of positive and negative selection is performed during the same selection step, where the positive and negative fractions are retained and further processed or subject to further separation steps.

In certain embodiments, the magnetically responsive particles are coated in primary antibodies or other binding partners, secondary antibodies, lectins, enzymes, or streptavidin. In certain embodiments, the magnetic particles are attached to cells via a coating of primary antibodies specific for one or more markers. In certain embodiments, the cells, rather than the beads, are labeled with a primary antibody or binding partner, and then cell-type specific secondary antibody- or other binding partner (e.g., streptavidin)-coated magnetic particles, are added. In certain embodiments, streptavidin-coated magnetic particles are used in conjunction with biotinylated primary or secondary antibodies or biotinylated peptides.

In some embodiments, the magnetically responsive particles are left attached to the cells that are to be subsequently incubated, cultured and/or engineered; in some aspects, the particles are left attached to the cells for administration to a patient. In some embodiments, the magnetizable or magnetically responsive particles are removed from the cells. Methods for removing magnetizable particles from cells are known and include, e.g., the use of competing non-labeled antibodies, magnetizable particles or antibodies conjugated to cleavable linkers, etc. In some embodiments, the magnetizable particles are biodegradable.

In some embodiments, the affinity-based selection is via magnetic-activated cell sorting (MACS) (Miltenyi Biotec, Auburn, CA). Magnetic Activated Cell Sorting (MACS) systems are capable of high-purity selection of cells having magnetized particles attached thereto. In certain embodiments, MACS operates in a mode wherein the non-target and target species are sequentially eluted after the application of the external magnetic field. That is, the cells attached to magnetized particles are held in place while the unattached species are eluted. Then, after this first elution step is completed, the species that were trapped in the magnetic field and were prevented from being eluted are freed in some manner such that they can be eluted and recovered. In certain embodiments, the non-target cells are labelled and depleted from the heterogeneous population of cells.

In certain embodiments, the isolation or separation is carried out using a system, device, or apparatus that carries out one or more of the isolation, cell preparation, separation, processing, incubation, culture, and/or formulation steps of the methods. In some aspects, the system is used to carry out each of these steps in a closed or sterile environment, for example, to minimize error, user handling and/or contamination. In one example, the system is a system as described in International Patent Application, Publication Number WO2009/072003, or US 20110003380 A1.

In some embodiments, the system or apparatus carries out one or more, e.g., all, of the isolation, processing, engineering, and formulation steps in an integrated or self-contained system, and/or in an automated or programmable fashion. In some aspects, the system or apparatus includes a computer and/or computer program in communication with the system or apparatus, which allows a user to program, control, assess the outcome of, and/or adjust various aspects of the processing, isolation, engineering, and formulation steps.

In some aspects, the separation and/or other steps is carried out using CliniMACS system (Miltenyi Biotec), for example, for automated separation of cells on a clinical-scale level in a closed and sterile system. Components can include an integrated microcomputer, magnetic separation unit, peristaltic pump, and various pinch valves. The integrated computer in some aspects controls all components of the instrument and directs the system to perform repeated procedures in a standardized sequence. The magnetic separation unit in some aspects includes a movable permanent magnet and a holder for the selection column. The peristaltic pump controls the flow rate throughout the tubing set and, together with the pinch valves, ensures the controlled flow of buffer through the system and continual suspension of cells.

The CliniMACS system in some aspects uses antibody-coupled magnetizable particles that are supplied in a sterile, non-pyrogenic solution. In some embodiments, after labelling of cells with magnetic particles the cells are washed to remove excess particles. A cell preparation bag is then connected to the tubing set, which in turn is connected to a bag containing buffer and a cell collection bag. The tubing set consists of pre-assembled sterile tubing, including a pre-column and a separation column, and are for single use only. After initiation of the separation program, the system automatically applies the cell sample onto the separation column. Labelled cells are retained within the column, while unlabeled cells are removed by a series of washing steps. In some embodiments, the cell populations for use with the methods described herein are unlabeled and are not retained in the column. In some embodiments, the cell populations for use with the methods described herein are labeled and are retained in the column. In some embodiments, the cell populations for use with the methods described herein are eluted from the column after removal of the magnetic field, and are collected within the cell collection bag.

In certain embodiments, separation and/or other steps are carried out using the CliniMACS Prodigy system (Miltenyi Biotec). The CliniMACS Prodigy system in some aspects is equipped with a cell processing unity that permits automated washing and fractionation of cells by centrifugation. The CliniMACS Prodigy system can also include an onboard camera and image recognition software that determines the optimal cell fractionation endpoint by discerning the macroscopic layers of the source cell product. For example, peripheral blood may be automatically separated into erythrocytes, white blood cells and plasma layers. The CliniMACS Prodigy system can also include an integrated cell cultivation chamber which accomplishes cell culture protocols such as, e.g., cell differentiation and expansion, antigen loading, and long-term cell culture. Input ports can allow for the sterile removal and replenishment of media and cells can be monitored using an integrated microscope. See, e.g., Klebanoff et al. (2012) *J Immunother.* 35(9): 651-660, Terakura et al. (2012) *Blood.* 1:72-82, and Wang et al. (2012) *Immunother.* 35(9):689-701.

In some embodiments, a cell population described herein is collected and enriched (or depleted) via flow cytometry, in which cells stained for multiple cell surface markers are carried in a fluidic stream. In some embodiments, a cell population described herein is collected and enriched (or depleted) via preparative scale (FACS)-sorting. In certain embodiments, a cell population described herein is collected and enriched (or depleted) by use of microelectromechanical systems (MEMS) chips in combination with a FACS-based detection system (see, e.g., WO 2010/033140, Cho et al. (2010) *Lab Chip* 10, 1567-1573; and Godin et al. (2008) *J Biophoton.* 1(5):355-376. In both cases, cells can be labeled with multiple markers, allowing for the isolation of well-defined T cell subsets at high purity.

In some embodiments, the antibodies or binding partners are labeled with one or more detectable marker, to facilitate separation for positive and/or negative selection. For example, separation may be based on binding to fluorescently labeled antibodies. In some examples, separation of cells based on binding of antibodies or other binding partners specific for one or more cell surface markers are carried in a fluidic stream, such as by fluorescence-activated cell sorting (FACS), including preparative scale (FACS) and/or microelectromechanical systems (MEMS) chips, e.g., in combination with a flow-cytometric detection system. Such methods allow for positive and negative selection based on multiple markers simultaneously.

In some embodiments, the preparation methods include steps for freezing, e.g., cryopreserving, the cells, either before or after isolation, incubation, and/or engineering. In some embodiments, the freeze and subsequent thaw step removes granulocytes and, to some extent, monocytes in the cell population. In some embodiments, the cells are suspended in a freezing solution, e.g., following a washing step to remove plasma and platelets. Any of a variety of known freezing solutions and parameters in some aspects may be used. One example involves using PBS containing 20% DMSO and 8% human serum albumin (HSA), or other suitable cell freezing media. This is then diluted 1:1 with media so that the final concentration of DMSO and HSA are 10% and 4%, respectively. The cells are then frozen to −80° C. at a rate of 1° per minute and stored in the vapor phase of a liquid nitrogen storage tank.

In some embodiments, the provided methods include cultivation, incubation, culture, and/or genetic engineering steps. For example, in some embodiments, provided are methods for incubating and/or engineering the depleted cell populations and culture-initiating compositions.

Thus, in some embodiments, the cell populations are incubated in a culture-initiating composition. The incubation and/or engineering may be carried out in a culture vessel, such as a unit, chamber, well, column, tube, tubing set, valve, vial, culture dish, bag, or other container for culture or cultivating cells.

In some embodiments, the cells are incubated and/or cultured prior to or in connection with genetic engineering. The incubation steps can include culture, cultivation, stimulation, activation, and/or propagation. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor.

The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some embodiments, the stimulating conditions or agents include one or more agent, e.g., ligand, which is capable of activating an intracellular signaling domain of a TCR complex. In some aspects, the agent turns on or initiates TCR/CD3 intracellular signaling cascade in a T cell. Such agents can include antibodies, such as those specific for a TCR, e.g. anti-CD3. In some embodiments, the stimulating conditions include one or more agent, e.g. ligand, which is capable of stimulating a costimulatory receptor, e.g., anti-CD28. In some embodiments, such agents and/or ligands may be, bound to solid support such as a bead, and/or one or more cytokines. Optionally, the expansion method may further comprise the step of adding anti-CD3 and/or anti CD28 antibody to the culture medium (e.g., at a concentration of at least about 0.5 ng/ml). In some embodiments, the stimulating agents include IL-2, IL-15 and/or IL-7. In some aspects, the IL-2 concentration is at least about 10 units/mL.

In some aspects, incubation is carried out in accordance with techniques such as those described in U.S. Pat. No. 6,040,177 to Riddell et al.; Klebanoff et al. (2012) *J Immunother.* 35(9): 651-660, Terakura et al. (2012) *Blood.* 1:72-82, and/or Wang et al. (2012) *J Immunother* 35(9):689-701.

In some embodiments, the T cells are expanded by adding to the culture-initiating composition feeder cells, such as non-dividing peripheral blood mononuclear cells (PBMC), (e.g., such that the resulting population of cells contains at least about 5, 10, 20, or 40 or more PBMC feeder cells for each T lymphocyte in the initial population to be expanded); and incubating the culture (e.g. for a time sufficient to expand the numbers of T cells). In some aspects, the non-dividing feeder cells can comprise gamma-irradiated PBMC feeder cells. In some embodiments, the PBMC are irradiated with gamma rays in the range of about 3000 to 3600 rads to prevent cell division. In some aspects, the feeder cells are added to culture medium prior to the addition of the populations of T cells.

In some embodiments, the stimulating conditions include temperature suitable for the growth of human T lymphocytes, for example, at least about 25 degrees Celsius, generally at least about 30 degrees, and generally at or about 37 degrees Celsius. Optionally, the incubation may further comprise adding non-dividing EBV-transformed lymphoblastoid cells (LCL) as feeder cells. LCL can be irradiated with gamma rays in the range of about 6000 to 10,000 rads. The LCL feeder cells in some aspects is provided in any suitable amount, such as a ratio of LCL feeder cells to initial T lymphocytes of at least about 10:1.

Methods of Treatment

In certain embodiments, a method of treating a subject diagnosed with rheumatoid arthritis, comprises isolating T lymphocytes from a biological sample obtained from the subject; separating CD4$^+$ T regulatory Cells (Treg) from conventional T cells (Tconv), wherein the Treg cells are CD4$^+$CD25$^+$CD127$^-$ and the Tconv are CD4$^+$CD25$^-$CD127$^+$; transducing the Treg cells with an expression vector encoding a chimeric antigen receptor (CAR) which specifically binds to a citrullinated-vimentin (CV) antigen;

stimulating the transduced Treg with the CV antigen at least once ex vivo to obtain Treg cells specific for the CV antigen; and reinfusing the Treg into the subject, thereby treating the subject. In certain embodiments, the Treg cells are autologous cells. CAR-T cells may be generated from any suitable source of T cells known in the art including, but not limited to, T cells collected from a subject. The subject may be a patient with an autoimmune disease such as rheumatoid arthritis, in need of CAR-T cell therapy or a subject of the same species as the subject with the autoimmune disease in need of CAR-T cell therapy. The collected T cells may be expanded ex vivo using methods commonly known in the art before transduction with a CAR to generate a CAR-T cell.

Citrullinated-vimentin (CV) antigen is also associated with tumors and COPD, therefore, in certain embodiments, methods of treating a tumor or chronic obstructive pulmonary disease (COPD) comprises isolating T lymphocytes from a biological sample obtained from the subject; separating $CD4^+$ T regulatory Cells (Treg) from conventional T cells (Tconv), wherein the Treg cells are $CD4^+CD25^+CD127^-$ and the Tconv are $CD4^+CD25^-CD127^+$; transducing the Treg cells with an expression vector encoding a chimeric antigen receptor (CAR) which specifically binds to a citrullinated-vimentin (CV) antigen; stimulating the transduced Treg with the CV antigen at least once ex vivo to obtain Treg cells specific for the CV antigen; and reinfusing the Treg into the subject, thereby treating the subject. In certain embodiments, the Treg cells are autologous cells. CAR-T cells may be generated from any suitable source of T cells known in the art including, but not limited to, T cells collected from a subject.

Methods for CAR design, delivery and expression in T cells, and the manufacturing of clinical-grade CAR-T cell populations are known in the art. See, for example, Lee et al., *Clin. Cancer Res.* 2012, 18(10): 2780-90, hereby incorporated by reference in its entirety. For example, the engineered CARs may be introduced into T cells using retroviruses, which efficiently and stably integrate a nucleic acid sequence encoding the chimeric antigen receptor into the target cell genome. An exemplary method using lentiviral vectors is described in the Examples section which follows.

The CARs can be encoded by a vector and/or encompassed in one or more delivery vehicles and formulations as described in detail below.

Other methods known in the art include, but are not limited to, lentiviral transduction, transposon-based systems, direct RNA transfection, and CRISPR/Cas systems (e.g., type I, type II, or type III systems using a suitable Cas protein such Cas3, Cas4, Cas5, Cas5e (or CasD), Cash, Cas6e, Cas6f, Cas7, Cas8a1, Cas8a2, Cas8b, Cas8c, Cas9, Cas10, Cas1 Od, CasF, CasG, CasH, Csy1, Csy2, Csy3, Cse1 (or CasA), Cse2 (or CasB), Cse3 (or CasE), Cse4 (or CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3,Csx17, Csx14, Csx10, Csx16, CsaX, Csx3, Csz1, Csx15, Csf1, Csf2, Csf3, Csf4, and Cu1966, etc.).

Vectors can include, for example, origins of replication, scaffold attachment regions (SARs), and/or markers. A marker gene can confer a selectable phenotype on a host cell. For example, a marker can confer biocide resistance, such as resistance to an antibiotic (e.g., kanamycin, G418, bleomycin, or hygromycin). An expression vector can include a tag sequence designed to facilitate manipulation or detection (e.g., purification or localization) of the expressed polypeptide. Tag sequences, such as green fluorescent protein (GFP), glutathione S-transferase (GST), polyhistidine, c-myc, hemagglutinin, or FLAG™ tag (Kodak, New Haven, CT) sequences typically are expressed as a fusion with the encoded polypeptide. Such tags can be inserted anywhere within the polypeptide, including at either the carboxyl or amino terminus. Another example is the EGFRt reporter and the self-cleavableT2A sequence which is cleaved to produce a CAR lacking the EGFRt protein. In some embodiments, the EGFRt is not required.

Additional expression vectors also can include, for example, segments of chromosomal, non-chromosomal and synthetic DNA sequences. Suitable vectors include derivatives of SV40 and known bacterial plasmids, e.g., *E. coli* plasmids col E1, pCR1, pBR322, pMal-C2, pET, pGEX, pMB9 and their derivatives, plasmids such as RP4; phage DNAs, e.g., the numerous derivatives of phage 1, e.g., NM989, and other phage DNA, e.g., M13 and filamentous single stranded phage DNA; yeast plasmids such as the 2μ plasmid or derivatives thereof, vectors useful in eukaryotic cells, such as vectors useful in insect or mammalian cells; vectors derived from combinations of plasmids and phage DNAs, such as plasmids that have been modified to employ phage DNA or other expression control sequences.

Several delivery methods may be utilized in conjunction with the isolated nucleic acid sequences for in vitro (cell cultures) and in vivo (animals and patients) systems. In one embodiment, a lentiviral gene delivery system may be utilized. Such a system offers stable, long term presence of the gene in dividing and non-dividing cells with broad tropism and the capacity for large DNA inserts. (Dull et al, *J Virol,* 72:8463-8471 1998). In an embodiment, adeno-associated virus (AAV) may be utilized as a delivery method. AAV is a non-pathogenic, single-stranded DNA virus that has been actively employed in recent years for delivering therapeutic gene in in vitro and in vivo systems (Choi et al, *Curr Gene Ther,* 5:299-310, 2005). AAV include serotypes 1 through 9. An example of non-viral delivery method may utilize nanoparticle technology. This platform has demonstrated utility as a pharmaceutical in vivo. Nanotechnology has improved transcytosis of drugs across tight epithelial and endothelial barriers. It offers targeted delivery of its payload to cells and tissues in a specific manner (Allen and Cullis, *Science,* 303:1818-1822, 1998).

The vector can also include a regulatory region. The term "regulatory region" refers to nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' non-translated regions (UTRs), transcriptional start sites, termination sequences, polyadenylation sequences, nuclear localization signals, and introns.

The term "operably linked" refers to positioning of a regulatory region and a sequence to be transcribed in a nucleic acid so as to influence transcription or translation of such a sequence. For example, to bring a coding sequence under the control of a promoter, the translation initiation site of the translational reading frame of the polypeptide is typically positioned between one and about fifty nucleotides downstream of the promoter. A promoter can, however, be positioned as much as about 5,000 nucleotides upstream of the translation initiation site or about 2,000 nucleotides upstream of the transcription start site. A promoter typically comprises at least a core (basal) promoter. A promoter also may include at least one control element, such as an enhancer sequence, an upstream element or an upstream activation region (UAR). The choice of promoters to be included depends upon several factors, including, but not limited to, efficiency, selectability, inducibility, desired expression level, and cell- or tissue-preferential expression. It is a routine matter for one of skill in the art to modulate the expression of a coding sequence by appropriately selecting and positioning promoters and other regulatory regions relative to the coding sequence.

Vectors include, for example, viral vectors (such as adenoviruses Ad, AAV, lentivirus, and vesicular stomatitis virus (VSV) and retroviruses), liposomes and other lipid-containing complexes, and other macromolecular complexes capable of mediating delivery of a polynucleotide to a host cell. Vectors can also comprise other components or functionalities that further modulate gene delivery and/or gene expression, or that otherwise provide beneficial properties to the targeted cells. As described and illustrated in more detail below, such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. Other vectors include those described by Chen et al; *BioTechniques*, 34: 167-171 (2003). A large variety of such vectors are known in the art and are generally available. A "recombinant viral vector" refers to a viral vector comprising one or more heterologous gene products or sequences. Since many viral vectors exhibit size-constraints associated with packaging, the heterologous gene products or sequences are typically introduced by replacing one or more portions of the viral genome. Such viruses may become replication-defective, requiring the deleted function(s) to be provided in trans during viral replication and encapsidation (by using, e.g., a helper virus or a packaging cell line carrying gene products necessary for replication and/or encapsidation). Modified viral vectors in which a polynucleotide to be delivered is carried on the outside of the viral particle have also been described (see, e.g., Curiel, D T, et al. *PNAS* 88: 8850-8854, 1991).

Additional vectors include viral vectors, fusion proteins and chemical conjugates. Retroviral vectors include Moloney murine leukemia viruses and HIV-based viruses. One HIV based viral vector comprises at least two vectors wherein the gag and pol genes are from an HIV genome and the env gene is from another virus. DNA viral vectors include pox vectors such as orthopox or avipox vectors, herpesvirus vectors such as a herpes simplex I virus (HSV) vector [Geller, A. I. et al., *J. Neurochem*, 64: 487 (1995); Lim, F., et al., in DNA Cloning: Mammalian Systems, D. Glover, Ed. (Oxford Univ. Press, Oxford England) (1995); Geller, A. I. et al., *Proc Natl. Acad. Sci.*: U.S.A.:90 7603 (1993); Geller, A. I., et al., *Proc Natl. Acad. Sci USA*: 87:1149 (1990)], Adenovirus Vectors [LeGal LaSalle et al., *Science*, 259:988 (1993); Davidson, et al., *Nat. Genet.* 3: 219 (1993); Yang, et al., *J. Virol.* 69: 2004 (1995)] and Adeno-associated Virus Vectors [Kaplitt, M. G., et al., *Nat. Genet.* 8:148 (1994)].

The polynucleotides embodied herein may be used with a microdelivery vehicle such as cationic liposomes and adenoviral vectors. For a review of the procedures for liposome preparation, targeting and delivery of contents, see Mannino and Gould-Fogerite, *Bio Techniques*, 6:682 (1988). See also, Felgner and Holm, *Bethesda Res. Lab. Focus*, 11(2):21 (1989) and Maurer, R. A., *Bethesda Res. Lab. Focus*, 11(2): 25 (1989).

Replication-defective recombinant adenoviral vectors, can be produced in accordance with known techniques. See, Quantin, et al., *Proc. Natl. Acad. Sci. USA*, 89:2581-2584 (1992); Stratford-Perricadet, et al., *J. Clin. Invest.*, 90:626-630 (1992); and Rosenfeld, et al., *Cell*, 68:143-155 (1992).

Another method is to use single stranded DNA producing vectors which can produce the expressed products intracellularly. See for example, Chen et al, *BioTechniques*, 34: 167-171 (2003), which is incorporated herein, by reference, in its entirety.

The nucleic acid sequences of the invention can be delivered to an appropriate cell of a subject. This can be achieved by, for example, the use of a polymeric, biodegradable microparticle or microcapsule delivery vehicle, sized to optimize phagocytosis by phagocytic cells such as macrophages. For example, PLGA (poly-lacto-co-glycolide) microparticles approximately 1-10 µm in diameter can be used. The polynucleotide is encapsulated in these microparticles, which are taken up by macrophages and gradually biodegraded within the cell, thereby releasing the polynucleotide. Once released, the DNA is expressed within the cell. A second type of microparticle is intended not to be taken up directly by cells, but rather to serve primarily as a slow-release reservoir of nucleic acid that is taken up by cells only upon release from the micro-particle through biodegradation. These polymeric particles should therefore be large enough to preclude phagocytosis (i.e., larger than 5 µm and preferably larger than 20 µm). Another way to achieve uptake of the nucleic acid is using liposomes, prepared by standard methods. The nucleic acids can be incorporated alone into these delivery vehicles or co-incorporated with cell- or tissue-specific antibodies, for example, specific for Treg cells or delivery to tumor cells as a target. Alternatively, one can prepare a molecular complex composed of a plasmid or other vector attached to poly-L-lysine by electrostatic or covalent forces. Poly-L-lysine binds to a ligand that can bind to a receptor on target cells. Delivery of "naked DNA" (i.e., without a delivery vehicle) to an intramuscular, intradermal, or subcutaneous site, is another means to achieve in vivo expression. In the relevant polynucleotides (e.g., expression vectors) the nucleic acid sequence encoding an isolated nucleic acid sequence comprising a sequence encoding a CAR, as described above.

In some embodiments, the compositions of the invention can be formulated as a nanoparticle, for example, nanoparticles comprised of a core of high molecular weight linear polyethylenimine (LPEI) complexed with DNA and surrounded by a shell of polyethyleneglycol modified (PEGylated) low molecular weight LPEI. The nucleic acids and vectors may also be applied to a surface of a device (e.g., a catheter) or contained within a pump, patch, or other drug delivery device. The nucleic acids and vectors disclosed herein can be administered alone, or in a mixture, in the presence of a pharmaceutically acceptable excipient or carrier (e.g., physiological saline). The excipient or carrier is selected on the basis of the mode and route of administration. Suitable pharmaceutical carriers, as well as pharmaceutical necessities for use in pharmaceutical formulations, are described in *Remington's Pharmaceutical Sciences* (E.

W. Martin), a well-known reference text in this field, and in the USP/NF (United States Pharmacopeia and the National Formulary).

In some embodiments, the compositions can be formulated as a nanoparticle encapsulating the compositions embodied herein.

Regardless of whether compositions are administered as nucleic acids or polypeptides, they are formulated in such a way as to promote uptake by the mammalian cell. Useful vector systems and formulations are described above. In some embodiments the vector can deliver the compositions to a specific cell type. The invention is not so limited however, and other methods of DNA delivery such as chemical transfection, using, for example calcium phosphate, DEAE dextran, liposomes, lipoplexes, surfactants, and perfluoro chemical liquids are also contemplated, as are physical delivery methods, such as electroporation, micro injection, ballistic particles, and "gene gun" systems.

In other embodiments, the compositions comprise a cell which has been transformed or transfected with one or more vectors or nucleic acids encoding one or more CARs. In some embodiments, the methods of the invention can be applied ex vivo. That is, a subject's cells can be removed from the body and transduced with the compositions in culture with a desired target antigen, expand target-antigen specific, e.g. T cells and the expanded cells returned to the subject's body. The cell can be the subject's cells or they can be haplotype matched or a cell line. The cells can be irradiated to prevent replication. In some embodiments, the cells are human leukocyte antigen (HLA)-matched, autologous, cell lines, or combinations thereof. In other embodiments the cells can be a stem cell. For example, an embryonic stem cell or an artificial pluripotent stem cell (induced pluripotent stem cell (iPS cell)). Embryonic stem cells (ES cells) and artificial pluripotent stem cells (induced pluripotent stem cell, iPS cells) have been established from many animal species, including humans. These types of pluripotent stem cells would be the most useful source of cells for regenerative medicine because these cells are capable of differentiation into almost all of the organs by appropriate induction of their differentiation, with retaining their ability of actively dividing while maintaining their pluripotency. iPS cells, in particular, can be established from self-derived somatic cells, and therefore are not likely to cause ethical and social issues, in comparison with ES cells which are produced by destruction of embryos. Further, iPS cells, which are self-derived cell, make it possible to avoid rejection reactions, which are the biggest obstacle to regenerative medicine or transplantation therapy.

The CARs can be easily delivered to a subject by methods known in the art, for example, methods which deliver siRNA. Thus, the, CAR molecules can be used clinically, similar to the approaches taken by current gene therapy. In particular, a CAR stable expression stem cell or iPS cells for cell transplantation therapy as well as vaccination can be developed for use in subjects.

The CAR-T cells, once they have been expanded ex vivo can be reinfused into the subject in a therapeutically effective amount. In one embodiment, the CAR-T cells are stimulated using anti-CD3/CD28 beads for their in vitro expansion. CAR-T cells can be used in response to an autoimmune disease antigen (e.g., citrullinated vimentin (CV)). The term "therapeutically effective amount" as used herein means the amount of CAR T cells when administered to a mammal, in particular a human, in need of such treatment, is sufficient to treat autoimmune diseases such as rheumatoid arthritis.

The precise amount of CAR T cells to be administered can be determined by a physician with consideration of individual differences in age, weight, extent of disease and condition of the subject.

Typically, administration of T cell therapies is defined by number of cells per kilogram of body weight. However, because T cells will replicate and expand after transfer, the administered cell dose will not resemble the final steady-state number of cells.

In an embodiment, a pharmaceutical composition comprising the CAR T cells of the present invention may be administered at a dosage of $10^4$ to $10^9$ cells/kg body weight. In another embodiment, a pharmaceutical composition comprising the CAR T cells of the present invention may be administered at a dosage of $10^5$ to $10^6$ cells/kg body weight, including all integer values within those ranges.

Compositions comprising the CAR T cells of the present invention may also be administered multiple times at these dosages. The cells can be administered by using infusion techniques that are known in the art (see, for example, Rosenberg et al., 1988, *New England Journal of Medicine*, 319: 1676). The optimal dosage and treatment regimen for a particular subject can be readily determined by one skilled in the art by monitoring the patient for signs of disease and adjusting the treatment accordingly.

In certain embodiments, administration of any of the compositions embodied herein, e.g. a CV-CAR T cell, for the treatment of an autoimmune disease, can be combined with other cell-based therapies, for example, stem cells, antigen presenting cells, etc.

The composition of the present invention may be prepared in a manner known in the art and are those suitable for parenteral administration to mammals, particularly humans, comprising a therapeutically effective amount of the composition alone, with one or more pharmaceutically acceptable carriers or diluents.

The term "pharmaceutically acceptable carrier" as used herein means any suitable carriers, diluents or excipients. These include all aqueous and non-aqueous isotonic sterile injection solutions which may contain anti-oxidants, buffers and solutes, which render the composition isotonic with the blood of the intended recipient; aqueous and non-aqueous sterile suspensions, which may include suspending agents and thickening agents, dispersion media, antifungal and antibacterial agents, isotonic and absorption agents and the like. It will be understood that compositions of the invention may also include other supplementary physiologically active agents.

The carrier must be pharmaceutically "acceptable" in the sense of being compatible with the other ingredients of the composition and not injurious to the subject. Compositions include those suitable for parenteral administration, including subcutaneous, intramuscular, intraarticular, intravenous and intradermal administration. The compositions may conveniently be presented in unit dosage form and may be prepared by any method well known in the art of pharmacy. Such methods include preparing the carrier for association with the CAR T cells. In general, the compositions are prepared by uniformly and intimately bringing into association any active ingredients with liquid carriers.

In an embodiment, the composition is suitable for parenteral administration. In another embodiment, the composition is suitable for intravenous administration. In another embodiment, the composition is suitable for intraarticular administration.

Compositions suitable for parenteral administration include aqueous and nonaqueous isotonic sterile injection solutions which may contain anti-oxidants, buffers, bactericides and solutes, which render the composition isotonic with the blood of the intended recipient; and aqueous and non-aqueous sterile suspensions which may include suspending agents and thickening agents.

The invention also contemplates the combination of the composition of the present invention with other drugs and/or in addition to other treatment regimens or modalities such as surgery. When the composition of the present invention is used in combination with known therapeutic agents the combination may be administered either in sequence (either continuously or broken up by periods of no treatment) or concurrently or as an admixture. In the case of autoimmune diseases, e.g. rheumatoid arthritis, treatment comprises administering to the subject the compositions embodied herein, e.g. autologous T cells transduced with CAR specific for citrullinated-vimentin (CV) and one or more anti-inflammatory agents and/or therapeutic agents. The anti-inflammatory agents comprise one or more antibodies which specifically bind to pro-inflammatory cytokines, e.g. pro-inflammatory cytokines such as IL-1, TNF, IL-6, GM-CSF, and IFN-γ. In certain embodiments, the antibodies are anti-TNFα, anti-IL-6 or combinations thereof. In certain embodiments, one or more agents, other than antibodies can be administered which decrease pro-inflammatory cytokines, e.g. non-steroidal anti-inflammatory drugs (NSAIDs). Any combination of antibodies and one or more agents can be administered which decrease pro-inflammatory cytokines.

Treatment in combination is also contemplated to encompass the treatment with either the composition of the invention followed by a known treatment, or treatment with a known agent followed by treatment with the composition of the invention, for example, as maintenance therapy. For example, in the treatment of autoimmune diseases, excessive and prolonged activation of immune cells, such as T and B lymphocytes, and overexpression of the master pro-inflammatory cytokine tumor necrosis factor alpha (TNF), together with other mediators such as interlukin-6 (IL-6), interlukin-1 (IL-1), and interferon gamma (IFN-γ), play a central role in the pathogenesis of autoimmune inflammatory responses in rheumatoid arthritis (RA), inflammatory bowel disease (IBD), Crohn's disease (CD), and ankylosing spondylitis (AS).

Non-steroidal anti-inflammatory drugs (NSAIDs), glucocorticoids, disease-modifying anti-rheumatic drugs (DMARDs) are traditionally used in the treatment of autoimmune inflammatory diseases. NSAIDs and glucocorticoids are effective in the alleviation of pain and inhibition of inflammation, while DMARDs have the capacity of reducing tissue and organ damage caused by inflammatory responses. More recently, treatment for RA and other autoimmune diseases has been revolutionized with the discovery that TNF is critically important in the development of the diseases. Anti-TNF biologics (such as infliximab, adalimumab, etanercept, golimumab, and certolizumab pepol) have markedly improved the outcome of the management of autoimmune inflammatory diseases.

Non-steroidal anti-inflammatory drugs have the analgesic, antipyretic, and anti-inflammatory effect, frequently used for the treatment of conditions like arthritis and headaches. NSAIDs relieve pain through blocking cyclooxygenase (COX) enzymes. COX promotes the production of prostaglandins, a mediator which causes inflammation and pain. Although NSAIDs have different chemical structures, all of them have the similar therapeutic effect, e.g., inhibition of autoimmune inflammatory responses. In general, NSAIDs can be divided into two broad categories: traditional non-selective NSAIDs and selective cyclooxygenase-2 (COX-2) inhibitors (For a review see, P. Li et al. *Front Pharmacol.* 2017; 8: 460).

In addition to anti-TNF agents, the biologics targeting other proinflammatory cytokines or immune competent molecules have also been extensively studied and actively developed. For example, abatacept, a fully humanized fusion protein of extracellular domain of CTLA-4 and Fc fraction of IgG1, has been approved for the RA patients with inadequate response to anti-TNF therapy. The major immunological mechanism of abatacept is selective inhibition of co-stimulation pathway (CD80 and CD86) and activation of T cells. Tocilizumab, a humanized anti-IL-6 receptor monoclonal antibody was approved for RA patients intolerant to DMARDs and/or anti-TNF biologics. This therapeutic mAb blocks the transmembrane signaling of IL-6 through binding with soluble and membrane forms of IL-6 receptor. Biological drugs targeting IL-1 (anakinra), Th1 immune responses (IL-12/IL-23, ustekinumab), Th17 immune responses (IL-17, secukinumab) and CD20 (rituximab) have also been approved for the treatment of autoimmune diseases (For a review see, P. Li et al. *Front Pharmacol.* 2017; 8: 460).

Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Example 1: Generation of Lentiviral Vectors Expressing CV-CAR

Different elements that play an important role in the effectiveness of the CAR were assessed. Thus, in some embodiments, three different versions of the scFv were compared, two lengths of a hinge were assessed, and two different co-stimulatory domains were analyzed. At each of these steps, one of the CV-CAR candidates, which provided the best T cell activation profile, was selected.

Generation of CV-specific scFv: The variable regions of the heavy and light chain of the BVCA1 antibody were sequenced and used to generate CV-specific scFv gene in a $V_H$-linker-$V_L$ format. The scFv protein was produced by inserting the sequence into a pSYN plasmid and inoculated into DH5-alpha *E. coli* competent cells. A single colony was grown in 5 ml of 2YT medium supplemented with 2% glucose and 100 µg/ml of ampicillin overnight at 30° C. in a shaker. The 5 ml of O/N culture was inoculated into 500 ml fresh 2YT medium (with 0.1% glucose and 100 µg/ml of ampicillin) and incubated at 37° C. for 2.5 hours until $OD_{600}$=0.9. Expression of the scFv was induced by adding 250 µl of Isopropyl-β-d-thiogalactopyranoside (IPTG) and then incubate at 30° C. for 4 hrs with shaking. After 20 min of centrifugation at 5000 rpm, the bacterial pellet was re-suspended with 12.5 ml ice cold Periplasmic extraction buffer (PPB, 200 g/L Sucrose,30 mM Tris-HCl, pH 8.0) and kept on ice O/N. The next day bacteria were centrifuged at 10,000 rpm for 30 min, the supernatant was kept, and the pellet re-suspended with 12.5 ml of 5 mM ice cold $Mg_2SO_4$ and kept on ice for 30 min to induce an osmotic shock. The lysed bacteria were centrifuged at 10,000 rpm for 30 min and the supernatant was combined with the previous one. The CV-specific scFv was then purified by Ni-NTA chromatography.

Assessment of the binding specificity and affinity of BVCA1 antibodies and scFv to CV peptide: The binding specificity of BVCA1 IgG and scFv were assessed by ELISA. 96-well ELISA plates were coated O/N at 4° C. with 50 μl Streptavidin at 10m/ml. Wells were washed three times and blocked with 2000 of 1×PBS 1% BSA for 1 h at RT and washed again. 1000 of biotinylated peptides at 10 ug/ml diluted in PBS 1% BSA were added and incubated for 1 h at RT. Wells were then washed three times. 1000 of BVCA1 IgG or scFv or isotype control were added at various concentrations (serial dilution). After 1.5h of incubation at RT, wells were washed 3 times and the appropriate secondary antibody-conjugated to Alkaline Phosphatase (AP) was added to the wells: for fully human BVCA1 IgG, a Goat anti-Human IgG Ab-AP (Life Technologies #62-8422) was used at 1/5000 dilution, for the chimeric version of the BVCA1 Ab with mouse IgG2a CH2 and CH3 domains, a Goat Anti-Mouse IgG (whole molecule) Ab-AP (Sigma #A3562) was used at 1/10000 dilution, for the scFv for of BVCA1, anti-c-Myc Ab (clone 9E10, mouse IgG1; Santa Cruz Biotech, sc-40) was used at 1/200 dilution followed by an anti-mouse IgG-AP (Sigma, A3562) at 1/10 000 dilution. Wells were washed three times and 100 μl of Step pNPP substrate solution was added. Reaction was stopped with 50 11.1 of NaOH 3M after 15 to 30 min and absorbance was read in a microplate reader at 405 nm. Kinetics and affinities of BVCA1 Ig and scFv to CV peptide were analyzed by surface plasmon resonance using Biacore T100 (GE healthcare). Biotinylated CV peptide was immobilized on a streptavidin-coated sensor chip (CM5). Varying concentrations of antibodies were injected at a flow rate of 30 μl/min.

Figure 10A:
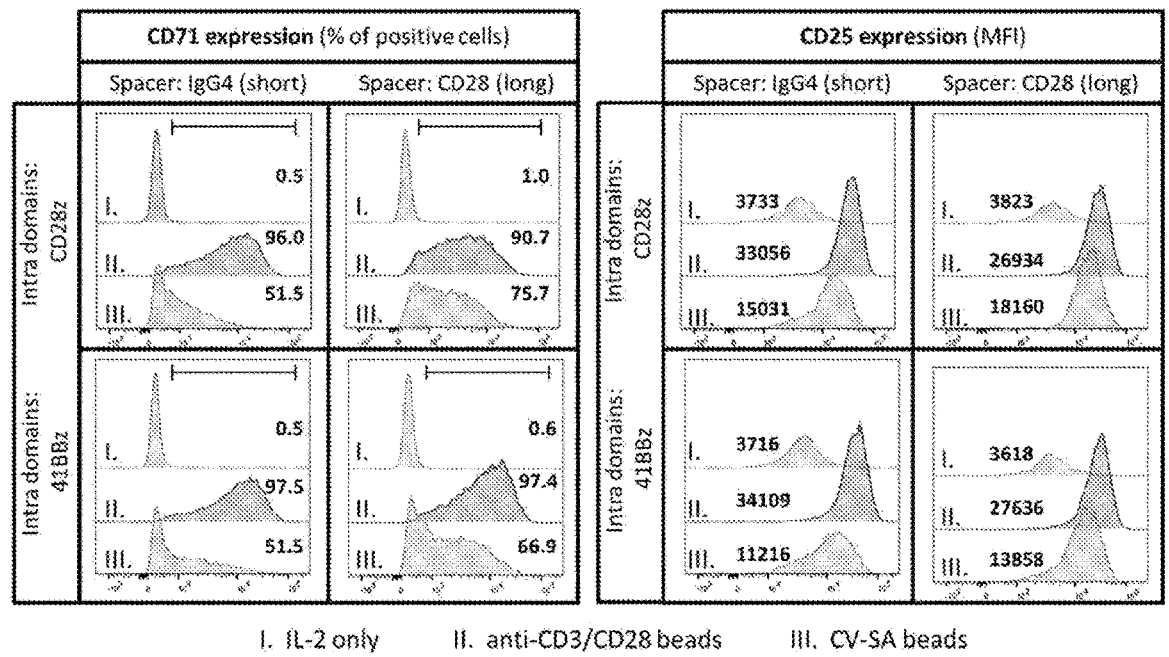
FIGS. 10A-10B. Analysis of different lengths hinges of CAR constructs. At day 5 after transduction CV-CAR$^+$ Tregs were sorted by flow cytometry based on the expression of EGFRt. Sorted CV-CAR Tregs were then re-stimulated in presence or absence of anti-CD3/CD28 beads or CV-peptide/streptavidin (CV-pep-SA) beads.
Figure 10B:
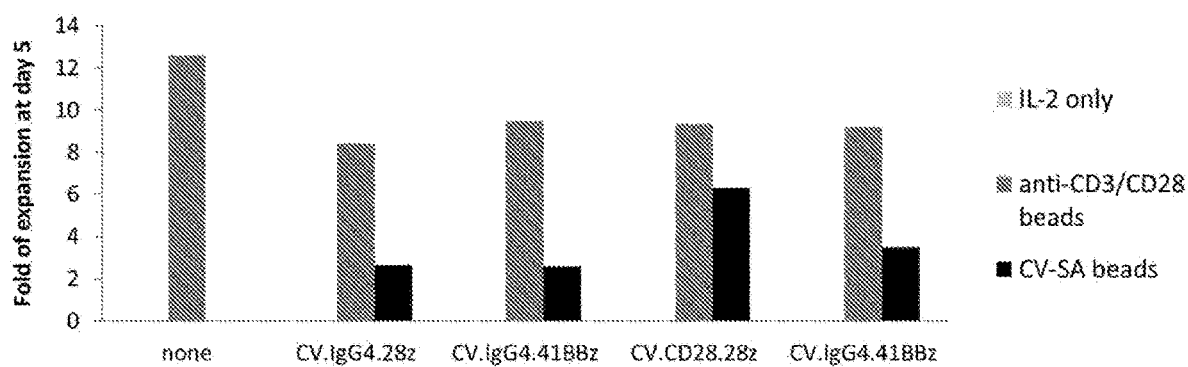

Generation of CV-specific CAR constructs: By using Gibson assembly method (Gibson Assembly Master Mix, BioLabs, according to the manufacturer's instructions) the anti-CD19 scFv sequence was replaced by the CV-specific scFv sequence into already existing 19-CAR constructs cloned in p10001 lentiviral plasmid with rather CD28z or 41BBz intracellular domains followed by a CD3ζ domain and a truncated version of EGFR (EGFRt) used as a receptor and separated from the CAR by a T2A domain (CAR constructs were provided by Juno Therapeutics). These CAR constructs were both with a short hinge (IgG4-36 bp) so the Gibson assembly method was again used to replace the short hinge by a long hinge (117 bp of the extracellular domain of human CD28 sequence). Thus, multiple CV-specific CAR constructs were generated with a short or long hinge and 41BB or CD28 co-stimulatory domains.

HEK 293T cells transfection and lentivirus particles titration: HEK 293T cells were plated at 800,000 cells per well in a 6-well plate with 2 ml DMEM high glucose media supplemented with 10% FBS (without antibiotics) and placed at 37° C. 5% $CO_2$ overnight. At 80% of confluence in the wells, a mix of 1.5 ug of CV-CAR p10001 with 1.33 ug of packaging vector p8.91, 0.168 μg of VSV envelope vector pMD2.G and 9 μg of FuGENE HD Transfection Reagent (Promega) was gently added drop by drop to each well. To improve the efficiency of the viral particle production, the media was replaced after 14 hours by fresh 10% FBS-DMEM high glucose media supplemented with ViralBoost Reagent (diluted at 1/500; VC-100, Alstem). The virus supernatant was harvested 2 days later and concentrated 100 folds using a lentivirus precipitation solution (VP100, Alstem, manufacturer's instructions were followed). The transfection efficiency of the HEK 293T cells was assessed by flow cytometry using an anti-EGFRt Ab (Erbitux, Juno Therapeutics). To titer the lentiviral particles, Jurkat cells (10,000/well in 96-well plate) were place in culture with a serial dilution of virus for 4 days, then stained with anti-EGFRt Ab and analyzed by flow cytometry (LSR II; BD Biosciences). The dilutions yielding 1% to 20% of positive cells were used to determine the virus titer by following this equation: [number of target cells×(% of EGFRt cells/100)]/Volume of supernatant (ml).

FIG. 19 shows assessment of the CV-specific CAR expression at the cell surface of the HEK 293T cells at day 3 after transfection. The techniques that were used for HEK 293T cells transfection and lentivirus particles titration are described above.

Example 2: Generation of Lentiviral Vectors Expressing CV-CAR

CV-CAR construct generation: To generate a CV-CAR construct expressed in a lentiviral vector, a single-chain variable fragment (scFv) of a CD19-CAR construct present in a lentiviral backbone plasmid p10001 (available from Juno Therapeutics, Inc.) was replaced by a BVCA1 scFv using Gibson assembly method (FIGS. 8A and 8B). As only a few differences are observed between the amino acid sequences of human and murine vimentin, the anti-CV antibody shows high specificity for both human and murine peptides. This allows performing the assessment both on human samples in vitro and on an RA mouse model in vivo. FIG. 6, illustrating the alignment of portions of human vimentin peptide and murine vimentin peptide, explains why BVCA1 monoclonal antibody is specific for both human and murine citrullinated vimentin. FIG. 7 demonstrates the assessment of the specificity of the anti-CV antibody (BVCA1). FIG. 4 shows the assessment of the specificity and affinity for CV of the single-chain variable fragment (scFv) synthesized from BVCA1 antibody. FIG. 5 shows that (FIG. 5A) the dissociation constant ($K_D$) between the BVCA1 fully human IgG and the human CV peptide is about 10 nM, and that (FIG. 5B) $K_D$ between the BVCA1 scFv and the human CV peptide is about 198 nM. The results show that, as BVCA1 antibody, BVCA1 scFv is specific for citrullinated vimentin.

As shown in FIG. 8B, two versions of the CV-specific CAR were created, each containing CD3ζ plus either CD28 (CV.28z-CAR) or 41BB (CV.41BBz-CAR) co-stimulatory domains. The CV-CAR construct in accordance with the described embodiments can have any suitable type(s) of co-stimulatory domains. A truncated version of EGFR gene separated from the CAR by a T2A peptide was used as a reporter gene. Lentiviral particles were produced by transfecting HEK 293 T cells. The supernatant was collected at day 3 and viral particles were precipitated to be enriched.

FIG. 9 illustrates an example of a timeline of generation of CV-CAR constructs and subsequent assessment of the generated constructs. Details and examples of the various steps of the construct generation and assessment are described throughout this disclosure.

Assessment of CV-CAR construct hinges of different lengths: The constructs having hinges of two different lengths were compared: (1) a short hinge derived from IgG4 motif, and (2) a long hinge that is a portion of the extracellular domain of human CD28. It was observed that, for both CV.28z-CAR and CV.41BBz-CAR, the presence of the long hinge induced a more efficient activation of the CV-CAR T cells. Depending of the target antigen of the CAR construct, the optimal length of the hinge can be determined to allow a proper antigen-binding. To assess which length of hinge was optimal for the CV-specific CAR Treg activation, two different hinges were compared—a short hinge, IgG4 (36 bp) and a long hinge created using a portion of the extracellular domain of human CD28 (117 bp). To study these two different hinges in both CV-CAR with CD28z intracellular domain and CV-CAR with 41BBz intracellular domain, four versions of the CV-CAR construct were generated: two with the short hinge (CV-IgG4-28z and CV-IgG4-41BBz) and two with the long hinge (CV-CD28-28z and CV-CD28-41BBz). Expression of these different CV-CAR constructs into Tregs was induced by lentiviral transduction and the activation profile of the CV-CAR Tregs after being re-stimulated in presence CV-SA beads was analyzed. As shown in FIG. 10A, at day 3, a higher percentage of cells expressed the activation marker CD71 in the populations of CV-CAR Tregs expressing a CAR construct with the long hinge compared to the ones with the short hinge. The same observation can be made when assessing CD25 mean fluorescence intensity (MFI) at day 3. Moreover, the CV-CAR Tregs with the long hinge expanded more efficiently than the one with the short hinge (FIG. 10B).

Assessment of different versions of the scFv: The inventors developed a novel scFv, BVCA1, that binds specifically citrullinated vimentin protein. Most of the antibodies targeting citrullinated proteins found in RA patients are less specific and cross-react with a multitude of citrullinated proteins. Thus, the further analysis used BVCA1. However, from this single IgG, three versions of scFv were generated: (1) one with the $V_L$ and $V_H$ chains with the nucleotide sequence of origin with a 24 amino acid linker (scFv #1), (2) one with the nucleotide sequence of origin and a $(GGGGS)_3$ linker (scFv #2,) and (3) a third one with a codon-optimized sequence of $V_L$ and $V_H$ chains with a $(GGGGS)_3$ linker (scFv #3).

Figure 11A:
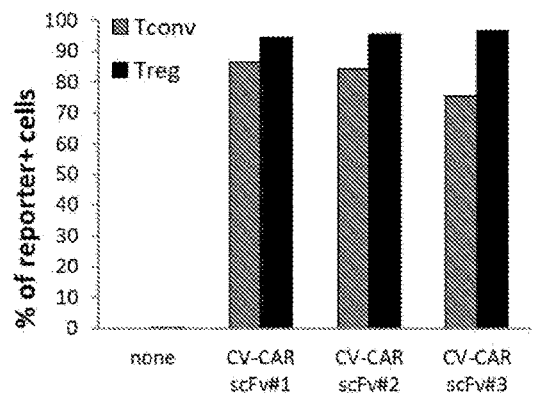
FIGS. 11A-11D. Comparative analysis of CV-CAR constructs with different version of the BVCA1 scFv. Tconv and Treg cells were transduced with different versions of the CV-CAR construct at day 2 after stimulation. The transduction efficiency was assessed by flow cytometry. The percentages of cells expressing the CAR-reporter gene (FIG. 11A) and the CV-CAR (FIG. 11B) at the cell surface are shown. Two days after a second round of stimulation in presence of different stimulatory conditions (IL-2 only, anti-CD3/CD28 beads and CV-SA beads), the expression of the activation markers CD69 and CD71 was analyzed by flow cytometry (FIGS. 11C and 11D)
Figure 11B:
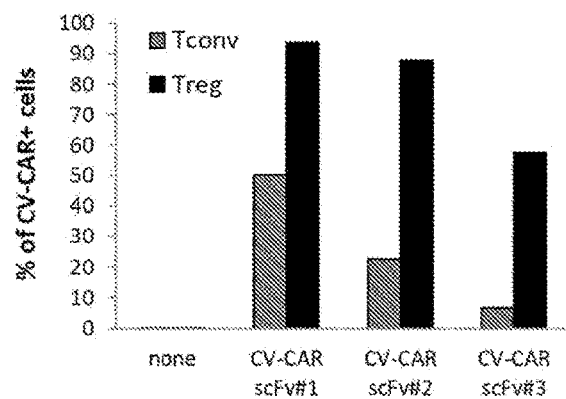
Figure 11C:
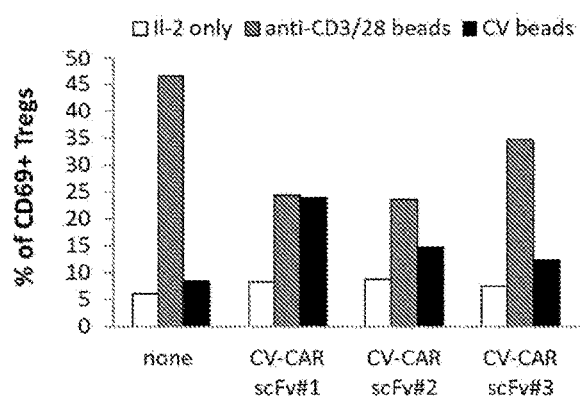
Figure 11D:
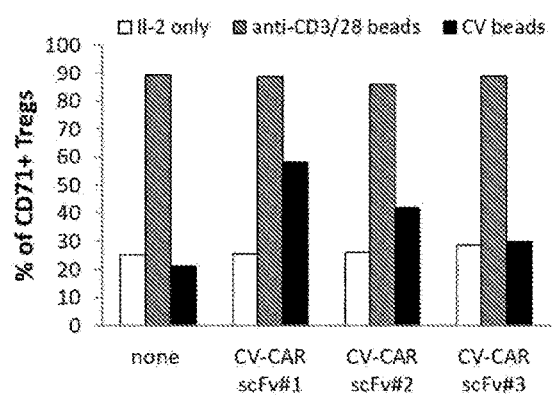

As shown in FIGS. 11A-11D, only the CV-CAR with the scFv #1 was efficiently expressed at the cells surface of the Tregs and T cony at day 3 after transduction, whereas the expression of the reporter gene suggested a transduction efficacy comparable between the 3 different CAR constructs (FIGS. 11A and 11B). At day 2 after re-stimulation in presence of CV-pep-SA beads (CV beads), a higher percentage of cells expressing the activation markers CD71 and CD69 in the Treg population previously transduced with the CV-CAR scFv #1 was observed, compared with the two other groups of CV-CAR Tregs (FIGS. 11C and 11D). Based on these results, the CV-CAR construct with the scFv #1 was selected to continue the development of the CV-CAR constructs.

Example 3: Generation of CV-CAR-Transduced Human Tregs and Tconv

Samples, cell sorting and in vitro stimulation: Fresh whole blood units were obtained from healthy blood donors recruited from the general population at the University of California, San Francisco or provided by StemCell Technologies. PBMCs were isolated by density gradient sedimentation using Ficoll Paque medium (GE healthcare). $CD4^+$ T cells were enriched by positive selection from PBMCs by magnetic cell sorting (Miltenyi Biotec). $CD4^+$ T cells were then stained with fluorochrome-labeled mAb specific for CD4, CD25 and CD127 and separated by flow cytometry (FACSAria; BD Biosciences) into two subsets: $CD4^+CD25^+CD127"$ ($CD4^+$ regulatory T cells; Tregs) and $CD4^+CD25^-CD127^+$ ($CD4^+$ T conventional cells; Tconv) at a purity higher than 97%. Sorted cell populations were then stimulated with anti-CD3/anti-CD28-coated Dynabeads (ThermoFisher Scientific) at ratio 1:1 for Tconv and 1 cells for 2 beads for Tregs in presence of interleukin-2 (IL-2; Proleukin, Prometheus Laboratories; 100U/ml for Tconv and 300 U/ml for Tregs) in T cell media: RPMI 1640 media supplemented with 5mMHEPES, 2 mM L-glutamine, 50 mg/ml each penicillin/streptomycin (Invitrogen, Carlsbad, CA), 5 mM nonessential amino acids, 5 mM sodium pyruvate (Mediatech), and 10% FBS (Invitrogen). Fresh media containing IL-2 was added every 2 days and cells were split when needed.

Lentiviral transduction of the Tconv and Treg populations and transduction efficiency assessment: At day 2 after stimulation of the sorted $CD4^+$ populations, cells were counted and seeded into 250,000 to 500,000 cells per well into a 24-well plate and placed at 37° C. for at least 1 hour in the incubator. A mix of viral particles and protamine sulfate (100 µg/ml) was then added to the wells to reach a multiplicity of infection (MOI) of 1 particle per cell. The cells were then spinoculated for 30 minutes at 1200×g at 32° C. The plate was then placed back at 37° C. for 90 minutes. The cells were spin down for 5 min and the inoculum media was replace by a fresh one containing IL-2. Three days later, the efficiency of the transduction was determined by flow cytometry using the anti-EGFRt Ab. To confirm that the percentage of $EGFRt^+$ cells was representative of the expression of the CAR at the cell surface of these cells, the cells were co-stained with EGFRt Ab-conjugated with APC or PE and a CV-Streptavidin(SA)-AF488 tetramer, incubated for 2 hours at 4° C. under agitation and analyzed by flow cytometry at day 4 after transduction. The CV-SA-AF488 complex was made just before the cell staining by co-incubating biotinylated CV peptide (Innovagen) with SA-AF488 conjugated (Life Technologies) at a ratio 1 SA protein for 4 biotinylated peptides for 15 min at 4° C. under agitation and by spinning down the tube at high 14000×g for 5 min.

Results

Using the CV-CAR lentiviral vectors, human T $CD4^+$ regulatory cells (Tregs) and conventional (Tconv) cells were transduced at a ratio 1 virus for 1 cell. These cells were isolated from the peripheral blood of healthy donors (HD), sorted by flow cytometry based on the expression of CD4, CD25 and CD127 (Tregs: $CD4^+CD25^+CD127^-$; Tconv: $CD4^+CD25^-CD127^+$) and stimulated for 2 days with anti-CD3/CD28 beads prior transduction. Cells were also transduced with CD19.28z-CAR and CD19.41BBz-CAR to be used as controls.

Figure 12A:
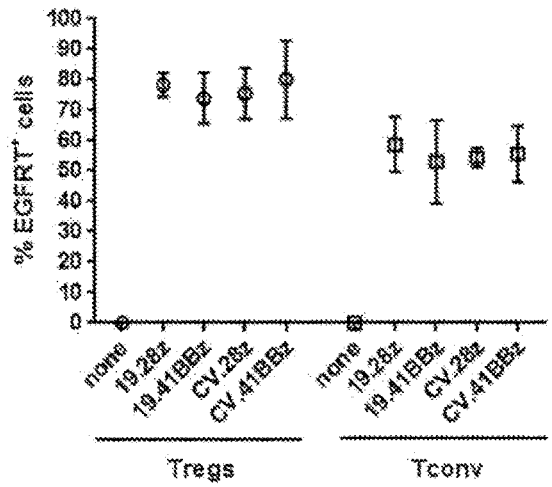
FIGS. 12A-12D. Assessment of surface expression of the reporter EGFRt in Tregs and Tconv.
Figure 12B:
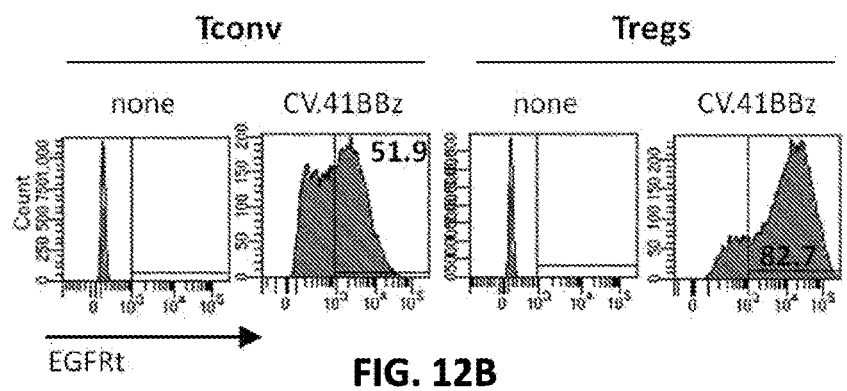
Figure 12C:
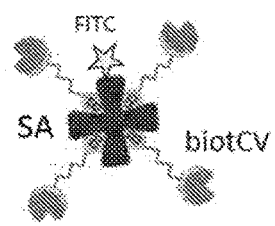
Figure 12D:
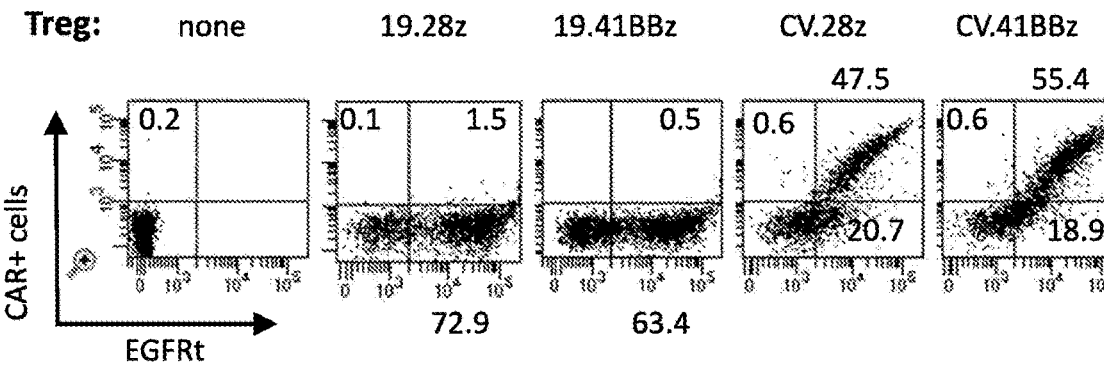

At day 4 after transduction, the percentage of EGFRt cells was determined by using an anti-EGFRt antibody. The data showed that transduction with CV-CAR and CD19-CAR resulted in similar percentages of EGFRt among Tregs and among Tconv populations (FIG. 12A). Moreover, it was observed with all the CARs tested that Tregs were more efficiently transduced than Tconv. Thus, in one experiment, from about 74% to about 80% of Tregs were EGFRt depending on the CAR construct, compared to from about 53 to about 59% in Tconv populations (FIG. 12A). The mean fluorescent intensity (MFI) was also higher in EGFRt Tregs compared to $EGFRt^+$ Tconv, as shown in the example of FIG. 12B To validate that EGFRt expression was representative of the CAR expression at the cell surface and to assess the ability of the CV-CAR constructs to bind their target antigen, the cells were stained with a biotinylated-CV-peptide/Streptavidin tetramer conjugated with FITC (CVpep-SA-FITC) illustrated in FIG. 12C and EGFRt antibody. The data confirmed that EGFRt expression was correlated with CV-CAR expression at the surface of the Tregs and proved that the ability of BVCA1 scFv to bind CV was preserved after insertion in the CV-CAR construct (FIG. 12D). Similar results were obtained with Tconv cells. The results demonstrate that CV-specific CARs expressed at the surface of Tregs specifically bind CV peptide.

Example 4: Analysis of the Effect of CV-CAR Signaling on Tregs Activation and Expansion in Vitro Preparation of the cells for a second round of stimulation: To avoid any residual activation of the cells due to the presence of the anti-CD3/anti-CD28-coated Dynabeads, these beads were removed from the cell cultures at day 7 by using a magnet (ThermoFisher Scientific, according to the manufacturer's instructions). Additionally, when indicated, CAR⁺ Treg and Tconv populations were sorted based on the expression of EGFRt by flow cytometry at day 7.

Re-stimulation of the CV-CAR T cells: At day 9 or 10 after the first stimulation, CAR⁺ T cells were re-stimulated. Different conditions of stimulation were used to compare the activation profiles of the CV-CAR T cells when stimulated through the CAR or through their endogenous TCR. Beads presenting CV peptides were generated by coupling biotinylated-CV peptides (Innovagen) with Dynabeads M-280 Streptavidin (Invitrogen, according to the manufacturer's instructions) referred as CV-SA beads. Cells were re-stimulated in presence of IL-2 (100 U/ml for Tconv and 300 U/ml for Tregs) in absence or presence of anti-CD3/anti-CD28-coated Dynabeads at ratio 1:1 or CV-SA beads at ratio 2 beads for 1 cell. Fresh media containing IL-2 was added every 2 days and cells were split when needed.

Study of the activation profile and expansion of CV-CAR T cells after second round of stimulation: At day one after re-stimulation of the cells, cell clusters were visualized using a bright-field microscope. At days 2 and 3, a small fraction of the cells from each stimulation conditions was harvested and stained with antibodies against CD4, CD25, CD69, CD71, EGFRt and LIVE/DEAD fixable blue stain (Invitrogen) and incubated 20 min at 4° C. Cells were analyzed by flow cytometry by gating on the LIVE CD4⁺ cells. To measure the fold expansion of the CV-CAR Tregs after re-stimulation, CV-CAR⁺ cells were enriched by flow cytometry prior second round of stimulation (at day 7 after the first stimulation). These sorted CV-CAR⁺ Tregs were counted at day 5 after re-stimulation and fold expansion was calculated (cell number at day 5/cell number at day 0).

The ability of the signal mediated through the CAR of the generated CV-CAR Tregs to activate the cells was evaluated. Anti-CD3/CD28 beads were removed 5 days after transduction and transduced Tregs were let in culture for 2 days in presence of only IL-2 to allow them to rest and thus avoid any residual sign of activation. The different populations of CAR-Tregs were then re-stimulated in presence of only IL-2 (negative control) or Il-2 combined with either anti-CD3/CD28 beads (positive control) or SA Dynabeads® coated with biotinylated CV peptide (CV-SA beads, FIG. 13).

Figures 13, 14A:
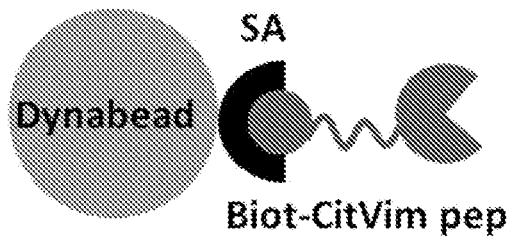
FIG. 13 is a schematic representation of a biotinylated CV-pep-SA bead formed from a SA DYNABEAD® coated with biotinylated CV peptide.
FIGS. 14A-14C. Evaluation of the ability of the signal mediated through the CV-CAR to activate the generated CV-CAR Tregs. After enrichment of the CV-specific CAR' Tregs by flow cytometry, cells were re-stimulated in presence or absence of anti-CD3/CD28 beads or biotinylated CV (CV-pep-SA) beads.

At day 1 after re-stimulation, presence of clusters in the wells was assessed, as an indication of interactions between the cells and the beads. As shown in FIG. 14A, clusters were absent in all wells, independently of the specificity of the transduced CAR, in the IL-2 only condition (without bead). As also shown in FIG. 14A, in the anti-CD3/CD28 bead condition, clusters were observed in all Treg populations. In this example, clusters were visible only in CV-CAR Treg wells when cells were cultured in presence of CV-SA beads, which may be indication that CV-CARs specifically interacted with CV-SA beads.

Figure 14B:
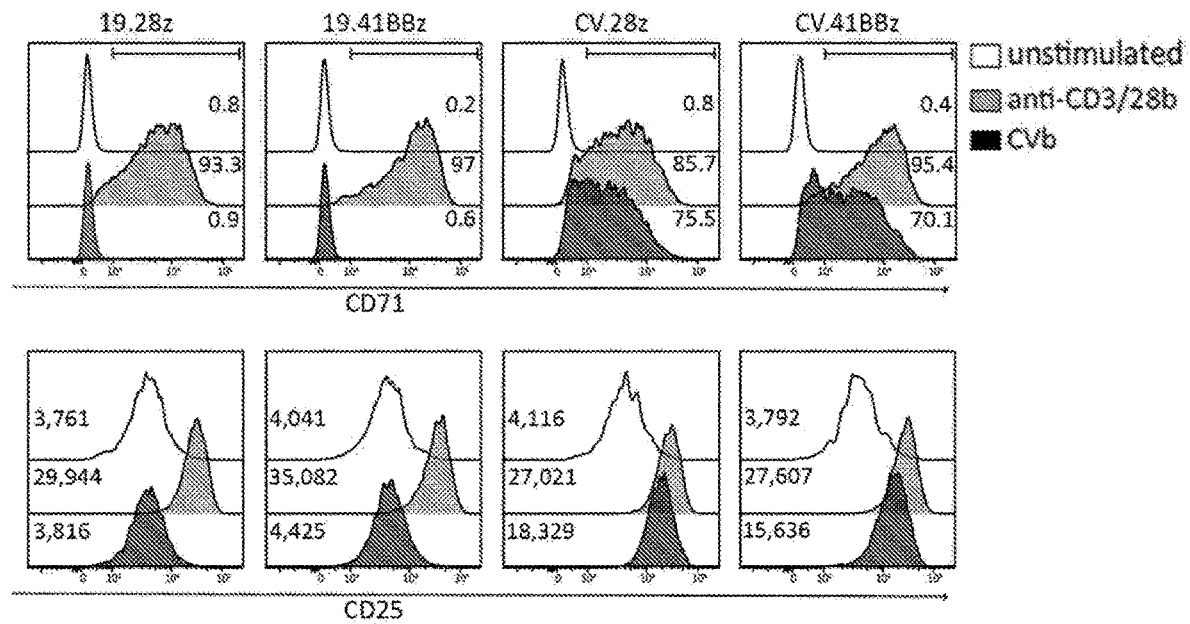

The expression of activation markers, CD71 and CD25, at the cell surface of the cells at day 3 was assessed by flow cytometry. Whereas in IL-2 only condition cells were not expressing CD71 and CD25 MFI was low, stimulation with anti-CD3/CD28 beads induced CD71 expression in the vast majority of the CAR Tregs (CD19 and CV specific) as well as a strong increase in CD25 MFI (FIG. 14B). An induction of CD71 expression was observed in CV-CAR Tregs only in CV-SA bead condition. The percentage of CD71⁺ cells was lower than the one observed with the anti-CD3/CD28 beads in particular with the CV.41BBz-CAR Tregs. Similarly, CD25 MFI was increase in CV-SA bead condition only in CV-CAR Tregs with a slightly higher MFI in CV.28z-CAR Tregs (FIG. 14C).

Figure 14C:
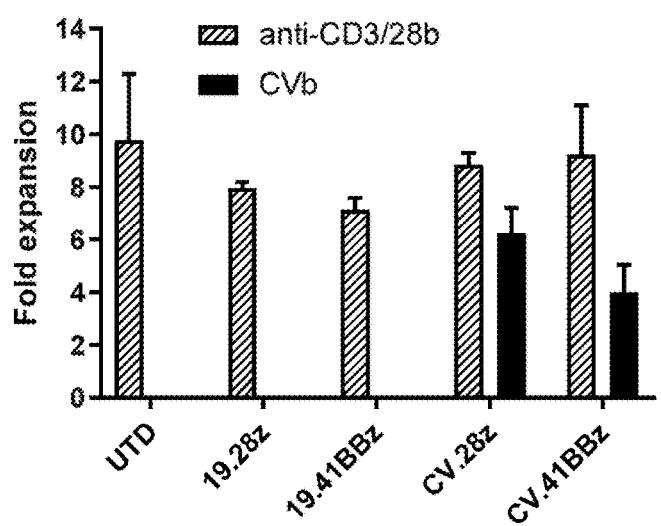

FIGS. 14A-14C show that only Tregs expressing CV-specific CARs displayed signs of activation when stimulated in presence of CV-SA beads.

It was then assessed whether the CV-specific-CAR-mediated stimulation induced in presence of CV-SA beads was sufficient to trigger expansion of the cells. The expansion fold of the different CAR Treg populations in all the conditions was measured at day 5 after re-stimulation (FIG. 14C). Resulting data showed that even if the fold expansion induced by CV-SA beads was lower than the one observed in presence of anti-CD3/CD28 beads, CV-CAR Tregs efficiently proliferated after stimulation mediated through the CV-specific-CAR. In coherence with the data shown in FIG. 14B, CV.41BBz-CAR Tregs appeared to expand less efficiently than CV.28z-CAR Tregs suggesting that CV.28z-CAR signaling might be more potent in activating the cells. These experiments were also performed on Tconv cells and gave similar results.

Moreover, to validate that the activation induced using CV-SA beads was due to the presence of $CV_{60-75}$ peptides, Arginin-Vimentin$_{60-75}$ (ArgVim) peptide-SA beads and Citrullinated-Fibrinogen beta chain$_{36-52}$(CitFib) peptide-SA beads were also generated. When CV-CAR Tregs were co-cultured in presence of uncoated SA-beads, ArgVim SA beads or CitFib SA beads, no sign of activation was observed.

Example 5: Assessment of the Phenotype and Stability of the CV-CAR Tregs after In Vitro Expansion Phenotypic analysis and assessment of cytokine production in expanded CV-CAR Tregs: At day 18, at the end of the second round of stimulation, a fraction of the different Treg populations were surface stained with fluorochrome-labeled Abs specific for CD4, CD25, CD127, EGFRt and LIVE/DEAD fixable blue for 20 min at 4° C. In parallel, another sample of the cells was stained with CD4, CD127, EGFRt and LIVE/DEAD fixable blue followed by an intranuclear staining of FOXP3 and Helios using the Foxp3 Staining Buffer Set (eBioscience) according to the manufacturer's instructions. For the assessment of cytokine production, cells were stimulated with PMA (100 ng/ml) and ionomycin (1 µg/ml) during 4 h, and brefeldin A (1×, Invitrogen) was added 2 hours after the beginning of the incubation. Cells were then stained with LIVE/DEAD fixable blue and anti-CD4, -CD127, -EGFRt Abs, fixed with 1% paraformaldehyde (PFA) in 1×PBS with 2% of D-Glucose, permeabilized with 0.1% saponin in PBS 5% FBS, and stained with Abs specific for IFN-γ, IL-2, IL-17 and IL-10. Cells were analyzed by flow cytometry (LSR II; BD Biosciences).

Figure 17A:
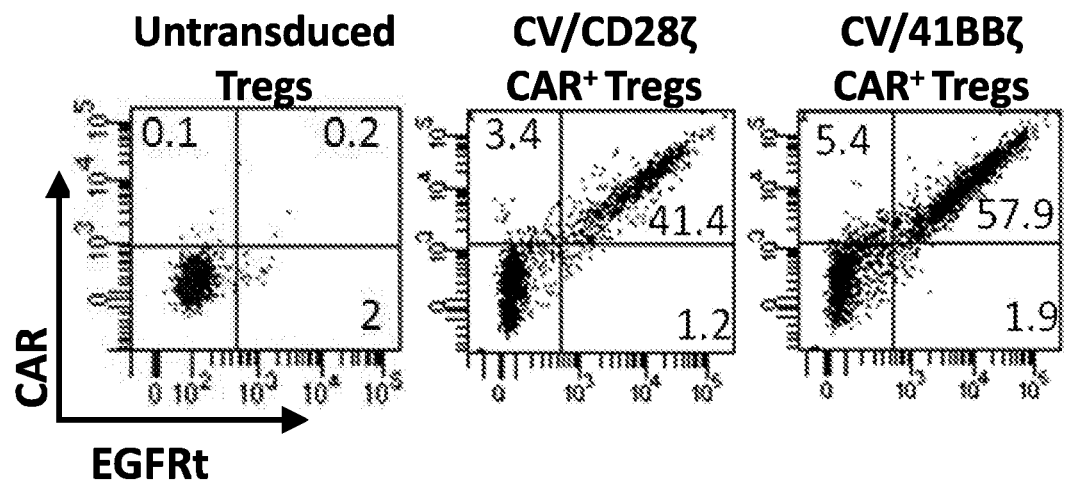
FIGS. 17A-17B. Assessment of the ability of CV-specific CAR to be expressed at the surface of the Tregs after lentiviral transduction. Both the CAR (using an anti-human IgG (H+L) antibody) and the epidermal growth factor receptor (EGFRt) were detected by flow cytometry.

To evaluate the phenotypic stability of the CV-CAR Tregs after two rounds of expansion, the expression profile of the main Treg surface markers (CD25, CD127) and transcription factors (FOXP3 and Helios) as well as the cytokine production at day 18 were examined. Non-transduced and CV-CAR Tregs underwent two rounds of stimulation with a second round of activation being with either anti-CD3/CD28 beads or CV-SA beads. At day 18, cells were assessed by flow cytometry for CD25 and CD127 surface expression (FIG. 15A) and FOXP3 and Helios intranuclear expression (FIG. 15B). As shown in FIGS. 17A and 15B, CV-CAR Tregs maintain their Treg phenotype after two rounds of stimulation in vitro.

To assess the cytokine production profile of these expanded Tregs, cells were stimulated with PMA/ionomycin for 4 hours, the last 2 hours in presence of brefeldin A. Cells were then fixed and stained with antibodies targeting IFN-g, IL-2, IL-10 and IL-17 (FIG. 15C).

Figure 15A:
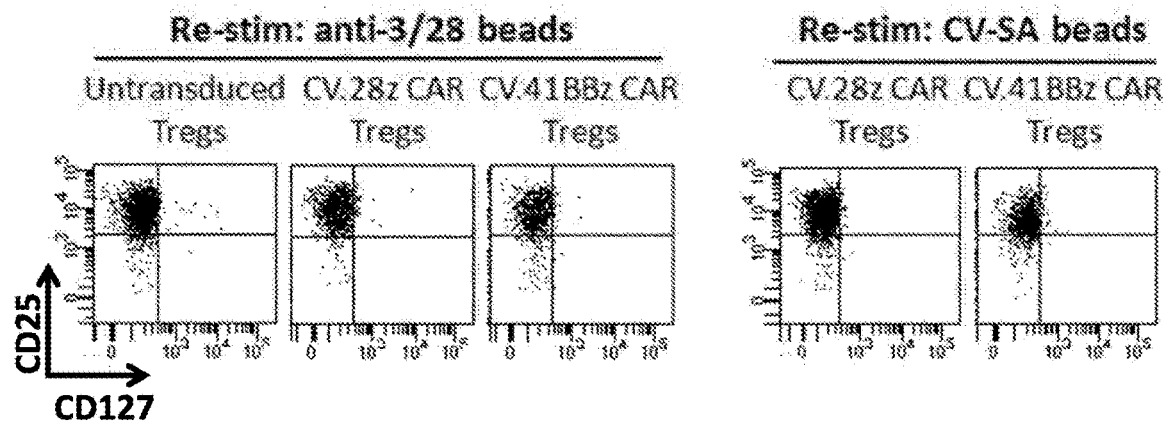
FIGS. 15A-15C. Assessment of the phenotype and stability of the CV-CAR Tregs after in vitro expansion. Non-transduced Tregs and CV-CAR Tregs underwent two rounds of stimulation with a second round of activation being with either anti-CD3/CD28 beads or CV-SA beads.
Figure 15B:
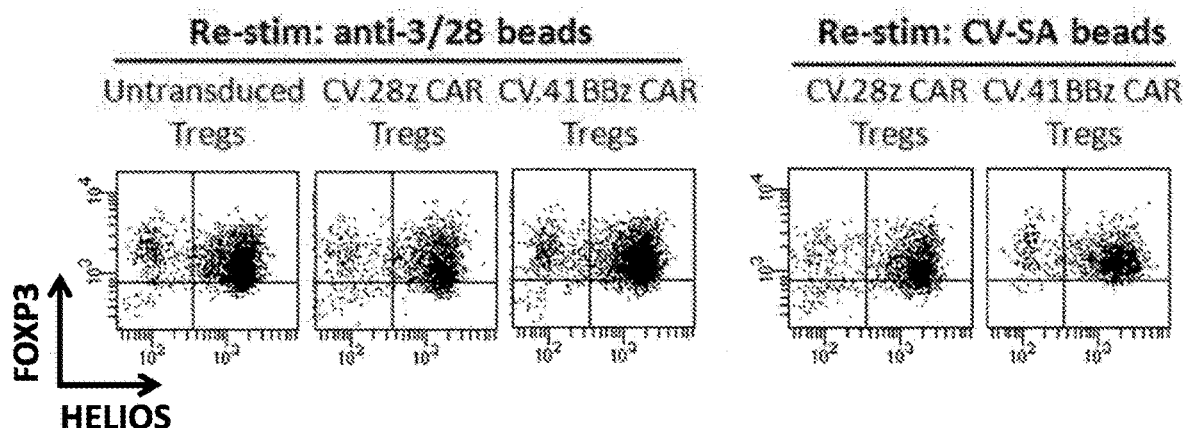
Figure 15C:
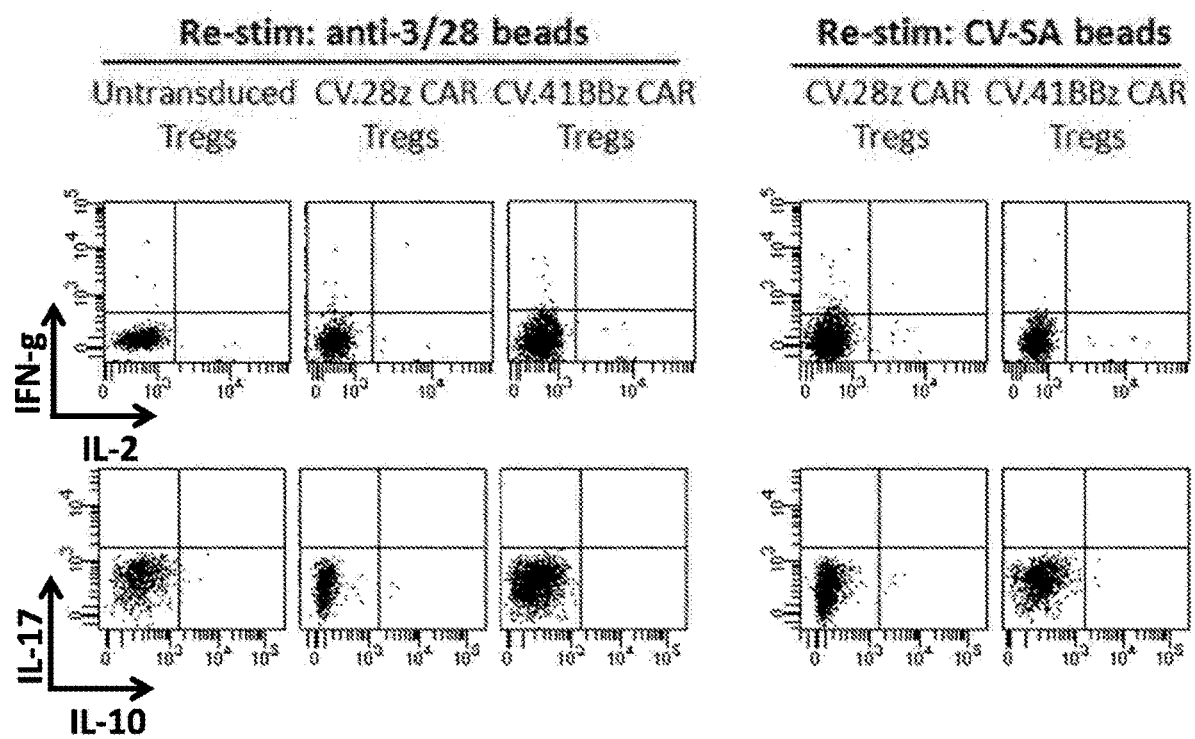

The three subsets: non-transduced Tregs, CV.28z-CAR Tregs and CV.41BBz-CAR Tregs maintained a Treg phenotype (i.e. CD25$^+$CD127$^-$, FOXP3$^+$), as shown in FIGS. 15A and 15B. It was observed that, none of the Tregs expressed IL-2 or the inflammatory cytokines,INF-g and IL-17 after expansion (FIG. 15C). No difference between non-transduced Tregs and CV-CAR Tregs was observed. Two conditions of re-stimulation were assessed at the second round: anti-CD3/CD28 beads or CV-SA beads. Similar profiles were obtained in both conditions which support the concept that Tregs maintain their phenotype after CV-CAR-mediated activation.

Example 6: Development of In Vitro Assays to Evaluate the Therapeutic Potential of CV-CAR Tregs in RA Co-culture of the CV-CAR Tregs with synovial fluid from RA patient: Synovial fluid (SF) samples from RA patients provided by Jonathan Graf were used to assess the ability of the CV-CAR Tregs of being activated through the CAR by using a more disease-related source of citrullinated vimentin. At day 9 after the first round of stimulation, synovial fluid samples (fresh or thawed) were mixed with T cell media supplemented with IL-2 at a ratio 1:8, 1:16 or 1:32 (SF:cell media). CAR T cells were seeded in 96-well plate at 50,000 cells per well and 200 µl of the mix of SF and T cell culture media was added in each well. After three days, cells were stained with antibodies specific for CD4, CD71, CD25 and LIVE/DEAD fixable blue stain as previously described. The percentage of cells expressing CD71 and the MFI of CD25 were obtained by flow cytometry by gating on the LIVE CD4$^+$ population.

Figure 20A:
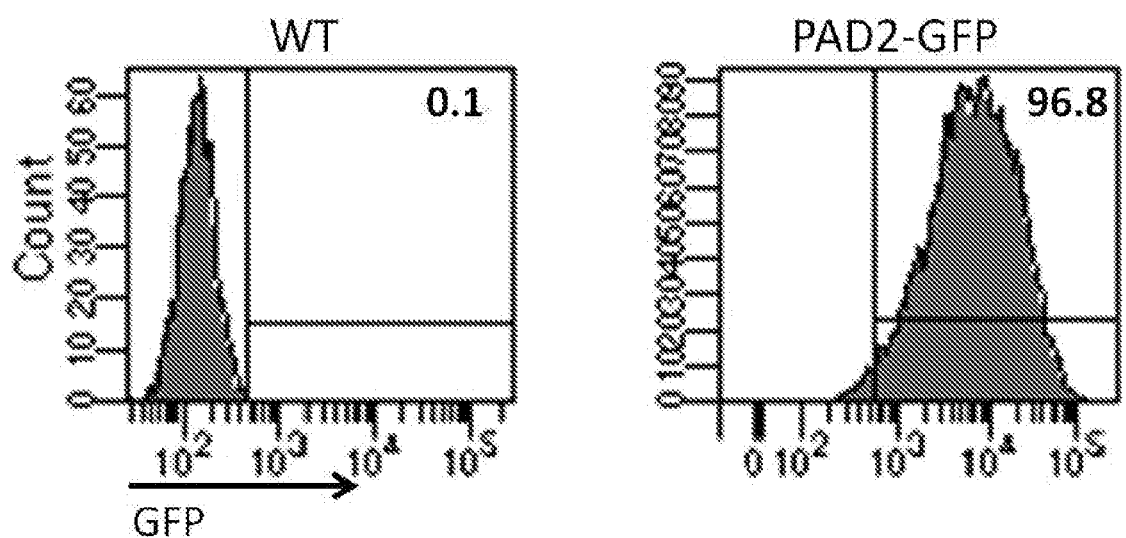
FIGS. 20A and 20B. Assessment of the expression of citrullinated vimentin in SKNBE2c tumor cell line after transduction with a PAD2-GFP lentiviral plasmid. The gene of the human enzyme peptidyl arginine deaminase (PAD2) was inserted into a lentivirus vector with a GFP reporter and then transduced into SKNBE2c cells, a tumor cell line known to express vimentin protein at the cell surface.
Figure 20B:
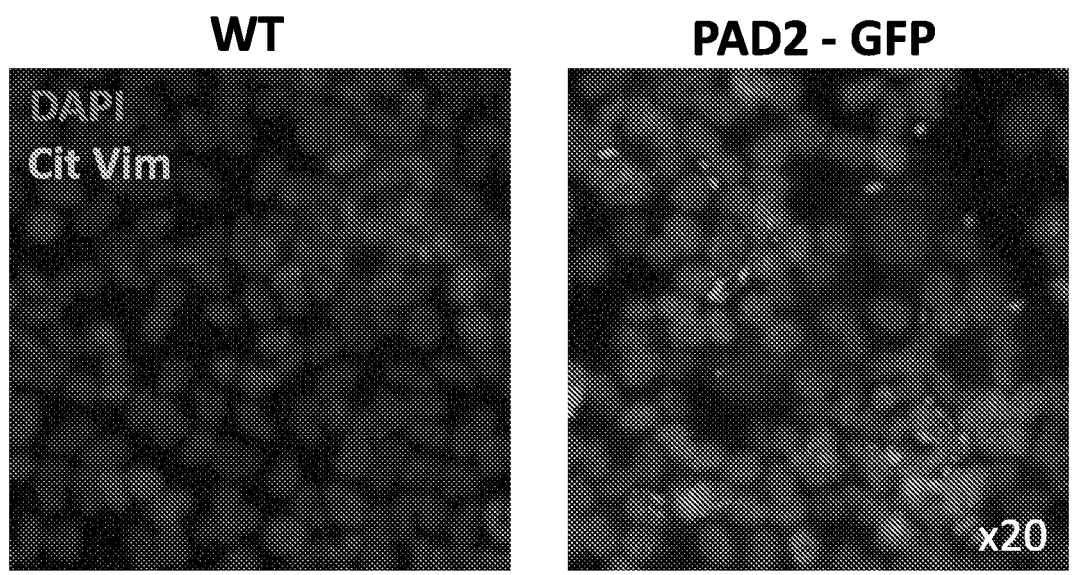

Generation of a tumor cell line expressing citrullinated vimentin and characterization: SKNBE2c is a neuroblastoma tumor cell line known to express vimentin at the cell surface. SKNBE2c cells (from ATCC) were thawed and cultured in RPMI with Glutamax, 10% FBS, HEPES and P/S. By using Gibson assembly method (Gibson Assembly Master Mix, BioLabs), the gene of the human enzyme peptidyl arginine deiminase 2 (PAD2) was inserted into a pCDH-EF1-T2A-GFP lentiviral vector (Addgene). Virus particles were produced by transfecting HEK 293T cells and SKNBE2c were transduced at a MOI of 1 particle per cell. The transfection and transduction efficiency were assessed by detecting the expression of GFP by flow cytometry. To determine if the artificial induction of the expression of the enzyme PAD2, involved in the citrullination process, triggered the production of citrullinated vimentin protein in the SKNBE2C, an immunofluorescence staining was performed. Briefly, both wild type (WT) and PAD-GFP transduced SKNBE2C cell lines were seeded into 8-well chamber borosilicate coverglass (Lab-Tek). When confluence was reached, cells were fixed with 2% PFA in cold 1× PBS for 30 min, blocked with 2% BSA in 1×PBS for 30 min at RT, incubated overnight with primary antibody (chimeric BVCA1 Ab with mouse IgG2a, anti-Vimentin Ab, or Isotype control) at 4° C. Secondary antibodies were then added for 1 h at RT in the dark and cells were counterstained with DAPI for 10 min. Cells were visualized using a fluorescence microscope (BZ-X700 series, Keyence). Results are shown in FIGS. 20A and 20B.

Co-culture of the CV-CAR Tregs with PAD2-GFP SKNBE2C cell lines: WT and PAD2-GFP SKNBE2C cells were seeded into flat bottom 96-well plate. Once confluence was reached, non-transduced Tregs, CD19-CAR Tregs and CV-CAR Tregs at day 10 of their first round of stimulation were added to the well in presence of T cell media complemented with IL-2 at 300 U/ml. After three days of co-culture, cells were harvested and stained with antibodies specific for CD4, CD71, CD25 and LIVE/DEAD fixable blue stain as previously described. The percentages of cells expressing CD71 and the MFI of CD25 were measured by flow cytometry by gating on the LIVE CD4$^+$ population.

Several in vitro approaches were used to demonstrate the ability of the CV-CAR T cells to be activated using a more disease-related source of citrullinated vimentin. The data obtained using synovial fluid from RA patient or CV-expressing tumor cell lines as a source of CV showed that CV.41BBz-CAR-transduced Tregs were not activated in these conditions whereas the CV.28z-CAR-transduced Tregs were efficiently activated. This demonstrates that even if both CV-CAR constructs are triggering an efficient activation signal to the CAR-expressing T cell in presence of CV-SA beads (artificial presentation of the target antigen), only CV.28z-CAR activate the cell in a more physiological context.

Figure 16A:
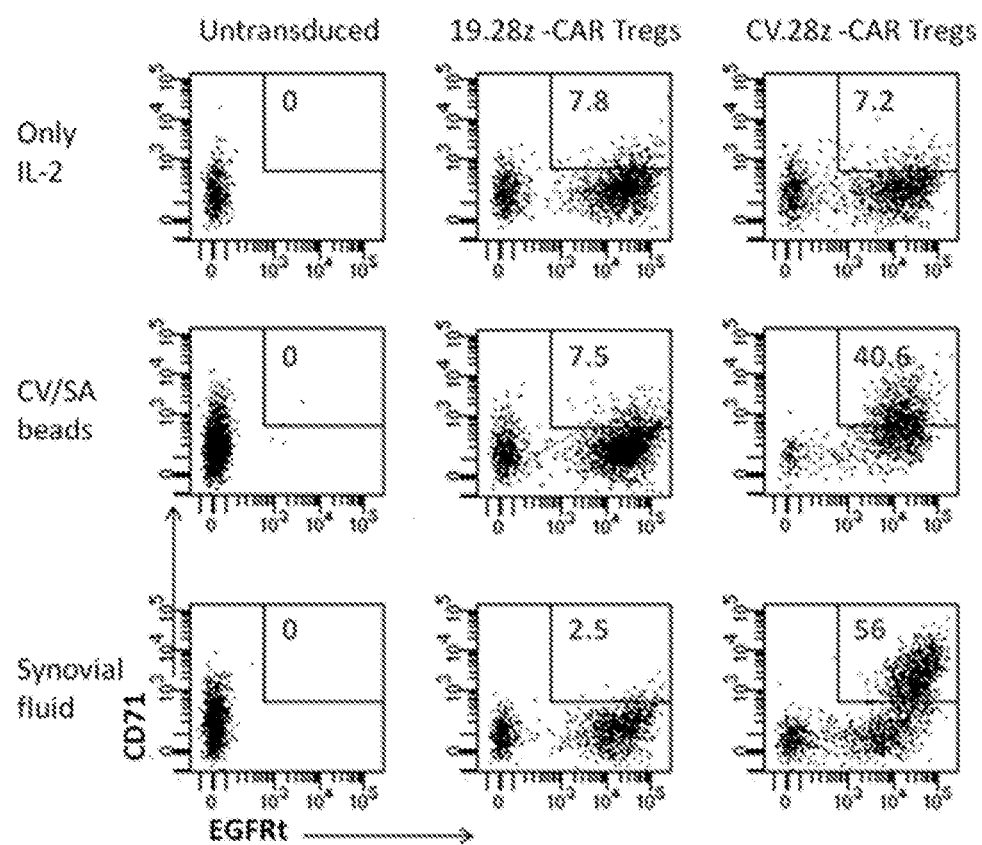
FIGS. 16A-16B. Assessment of the ability of the CV-CAR T cells to be activated in presence of synovial fluid harvested from the joint of rheumatoid arthritis (RA) patients. Expanded Tregs expressing various CAR constructs, as well as Non-transduced Tregs, were placed in culture in presence of IL-2 with or without CV-SA beads or synovial fluid from RA patient. Expression of CD71 was assessed by flow cytometry after 3.5 days of culture.
Figure 16B:
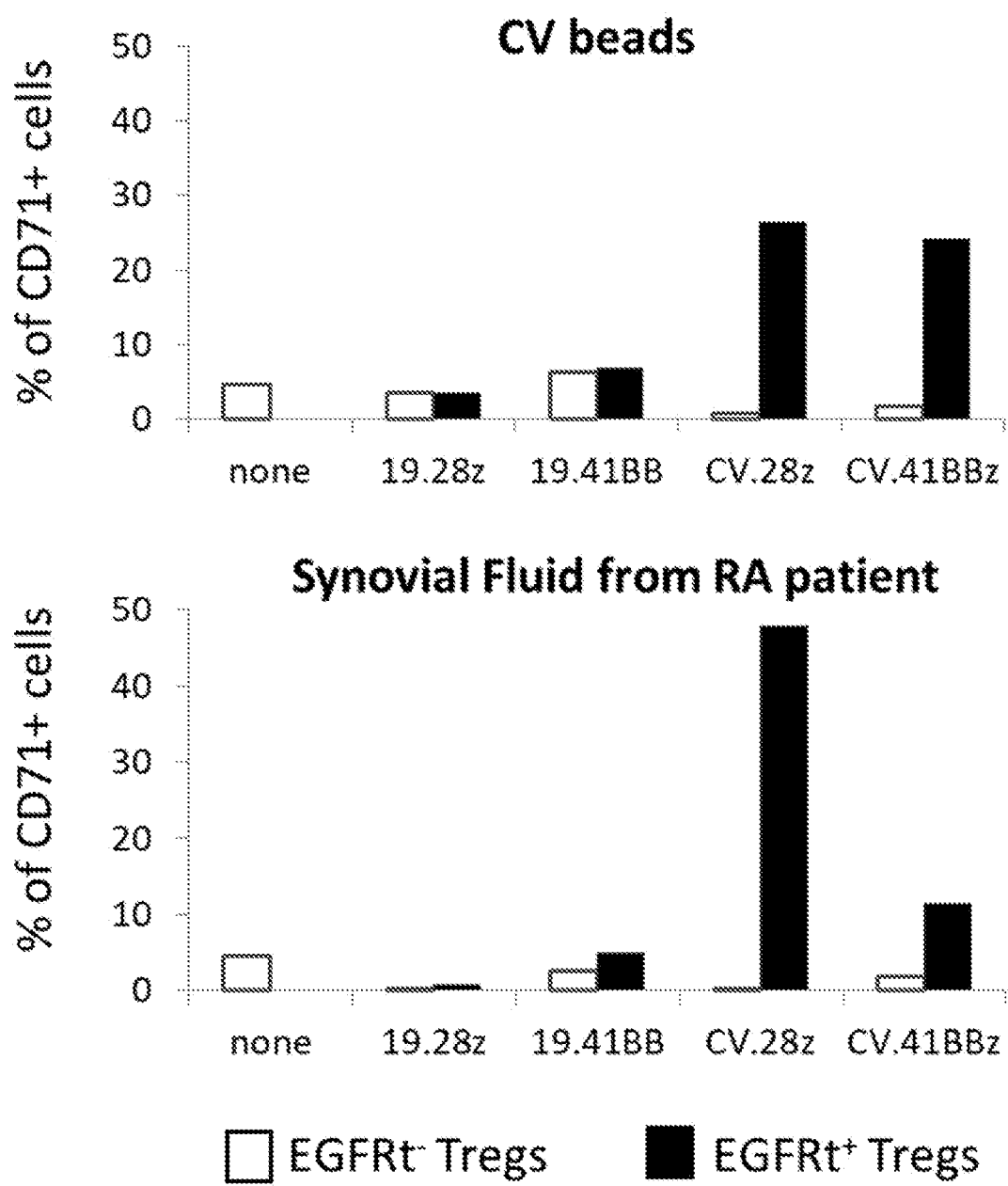

One of the in vitro approaches was to co-culture CV-CAR Tregs in presence of synovial fluid harvested from the joint of RA patients known to be enriched in neutrophils and neutrophil extracellular traps (NETs), one of the main sources of citrullinated vimentin in RA. Expanded Tregs expressing various CAR constructs, as well as non-transduced Tregs, were placed in culture in presence of IL-2 with or without CV-SA beads or synovial fluid from RA patient. Expression of CD71 was assessed by flow cytometry after 3.5 days of culture (FIG. 16A). FIG. 16B shows percentages of CD71$^+$ cells among the EGFRt$^-$ and EGFRt$^+$ fractions in the different CAR Treg populations.

Figure 18A:
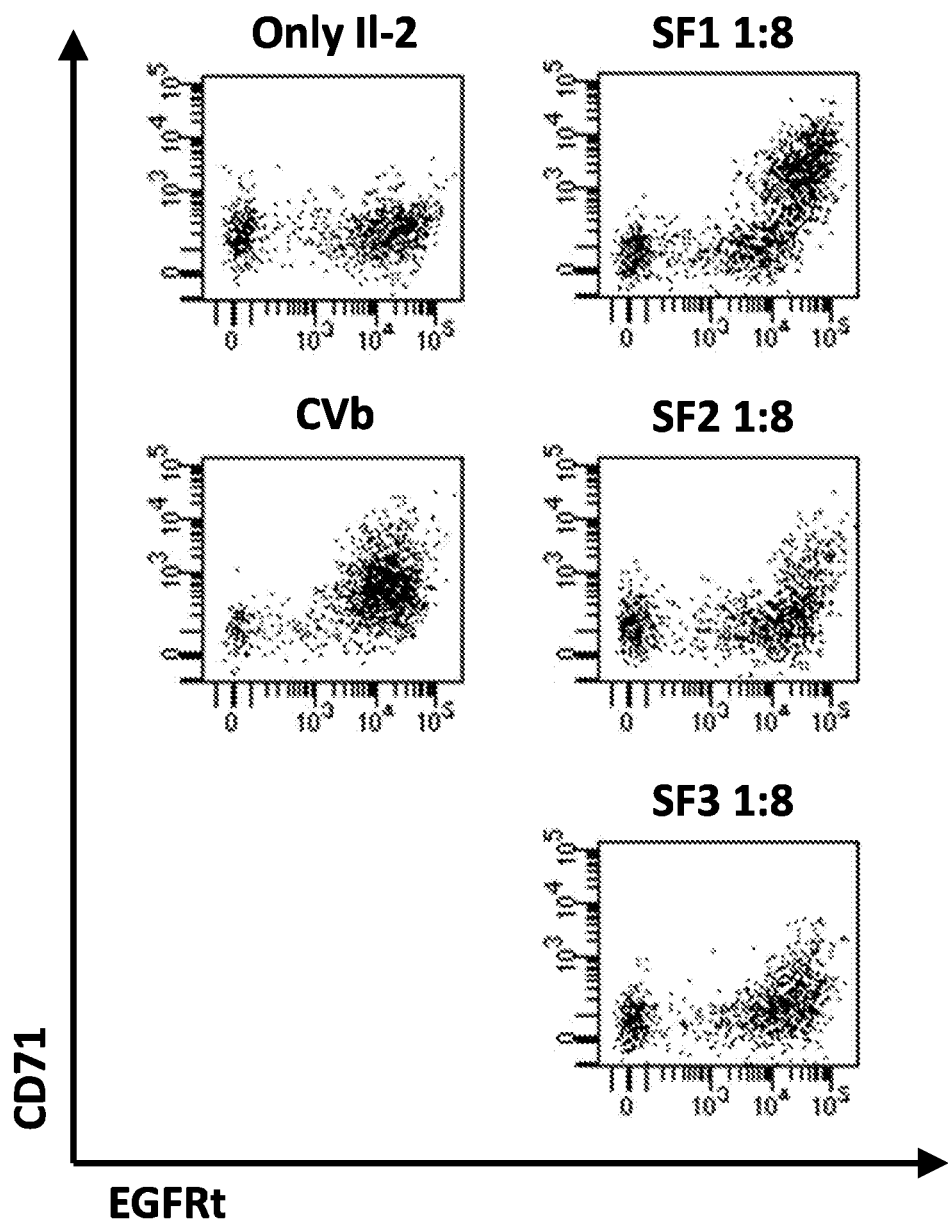
FIGS. 18A-18C. Assessment of the ability of the CV-CAR T cells to be activated in presence of synovial fluid harvested from the joint of rheumatoid arthritis (RA) patients. Expanded Tregs expressing various CAR constructs (19.28ζ-CAR Tregs, 19.41BBζ-CAR Tregs, CV.28ζ-CAR Tregs and 19.41BBζ-CAR Tregs), as well as Non-transduced (UTD) Tregs, were placed in culture in presence of IL-2 with or without CV-SA beads or synovial fluid (SF) from 3 different RA patients or SF from a control Gout patient. Expression of the activation marker CD71 was assessed by flow cytometry after 3.5 days of culture.

By staining the cells with CD71 Ab after 3.5 days of co-culture in presence of RA synovial fluid, it was observed that only the EGFRt$^+$ fraction of the CV.28z-CAR Tregs expressed high percentages of CD71 activation marker (FIGS. 16A and 16B). FIG. 16B is a summary of data obtained with SF from 4 different RA patients, non-transduced Tregs, CD19.28z-CAR Tregs and CD19.41BBz did not show any sign of activation in presence of synovial fluid. This experiment was also performed on Tconv cells and similar results were produced (data not shown). Three synovial fluid samples from different RA patients were tested and all of them specifically induced CD71 expression in EGFRt CV.28z-CAR Tregs (FIG. 18A) and Tconv (data not shown). These data suggest that this in vitro synovial-fluid-mediated activation is CV-CAR dependent. Importantly, only a weak expression of CD71 was induced at the surface of the EGFRt CV.41BBz-CAR at day 3.5 (FIG. 16B). This observation may be linked with the fact that CV.41BBz-CAR-mediated signal is less able to activate the cells than the one induced via CV.28z-CAR as shown in FIGS. 14A-14C.

Example 7: Treating a Human Subject with CV-CAR Tregs in RA

Referring back to FIG. 1, the CV-CAR Tregs have been generated in accordance with the described techniques to be used in the development of a cell therapy for patients with rheumatoid arthritis. This therapeutic approach involves using the Tregs of the patient itself (autologous) by isolating the cells from the patient's blood sample. The isolated Tregs are genetically reengineered using the lentiviral vector carrying the CV-CAR transgene. The CV-CAR Tregs undergo two rounds of expansion in vitro and are then infused to the patient. This can be done in combination with anti-TNF treatment to optimize the efficiency of the Tregs at the sites of the disease.

Accordingly, in some embodiments, a method of treating a subject diagnosed with rheumatoid arthritis is provided that includes isolating T lymphocytes from a biological sample obtained from the subject, separating CD4$^+$ T regulatory cells (Treg) from conventional T cells (Tconv), wherein the Treg cells are CD4$^+$CD25$^+$CD127$^-$ and the Tconv are CD4$^+$CD25$^-$CD127$^+$, transducing the Treg cells with an expression vector encoding a chimeric antigen receptor (CAR) which specifically binds to a citrullinated-vimentin (CV) antigen, stimulating with anti-CD3/anti-CD28 beads the transduced Treg cells at least once ex vivo to obtain a sufficient number of Treg cells specific for the CV antigen, and reinfusing the Treg into the subject, thereby treating the subject.

Example 8: Surface Expression of CV-CAR

Figure 17B:
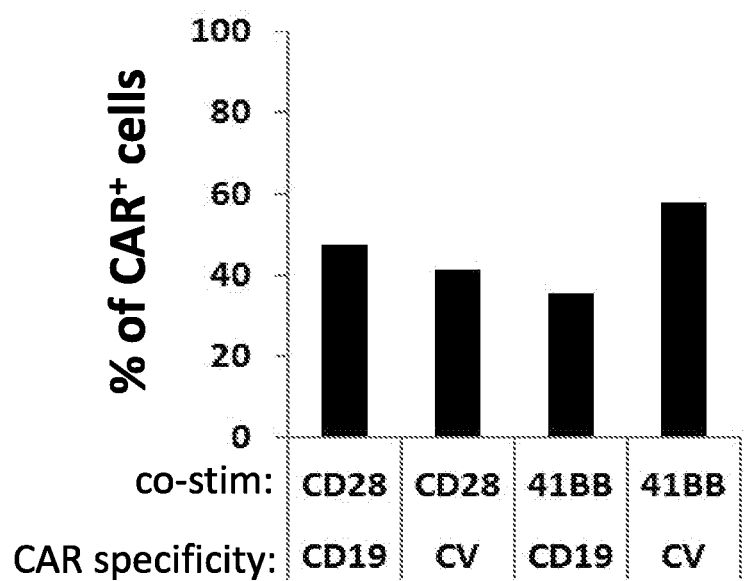

In some embodiments, the ability of CV-specific CAR to be expressed at the surface of the Tregs was assessed, as shown in FIGS. 17A-17B by using an anti-human IgG (H+L) Ab. This was done after lentiviral transduction. Both the CAR and the epidermal growth factor receptor (EGFRt) were detected by flow cytometry. FIG. 17A shows assessment of expression of CAR and EGFRt at the surface of non-transduced Tregs, CV/CD28ζ CAR$^+$ Tregs, and CV/41BBζ CAR$^+$ Tregs. FIG. 17B shows percentage of CAR$^+$ cells in various experiments.

Figure 18B:
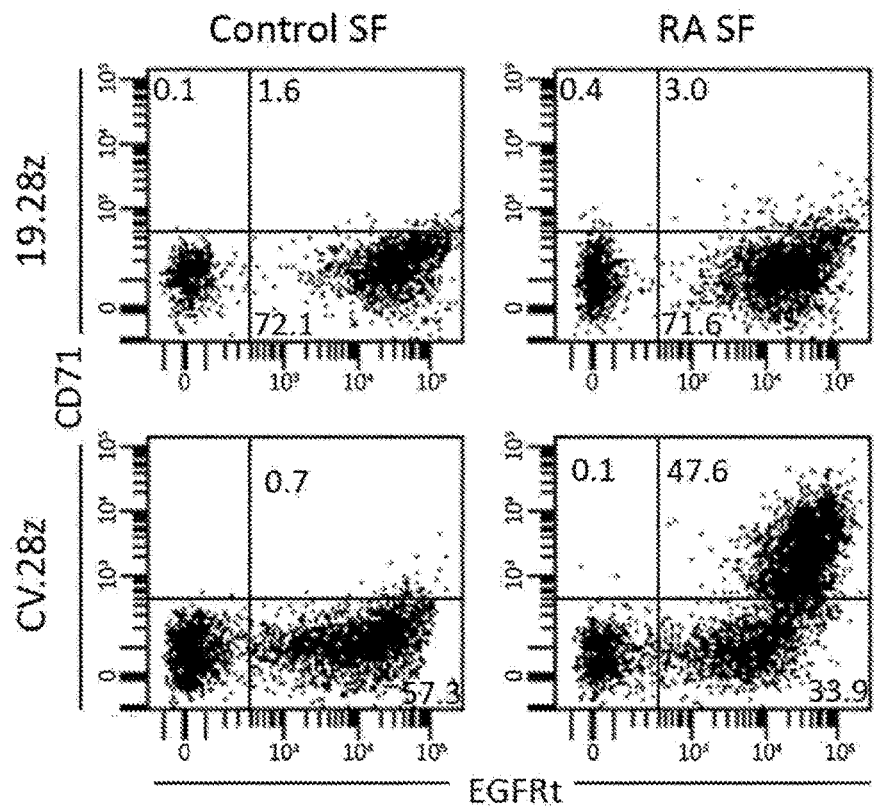
Figure 18C:
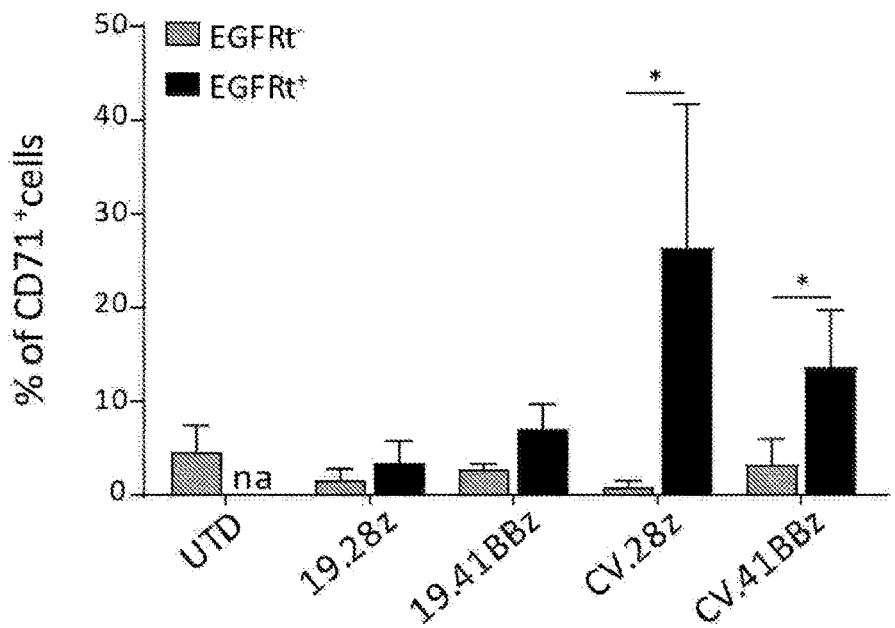
Figure 19:
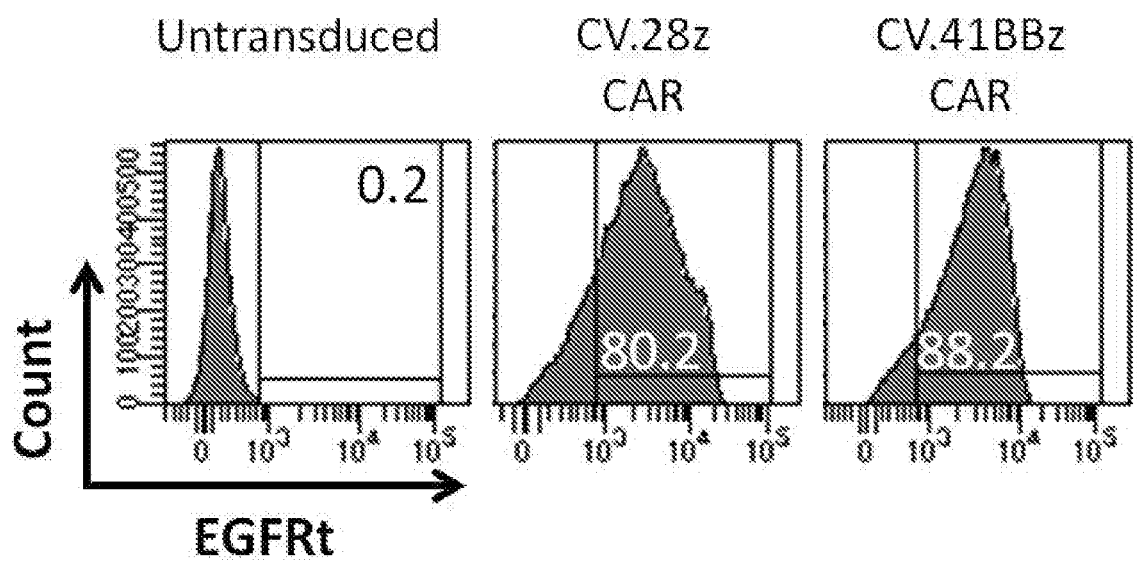
FIG. 19. Assessment of the expression of EGFRt in HEK 293T cells by flow cytometry three days after transfection. CV-CAR construct is efficiently expressed at the cell surface of HEK 293T cells after transfection.
Figure 21:
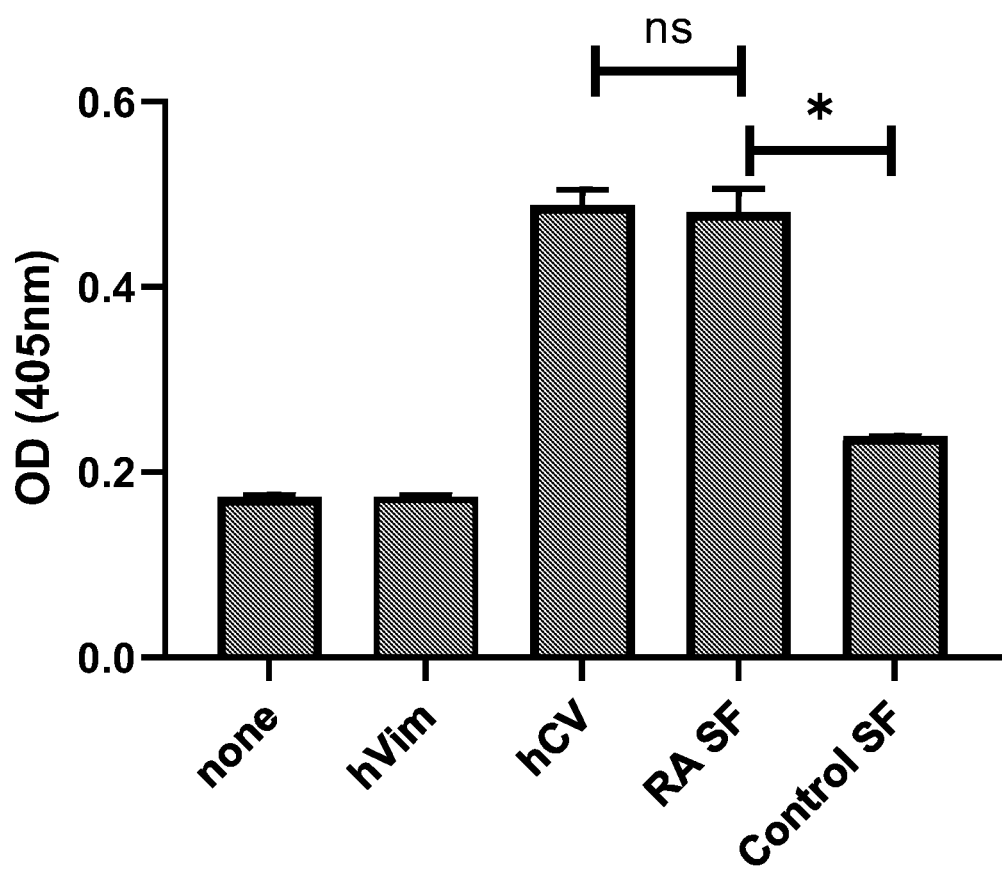
FIG. 21. Detection of citrullinated vimentin in synovial fluids by direct ELISA. The presence of citrullinated vimentin was assessed by ELISA in synovial fluids from RA and negative control Gout patients. Citrullinated and non-citrullinated vimentin proteins were used as positive and negative controls respectively.

Example 9: CV.28z-CAR Tregs are Activated in Presence of Synovial Fluid from RA Patients To demonstrate the ability of CV-CAR-expressing Tregs to recognize and signal in presence of a more clinically relevant source of citrullinated vimentin, we co-cultured CV-CAR Tregs in presence of synovial fluid harvested from the joint of RA patients known to be enriched in neutrophils and neutrophil extracellular traps (NETs), one of the main producers of CV in RA. After 3 days of co-culture with synovial fluid from patients with rather RA or gout, the latest being used as a negative control, the expression of CD71 was analyzed among the Treg cells. In presence of synovial fluid from the patient with gout, induction of CD71 expression was not observed in any of the Treg subsets (FIG. 18B). However, when co-cultures with synovial fluids from RA patients, CV.28z-CAR EGFRt Tregs expressed high percentages of the activation marker CD71 whereas EGFRt-Tregs present in the same well or CD19.28z-CAR Tregs and CD19.41BBz-CAR Tregs did not show any sign of activation (FIG. 18B and FIG. 18C). In consistency with these data, citrullinated vimentin was detected in synovial fluids from the RA patients but not in the one from the patient with gout (FIG. 21).

Example 10: CV.28z-CAR Tregs are Activated in Presence of Cell-Free Synovial Fluid from RA Patients Citrullinated vimentin was described to be mainly present in the extracellular matrix in the inflamed joint suggesting that cell-to-cell interaction may not be required for the CV.28z-CAR Tregs to be able to efficiently bind their target antigen. To verify that hypothesis, we compared the activation profile of CV.28z-CAR Tregs after co-culture in presence of whole synovial fluid or cell-free synovial fluid from RA patients by using the upper layer obtain after density gradient centrifugation. Our data revealed that a similar percentage of CV.28z-CAR Tregs were expressing CD71 in response to co-culture with synovial fluid from RA patients in presence or absence of cells in the fluid (FIG. 22A and FIG. 22B). All together, these data strongly support the concept that CV.28z-CAR-expressing Tregs will be capable of binding their target antigen in the extracellular matrix located in the inflamed joint of patients with RA.

Figure 23A:
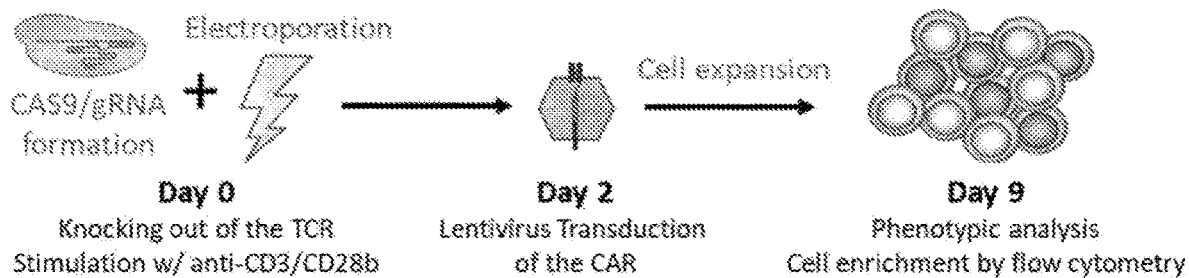
FIGS. 23A-23B. Generation of TCR$^{KO}$ CV.28z-CAR$^+$ Treg cells.
Figure 23B:
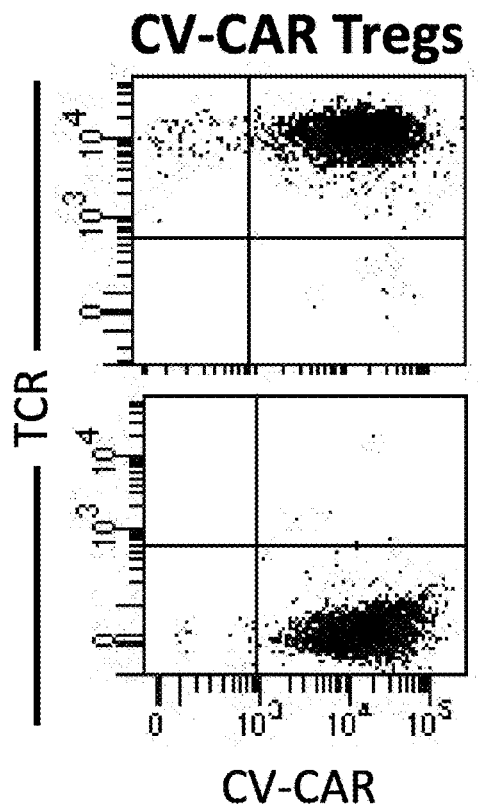
Figure 24A:
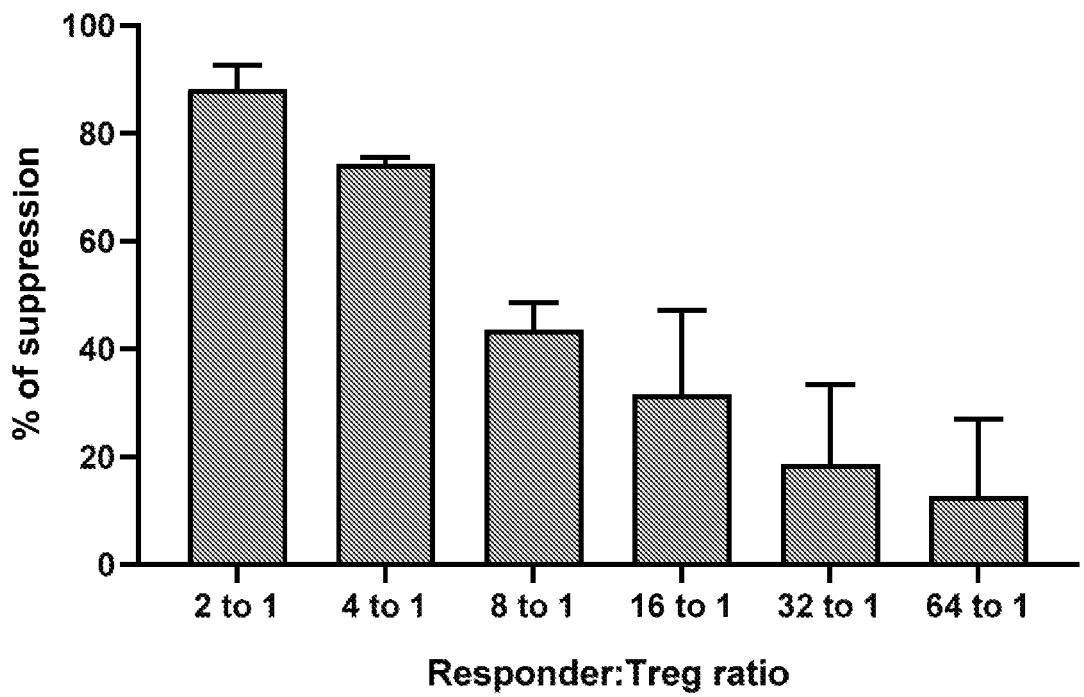
FIGS. 24A-24B. Assessment of the suppressive function of CV-CAR Tregs after CAR-mediated stimulation.
Figure 24B:
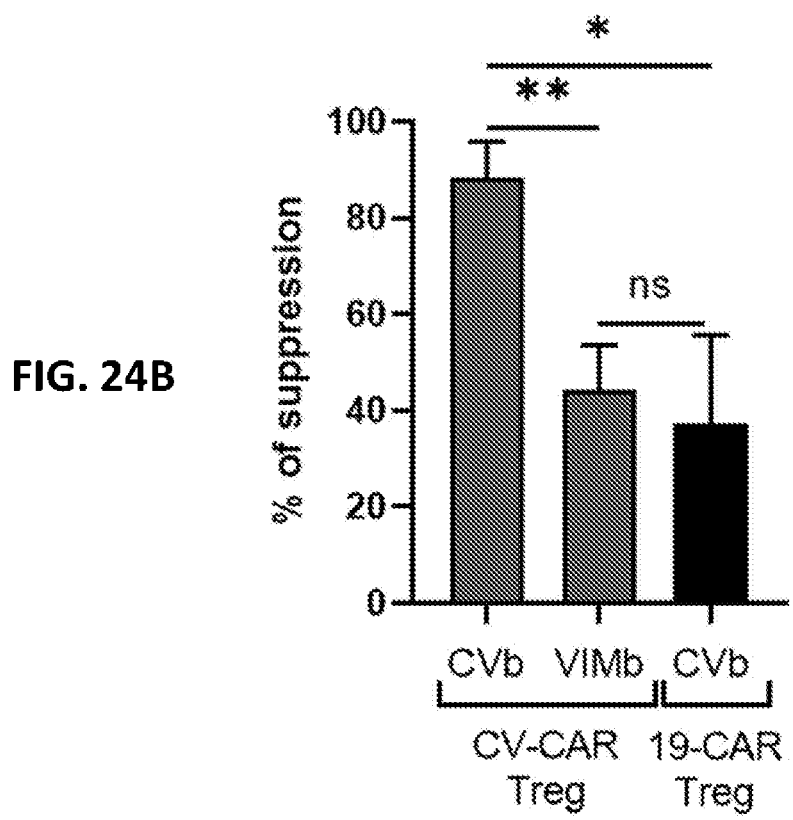

Example 11: CV.28z-CAR Treg Cell Suppressive Function after CAR-Mediated Stimulation To assess the suppressive capacities of the CV.28z-CAR Treg cells after CAR-mediated stimulation, CRISPR/Cas9 technology was used to knock out the endogenous TCR in Tregs to generate TCR$^{KO}$ CV.28z-CAR$^+$ Tregs (FIG. 23A and FIG. 23B). A suppression assay was performed using CD4$^+$ T effector cells stimulated with plate bound anti-CD3 antibodies as responders. The ability of the TCR$^{KO}$ CV.28z-CAR$^+$ Tregs to suppress these TCR-stimulated responder T cells in presence of CV-pep-SA beads (CVb) (FIG. 24A and FIG. 24B) or Vimentin beads (FIG. 24B) was assessed at different responder-to-suppressor cell ratios. Our data show that TCR$^{KO}$ CV.28z-CAR$^+$ Tregs are suppressive after CAR-mediated stimulation in presence of CV-SA beads whereas TCR$^{KO}$ CD19.28z-CAR$^+$ Tregs were not suppressive in presence of CV-SA beads.

Example 12: Materials and Methods

Co-culture of the CV-CAR Tregs with synovial fluid from RA patient: Synovial fluid (SF) samples from RA patients or negative control Gout patient provided by Jonathan Graf were used to assess the ability of the CV-CAR Tregs of being activated through the CAR by using a more disease-related source of citrullinated vimentin. When synovial fluid samples were in sufficient quantity, part of the fluid was diluted with 1×PBS and processed by density gradient centrifugation. The upper layer (cell-free) was collected after centrifugation and stored at −80 degrees. At day 9 after the first round of stimulation, whole synovial fluid samples and cell-free synovial fluid samples were thawed and mixed with T cell media supplemented with IL-2 at different ratios. CAR T cells were seeded in a 96-well plate at 50,000 cells per well and 200 µl of the mix of SF and T cell culture media was added in each well. After three days, cells were stained with antibodies specific for CD4, CD71, CD25 and LIVE/

DEAD fixable blue stain as previously described. The percentage of cells expressing CD71 and the MFI of CD25 were obtained by flow cytometry by gating on the LIVE CD4$^+$ population.

Detection of the presence of citrullinated vimentin in synovial fluid by direct ELISA: 96-well ELISA plates were coated O/N at 4° C. with chicken anti-vimentin Ab at 10 µg/ml. Wells were washed three times and blocked with 200 µl of 1×PBS 1% BSA for 1 h at RT and washed again. Different samples of synovial fluid supernatants diluted in PBS 1% BSA 0.1% Tween 20 were added and incubated for 1.5h at RT. In some other wells, vimentin protein and citrullinated vimentin proteins were added instead of synovial fluid to be used as negative and positive controls respectively. Wells were washed three times. 100 µl of mouse chimeric BVCA1 IgG (with mouse CH2 and CH3 domains) at 10 µg/ml or isotype control were added. After 1 h of incubation at RT, wells were washed 3 times and a Goat anti-mouse IgG2a secondary Ab-AP conjugated (Abcam, ab98695) was added to the well at 1/1000 dilution. Wells were washed three times and 100 µl of Step pNPP substrate solution was added. Reaction was stopped with 50 µl of NaOH 3M after 45 min and absorbance was read in a microplate reader at 405 nm.

Generation of TCR-knock-out CV-CAR$^+$ Treg cells using CRISPR/Cas9 technology. Treg cells were isolated from fresh PBMCs by flow cytometry as described in Example 3, centrifuged for 10 min at 90 g and resuspended in Lonza electroporation buffer P3 using 20 µl buffer per 1 million cells. Treg cells were then electroporated with CRISPR-Cas9 ribonucleoprotein (RNP) complexes using a Lonza 4D 96-well electroporation system with pulse code EH115. Immediately after electroporation, 80 µl of pre-warmed media was added to each well, and cells were placed to rest for 15 min at 37° C. Treg cells were then stimulated with anti-CD3/CD28 beads at a ratio 1:1 in presence of 300 UI of IL-2 per ml as detailed in Example 3. Two days after sort and electroporation, Treg cells were transduced with different CAR constructs as described in Example 3. 7 days later, cells were sorted based on the expression of EGFRt and CD3 into TCR$^{KO}$ CAR+ or TCR+ CAR+ populations. Cells were then re-stimulated with anti-CD3/CD28 beads at a ratio 1:1 in presence of 300 UI of IL-2 per ml for 5 to 6 days.

Suppression assay with TCR$^{KO}$ CAR$^+$ Tregs. Treg suppression was assessed by measuring proliferation based on [$^3$H] thymidine incorporation. After 12 days of expansion, anti-CD3/CD28 beads were removed from the TCR$^{KO}$ CV.28z-CAR$^+$ Treg and TCR$^{KO}$ 19.28 z-CAR$^+$ Treg cultures. Cells were rested for 2 days prior suppression assay. The day before the assay, CD4$^+$ T effector cells (responder cells) were thawed and kept at 37° C. 5% CO$_2$ overnight in presence of IL-2 30 UI/ml. Round bottom 96-well plates were coated with anti-CD3 antibody at 5 mg/ml overnight and washed with 1×PBS. The day of the assay, TCR$^{KO}$ CAR$^+$ Treg populations and responder cells were washed twice to remove residual IL-2 from the media. Cells were then plated in anti-CD3 Ab coated wells at 50,000 responder cells per well and TCR$^{KO}$ CAR$^+$ Tregs were added at different Responder:Treg ratios (from 2:1 to 64:1) in presence of rather Vimentin-SA-bead, CV-SA-bead, CD19-beads or no beads. 3 days later, 20 µl of [$^3$H] thymidine (1 µCi) were added to each well. 16 hours later, plates were frozen at −20 degrees. Plates were harvested on a Packard FilterMate Harvester and count per minute (CPM) for each well was read on a Packard TopCount Scintillation and Luminescence Counter (Perkin Elmer, Waltham, MA). For both assays, percent suppression was calculated as followed: % of suppression=1−[meanCPM(Treg+Responder)/meanCPM(responder alone)]×100%.

SEQUENCE LISTING

| SEQ ID NO | Sequence | Description |
|---|---|---|
| 1 | gttagaccagatctgagcctgggagctctctggctaactagggaaccactgcttaagcctcaataaag cttgccttgagtgcttcaagtagtgtgtgcccgtctgttgtgtgactctggtaactagagatccctcag acccttttagtcagtgtggaaaatctctagcagtggcgcccgaacagggacttgaaagcgaaagggaaa ccagaggagctctctcgacgcaggactcggcttgctgaagcgcgcacggcaagaggcgaggggcggcga ctggtgagtacgccaaaaattttgactagcggaggctagaaggagagatgggtgcgagagcgtcagt attaagcgggggagaattagatcgatgggaaaaaattcggttaaggccagggggaaagaaaaaatataa attaaaacatatagtatgggcaagcagggagctagaacgattcgcagttaatcctggcctgttagaaac atcagaaggctgtagacaaatactgggacagctacaaccatcccttcagacaggatcagaagaacttag atcattatataataacagtagcaaccctctattgtgtgcatcaaaggatagagataaaagacaccaagga agctttagacaagatagaggaagagcaaaacaaaagtaagaaaaaagcacagcaagcagcagctgacac aggacacagcaatcaggtcagccaaaattaccctatagtgcagaacatccaggggcaaatggtacatca ggccatatcacctagaactttaaatgcatgggtaaagtagtagaagagaaggctttcagcccagaagt gatacccatgttttcagcattatcagaaggagccacccaccaagatttaaacaccatgctaaacacagt gggggggacatcaagcagccatgcaaatgttaaaagagaccatcaatgaggaagctgcaggcaaagagaa gagtggtgcagagagaaaaaagagcagtgggaataggagctttgttccttgggttcttgggagcagcag gaagcactatgggcgcagcgtcaatgacgctgacggtacaggccagacaattattgtctggtatagtgc agcagcagaacaatttgctgagggctattgaggcgcaacagcatctgttgcaactcacagtctgggga tcaagcagctccaggcaagaatcctggctgtggaaagatacctaaaggatcaacagctcctggggattt ggggttgctctggaaaactcatttgcaccactgctgtgccttggatctacaaatggcagtattcatcca caattttaaaagaaaagggggattggggggtacagtgcaggggaaagaatagtagacataatagcaac agacatacaaactaaagaattacaaaaacaaattacaaaaattcaaaattttcgggtttattacaggga cagcagagatccagtttggggatcaattgcatgaagaatctgcttagggttaggcgttttgcgctgctt cgcgaggatctgcgatcgctccggtgcccgtcagtgggcagagcgcacatcgcccacagtccccgagaa gttgggggggagggtcggcaattgaaccggtgcctagagaaggtggcgcggggtaaactgggaaagtga tgtcgtgtactggctccgccttttccgagggtggggagaaccgtatataagtgcagtagtcgccgt gaacgttcttttacgcaacgggtttgccgccagaacacagctgaagcttcgaggggctcgcatctctcct tcacgcgcccgccgccctacctgaggccgccatccacgccggttgagtcgcgttctgccgcctcccgcc tgtggtgcctcctgaactgcgtccgccgtctaggtaagtttaaagctcaggtcgagacccgggcctttgt ccggcgctccctggagcctacctagactcagccggctctccacgctttgcctgaccctgcttgctcaa ctctacgtctttgtttcgttttctgttctgcgccgttacagatccaagctgtgaccggcgcctacggct agcgccgccaccatgctgctgctggtgaccagcctgctgctgtgcgagctgcccacccccgccttttctg | Anti-CV CAR-CD28z expression vector |

SEQUENCE LISTING

| SEQ ID NO | Sequence | Description |
|---|---|---|
| | ctgatccccGAGGTGAAACTAATAGAATCTGGGGGAGGCTTGGTTGAGCCAGGGCGGTCTCTGAGACTC<br>GCGTGTACAACGTCTGGATTCACCTTTGCCGACTACGGTTTGTCCTGGTTCCGCCAGGG<br>TCCCGGCAAGGGCCTTGAATGGGTAGGTTTCACTGGACCGAAACACCTCGGTGAG<br>ACAACAGAATGCGCCCCGTCTGTGGAAGACAGATGCACCATCTCAAGAGATGATT<br>CCAAAAGCACCGTCTATCTGCAGATGCACAGGCTCCAACACGAAGACACAGCCGT<br>GTACTTCTGTGTTGGACCTTGGTTCGGCGACTTATTAATGTGGGGCCAGGGAACCC<br>TGGTCACCGTCTCCTCAGCTAGCTCCGGAGGCTCAACTTCTGGCTCCGGTAAGCCA<br>GGCAGCGGAGAAGGTAGTAGTGGATCCGCGCGCGCCATCCAGATGACCCAGTCTC<br>CATCCTCCCTGTCTGCATCTGTTGGAGACAGAGTCTCCATCACTTGCCGGGCAACTC<br>AGGACATCAGCACATCTTTAGGCTGGTATCACCAGAGACCCGGGAAAGCCCCGAG<br>GCTCCTGATCTATGGTGCTTCGAAGGTACAAACTGGGGTCCCATCACGATTCAGCG<br>GCAATGGGTCTGGCACAGAGTTCACTCTCACCATCAGCAGCCTGCAGCCTGAAGAT<br>ATAGGGACTTATTATTGTCTACAAGATGATGGTTTCCCGTTCACTGTTGGCCAGGG<br>CACCAAGCTGGACATCAAACGCGCGGCCGCAATTGAAGTTATGTATCCTCCTCCTT<br>ACCTAGACAATGAGAAGAGCAATGGAACCATTATCCATGTGAAAGGGAAACACCT<br>TTGTCCAAGTCCCCTATTTCCCGGACCTTCTAAGCCCTtctgggtgctggtggtcggaggcgtgct<br>ggcctgctacagcctgctggtcaccgtggccttcatcatcttttgggtgaggagtaagaggagcaggct<br>cctgcacagtgactacatgaacatgactccccgccgccccgggcccaccgcaagcattaccagccta<br>tgccccaccacgcgacttcgcagcctatcgctcccgggtgaagttcagcagaagcgccgacgccctgc<br>ctaccagcagggcagaatcagctgtacaacgagctgaacctgggcagaagggaagagtacgacgtcct<br>ggataagcggagaggccgggaccctgagatgggcggcaagcctcggcggaagaaccccaggaaggcct<br>gtataacgaactgcagaaagacaagatggccgaggcctacagcgagatcggcatgaagggcgagcggag<br>gcggggcaaggcccacgacggcctgtatcagggcctgtccaccgccaccaaggatacctacgacgccct<br>gcacatgcaggccctgccccaaggcctgcagggcggcggagagggcggaggaagtcttctaacatgcgg<br>tgacgtggaggagaatcccgccctaggatgcttctcctggtgacaagccttctgctctgtgagttacc<br>acacccagcattcctcctgatcccacgcaaagtgtgtaacggaataggtattggtgaatttaaagactc<br>actctccataaatgctacgaatattaaacacttcaaaaactgcacctccatcagtggcgatctccacat<br>cctgccggtggcatttaggggtgactccttcacacatactcctcctctggatccacaggaactggatat<br>tctgaaaaccgtaaaggaaatcacagggttttttgctgattcaggcttggcctgaaaacaggacggacct<br>ccatgcctttgagaacctagaaatcatacgcggcaggaccaagcaacatggtcagttttctcttgcagt<br>cgtcagcctgaacataacatccttgggattacgctccctcaaggagataagtgatggagatgtgataat<br>ttcaggaaacaaaaattttgtgctatgcaaatacaataaactggaaaaaactgtttgggacctccggtca<br>gaaaaccaaaattataagcaacagaggtgaaaacagctgcagaagtctgccatgcctt<br>gtgctcccccgagggctgctggggccccgagcccagggactgcgtctcttgccggaatgtcagccgagg<br>cagggaatgcgtgacaagtgcaaccttctggagggtgagccaagggagttttgtggagaactctgagtg<br>catacagtgccacccagagtgcctgcctcaggccatgaacatcacctgcacaggacggggaccagacaa<br>ctgtatccagtgtgcccactacattgacggcccccactgcgtcaagacctgccggcaggagtcatggg<br>agaaaacaacaccctggtctggaagtacgcagacgccggccatgtgtgccacctgtgccatccaaactg<br>cacctacggatgcactgggccaggtcttgaaggctgtccaacgaatgggcctaagatcccgtccatcgc<br>cactgggatggtggggggccctcctcttgctgctggtggtggccctggggatcggcctcttcatgtgagc<br>ggccgctctagaccccgggctgcaggaattcgatatcaagcttatcgataatcaacctctggattacaaa<br>atttgtgaaagattgactggtattcttaactatgttgctccttttacgctatgtgatacgctgctta<br>atgcctttgtatcatgctattgcttcccgtatggctttcattttctcctccttgtataaatcctggttg<br>ctgtctctttatgaggagttgtggcccgttgtcaggcaacgtggcgtggtgtgcactgtgtttgctgac<br>gcaaccccactggttggcgcattgccaccacctgtcagctccttttccgggactttcgctttccccctc<br>cctattgccacgcgcgaactcatcgccgcctgccttgcccgctgctggacaggggctcggctgttgggc<br>actgacaattccgtggtgttgtcggggaatcatcgtcctttccttggctgctcgcctgtgttgccacc<br>tggattctgcgcgggacgtccttctgctacgtccctttcggccctcaatccagcggaccttccttcccgc<br>ggcctgctgccggctctgcggcctcttccgcgtcttcgccttcgccctcagacgagtcggatctccctt<br>tgggccgcctccccgcatcgataccgtcgactagccgtaccttttaagaccaatgacttacaaggcagct<br>gtagatcttagccactttttaaaagaaaagggggggactggaagggctaattcactcccaaagaagacaa<br>gatctgcttttttgcctgtactgggtctctctggttagaccagatctgagcctgggagctctctggctaa<br>ctagggaacccactgcttaagcctcaataaagcttgccttgagtgcttcaagtagtgtgtgcccgtctg<br>ttgtgtgactctggtaactagagatccctcagaccctttagtcagtgtggaaaatctctagcagaatt<br>cgatatcaagcttatcgataccgtcgacctcgagggggggcccggtacccaattcgccctatagtgagt<br>cgtattacaattcactggccgtcgttttacaacgtcgtgactgggaaaaccctggcgttacccaactta<br>atcgccttgcagcacatcccccttcgccagctggcgtaatagcgaagaggcccgcaccgatcgccctt<br>cccaacagttgcgcagcctgaatggcgaatggaaattgtaagcgttaatattttgttaaaattcgcgtt<br>aaattttttgttaaatcagctcatttttaaccaataggccgaaatcggcaaaatcccttataaatcaaa<br>agaatagaccgagatagggttgagtgttgttccagtttggaacaagagtccactattaaagaacgtgga<br>ctccaacgtcaaagggcgaaaaccgtctatcagggcgatggcccactacgtgaaccatcaccctaatc<br>aagttttttggggtcgaggtgccgtaaagcactaaatcggaacctaaaggagcccccgatttagagc<br>ttgacggggaaagccggcgaacgtggcgagaaaggaagggaagaaagcgaaaggagcgggcgctagggc<br>gctggcaagtgtagcggtcacgctgcgcgtaaccaccacacccgccgcgcttaatgcgccgctacaggg<br>cgcgtcaggtggcacttttcggggaaatgtgcgcggaaccctatttgtttatttttctaaatacattc<br>aaatatgtatccgctcatgagacaataaccctgataaatgcttcaataatattgaaaaaggaagagtat<br>gagtattcaacatttccgtgtcgcccttattccctttttttgcggcattttgccttcctgtttttgctca<br>cccagaaacgctggtgaaagtaaaagatgctgaagatcagttgggtgcacgagtgggttacatcgaact<br>ggatctcaacagcggtaagatccttgagagttttcgccccgaagaacgttttccaatgatgagcacttt<br>taaagttctgctatgtggcgcggtattatcccgtattgacgccgggcaagagcaactcggtcgccgcat<br>acactattctcagaatgacttggttgagtactcaccagtcacagaaaagcatcttacggatggcatgac<br>agtaagagaattatgcagtgctgccataaccatgagtgataacactgcggccaacttacttctgacaac<br>gatcggaggaccgaaggagctaaccgcttttttgcacaacatgggggatcatgtaactcgccttgatcg | |

| SEQ ID NO | Sequence | Description |
|---|---|---|
| | ttgggaaccggagctgaatgaagccataccaaacgacgagcgtgacaccacgatgcctgtagcaatggc<br>aacaacgttgcgcaaactattaactggcgaactacttactctagcttcccggcaacaattaatagactg<br>gatggaggcggataaagttgcaggaccacttctgcgctcggcccttccggctggctggtttattgctga<br>taaatctggagccggtgagcgtgggtctcgcggtatcattgcagcactggggccagatggtaagccctc<br>ccgtatcgtagttatctacacgacggggagtcaggcaactatggatgaacgaaatagacagatcgctga<br>gataggtgcctcactgattaagcattggtaactgtcagaccaagtttactcatatatactttagattga<br>tttaaaacttcattttaatttaaaaggatctaggtgaagatcattttgataatctcatgaccaaaatc<br>ccttaacgtgagttttcgttccactgagcgtcagacccgtagaaagatcaaaggatcttacttgagat<br>cctttttttctgcgcgtaatctgctgcttgcaaacaaaaaaaccaccgctaccagcggtggtttgtttg<br>ccggatcaagagctaccaactcttttccgaaggtaactggcttcagcagagcgcagataccaaatact<br>gttcttctagtgtagccgtagttaggccaccacttcaagaactctgtagcaccgcctacatacctcgct<br>ctgctaatcctgttaccagtggctgctgccagtggcgataagtcgtgtcttaccgggttggactcaaga<br>cgatagttaccggataaggcgcagcggtcgggctgaacggggggttcgtgcacacagcccagcttggag<br>cgaacgacctacaccgaactgagatacctacagcgtgagctatgagaaagcgccacgcttcccgaaggg<br>agaaaggcggacaggtatccggtaagcggcagggtcggaacaggagagcgcacgagggagcttccaggg<br>ggaaacgcctggtatctttatagtcctgtcgggtttcgccacctctgacttgagcgtcgatttttgtga<br>tgctcgtcaggggggcggagcctatggaaaaacgccagcaacgcggcctttttacggttcctggccttt<br>tgctggccttttgctcacatgttctttcctgcgttatcccctgattctgtggataaccgtattaccgcc<br>tttgagtgagctgataccgctcgccgcagccgaacgaccgagcgcagcgagtcagtgagcgaggaagcg<br>gaagagcgcccaatacgcaaaccgcctctccccgcgcgttggccgattcattaatgcagctggcacgac<br>aggtttcccgactggaaagcgggcagtgagcgcaacgcaattaatgtgagttagctcactcattaggca<br>ccccaggctttacactttatgcttccggctcgtatgttgtgtggaattgtgagcggataacaatttcac<br>acaggaaacagctatgaccatgattacgccaagctcgaaattaaccctcactaaagggaacaaaagctg<br>gagctccaccgcggtggcggcctcgaggtcgagatccggtcgacgcagcaaccatagtcccgccctaac<br>tccgcccatcccgcccctaactccgcccagttccgcccattctccgccccatggctgactaattttttt<br>tatttatgcagaggccgaggccgcctcggcctctgagctattccagaagtagtgaggaggcttttttgg<br>aggcctaggcttttgcaaaaagcttcgacggtatcgattggctcatgtccaacattaccgccatgttga<br>cattgattattgactagttattaatagtaatcaattacggggtcattagttcatagcccatatatggag<br>ttccgcgttacataacttacggtaaatggcccgcctggctgaccgcccaacgacccccgcccattgacg<br>tcaataatgacgtatgttcccatagtaacgccaatagggactttccattgacgtcaatgggtggagtat<br>ttacggtaaactgcccacttggcagtacatcaagtgtatcatatgccaagtacgccccctattgacgtc<br>aatgacggtaaatggcccgcctggcattatgcccagtacatgaccttatgggactttcctacttggcag<br>tacatctacgtattagtcatcgctattaccatggtgatgcggttttggcagtacatcaatgggcgtgga<br>tagcggtttgactcacggggatttccaagtctccaccccattgacgtcaatgggagtttgttttggcac<br>caaaatcaacgggactttccaaaatgtcgtaacaactccgccccattgacgcaaatgggcggtaggcgt<br>gtacggaattcggagtggcgagccctcagatcctgcatataagcagctgcttttttgcctgtactgggtc<br>tctctg | |
| 2 | gttagaccagatctgagcctgggagctctctggctaactagggaacccactgcttaagcctcaataaag<br>cttgccttgagtgcttcaagtagtgtgtgcccgtctgttgtgtgactctggtaactagagatccctcag<br>acccttttagtcagtgtggaaaatctctagcagtggcgcccgaacagggacttgaaagcgaaagggaaa<br>ccagaggagctctctcgacgcaggactcggcttgctgaagcgcgcacggcaagaggcgaggggcggcga<br>ctggtgagtacgccaaaaattttgactagcggaggctagaaggagagagatgggtgcgagagcgtcagt<br>attaagcggggggagaattagatcgatgggaaaaaattcggttaaggccagggggaaagaaaaaataa<br>attaaaacatagtatgtgggcaagcagggagctagaacgattcgcagttaatcctggcctgttagaaac<br>atcagaaggctgtagacaaaatactgggacagctacaaccatcccttcagacaggatcagaagaacttag<br>atcattatataatacagtagcaaccctctattgtgtgcatcaaaggatagagataaaagacaccaagga<br>agctttagacaagatagaggaagagcaaaacaaaagtaagaaaaaagcacagcaagcagcagctgacac<br>aggacacagcaatcaggtcagccaaaattaccctatagtgcagaacatccaggggcaaatggtacatca<br>ggccatatcacctagaactttaaatgcatgggtaaaagtagtagaagagaaggctttcagcctggggg<br>cagaagtgatacccatgttttcagcattatcagaaggagccaccccacaagatttaaacaccatgctaa<br>acacagacatcaagcagccatgcaaatgttaaaagagaccatcaatgaggaagctgcaggcaaagagaa<br>gagtggtgcagagagaaaaaagcagtgggaataggagcttttgttccttgggttcttgggagcagcag<br>gaagcactatgggcgcagcgtcaatgacgctgacggtacaggccagacaattattgtctggtatagtgc<br>agcagcagaacaatttgctgagggctattgaggcgcaacagcatctgttgcaactcacagtctgggca<br>tcaagcagctccaggcaagaatcctggctgtggaaagatacctaaaggatcaacagctcctgggatt<br>ggggagctctggaaaactcatttgcaccactgctgtgccttggatctacaaatggcagtattcatccac<br>aattttaaaagaaaagggggattgggggtacagtgcaggggaaaatagtagacataataagcaaca<br>gacatacaaactaaagaattacaaaaacaaattacaaaaattcaaaattttcgggtttattacagggac<br>agcagagatccagtttgggatcaattgcatgaagaatctgcttagggttaggcgttttgcgctgcttc<br>gcgaggatctgcgatcgctccggtgcccgtcagtgggcagagcgcacatcgcccacagtccccgagaag<br>ttgggggaggggtcggcaattgaaccggtgcctagagaaggtggcgcggggtaaactgggaaagtgat<br>gtcgtgtactggctccgcctttttcccgagggtggggagaaccgtatataagtgcagtagtcgccgtg<br>aacgttcttttcgcaacgggtttgccgccagaacacagctgaagcttcgaggggctcgcatctctcct<br>tcacgcgcccgccgccctacctgaggccgccatccacgccggttgagtcgcgttctgccgcctcccgcc<br>tgtggtgcctcctgaactgcgtccgccgtctaggtaagtttaaagctcaggtcgagaccgggcctttgt<br>ccggcgctcccttggagcctacctagactcagccggctctccacgctttgcctgaccctgcttgctcaa<br>ctctacgtctttgtttcgttttctgttctgcgccgttacagatccaagctgtgaccggcgcctacggct<br>agcgccgccaccatgctgctgctggtgaccagcctgctgctgtgcgagctgcccaccccgcctttctg<br>ctgatccccGAGGTGAAACTAATAGAATCTGGGGGAGGCTTGGTTGAGCCAGGGCGGTCTCTGAGACTC<br>GCGTGTACAACGTCTGGATTCACCTTTGCCGACTACGGTTTGTCCTGGTTCCGCCAGGG<br>TCCCGGCAAGGGCCTTGAATGGGTAGGTTTCACTGGACCGAAACACCTCGGTGAG<br>ACAACAGAATGCGCCCCGTCTGTGGAAGACAGATGCACCATCTCAAGAGATGATT | Anti-CV<br>CAR-<br>41BBz<br>expres-<br>sion<br>vector |

SEQUENCE LISTING

| SEQ ID NO | Sequence | Description |
|---|---|---|
| | CCAAAAGCACCGTCTATCTGCAGATGCACAGGCTCCAACACGAAGACACAGCCGT<br>GTACTTCTGTGTTGGACCTTGGTTCGGCGACTTATTAATGTGGGGCCAGGGAACCC<br>TGGTCACCGTCTCCTCAGCTAGCTCCGGAGGCTCAACTTCTGGCTCCGGTAAGCCA<br>GGCAGCGGAGAAGGTAGTAGTGGATCCGCGCGCGCCATCCAGATGACCCAGTCTC<br>CATCCTCCCTGTCTGCATCTGTTGGAGACAGAGTCTCCATCACTTGCCGGGCAACTC<br>AGGACATCAGCACATCTTTAGGCTGGTATCACCAGAGACCCGGGAAAGCCCCGAG<br>GCTCCTGATCTATGGTGCTTCGAAGGTACAAACTGGGGTCCCATCACGATTCAGCG<br>GCAATGGGTCTGGCACAGAGTTCACTCTCACCATCAGCAGCCTGCAGCCTGAAGAT<br>ATAGGGACTTATTATTGTCTACAAGATGATGGTTTCCCGTTCACTGTTGGCCAGGG<br>CACCAAGCTGGACATCAAACGCGCGGCCGCAATTGAAGTTATGTATCCTCCTCCTT<br>ACCTAGACAATGAGAAGAGCAATGGAACCATTATCCATGTGAAAGGGAAACACCT<br>TTGTCCAAGTCCCCTATTTCCCGGACCTTCTAAGCCCttctgggtgctggtggtggtcggaggcgtgct<br>ggcctgctacagcctgctggtcaccgtggccttcatcatcttttgggtgaaacggggcagaaagaaact<br>cctgtatatattcaaacaaccatttatgagaccagtacaaactactcaagaggaagatggctgtagctg<br>ccgatttccagaagaagaagaaggaggatgtgaactgcgggtgaagttcagcagaagcgccgacgcccc<br>tgcctaccagcagggccagaatcagctgtacaacgagctgaacctgggcagaagggaagagtacgacgt<br>cctggataagcggagaggccgggaccctgagatgggcggcaagcctcggcggaagaaccccaggaagg<br>cctgtataacgaactgcagaaagacaagatggccgaggcctacagcgagatcggcatgaagggcgagcg<br>gaggcggggcaagggccacgacggcctgtatcagggcctgtccaccgccaccaaggatacctacgacgc<br>cctgcacatgcaggccctgcccccaaggctcgagggcggcggagagggcagaggaagtcttctaacatg<br>cggtgacgtggaggagaatcccggccctaggatgcttctcctggtgacaagccttctgctctgtgagtt<br>accacacccagcattcctcctgatcccacgcaaagtgtgtaacggaataggtattggtgaatttaaaga<br>ctcactctccataaatgctacgaatattaaacacttcaaaaactgcacctccatcagtggcgatctcca<br>catcctgccggtggcatttaggggtgactccttcacacatactcctcctctggatccacaggaactgga<br>tattctgaaaaccgtaaaggaaatcacagggttttttgctgattcaggcttggcctgaaaacaggacgga<br>cctccatgcctttgagaacctagaaatcatacgcggcaggaccaagcaacatggtcagttttctcttgc<br>agtcgtcagcctgaacataacatccttgggattacgctccctcaaggagataagtgatggagatgtgat<br>aatttcaggaaacaaaaatttgtgctatgcaaatacaataaaactggaaaaaactgtttgggacctccgg<br>tcagaaaaccaaaattataagcaacagaggtgaaaacagctgcaaggccacaggccaggtctgccatgc<br>cttgtgctcccccgagggctgctggggcccggagcccagggactgcgtctcttgccggaatgtcagccg<br>aggcagggaatgcgtggacaagtgcaaccttctggagggtgagccaagggagtttgtggagaactctga<br>gtgcatacagtgccacccagagtgcctgcctcaggccatgaacatccctgcacaggacggggaccaga<br>caactgtatccagtgtgcccactacattgacggccccccactgcgctcaagacctgcccggcaggagtcat<br>gggagaaaacaacaccctggtctggaagtacgcagacgccggccatgtgtgccacctgtgccatccaaa<br>ctgcacctacggatgcactgggcaggtcttgaaggctgtccaacgaatgggcctaagatcccgtccat<br>cgccactgggatggtggggggccctcctcttgctgctggtggtggccctggggatcggcctcttcatgtg<br>agcggccgctctagacccggggctgcaggaattcgatatcaagcttatcgataatcaacctctggattac<br>aaaatttgtgaaagattgactggtattcttaactatgttgctccttttacgctatgtggatacgctgct<br>ttaatgcctttgtatcatgctattgcttcccgtatggctttcatttttctcctccttgtatatatcctgg<br>ttgctgtctctttatgaggagttgtggcccgttgtcaggcaacgtggcgtggtgtgcactgtgtttgct<br>gacgcaaccccactggttggggcattgccaccacctgtcagctccttttccgggactttcgctttcccc<br>ctccctattgccacgcgcgaactcatcgccgcctgccttgcccgctgctggacaggggctcggctgttg<br>ggcactgacaattccgtggtgttgtcggggaaatcatcgtccttttccttggctgctcgcctgtgttgcc<br>acctggattctgcgcgggacgtccttctgctacgtcccttcggccctcaatccagcggaccttccttcc<br>cgcggcctgctgccggctctgcggcctcttccgcgtcttcgcctttcagcgaggactgagtcggatctcc<br>ctttgggccgcctccccgcatcgataccgtcgactagccgtaccttaagaccaatgacttacaaggca<br>gctgtagatcttagccacttttttaaaagaaaaggggggactggaagggctaattcactcccaaagaaga<br>caagatctgcttttttgcctgtactgggtctctctggttagaccagatctgagcctgggagctctctggc<br>taactagggaacccactgcttaagcctcaataaagcttgccttgagtgcttcaagtagtgtgtgcccgt<br>ctgttgtgtgactctggtaactagagatccctcagaccctttttagtcagtgtggaaaatctctagcaga<br>attcgatatcaagcttatcgataccgtcgacctcgaggggggcccggtacccaattcgccctatagtg<br>agtcgtattacaattcactggccgtcgttttacaacgtcgtgactgggaaaaccctggcgttacccaac<br>ttaatcgccttgcagcacatccccctttcgccagctggcgtaatagcgaagaggcccgcaccgatcgcc<br>cttcccaacagttgcgcagcctgaatggcgaatggaaattgtaagcgttaatattttgttaaaattcgc<br>gttaaattttgttaaatcagctcattttttaaccaataggccgaaatcggcaaaatcccttataaatc<br>aaaagaatagaccgagatagggttgagtgttgttccagtttggaacaagagtccactattaaagaacgt<br>ggactccaacgtcaaagggcgaaaaaccgtctatcagggcgatggcccactacgtgaaccatcaccta<br>atcaagttttttggggtcgaggtgccgtaaagcactaaatcggaaccctaaagggagccccccgatttag<br>agcttgacggggaaagccggcgaacgtggcgagaaaggaagggaagaaagcgaaaggagcgggcgctag<br>ggcgctggcaagtgtagcggtcacgctgcgcgtaaccaccacacccgccgcgcttaatgcgccgctaca<br>gggcgcgtcaggtggcacttttcggggaaatgtgcgcggaacccctatttgtttatttttctaaataca<br>ttcaaatatgtatccgctcatgagacaataaccctgataaatgcttcaataataattgaaaaaggaagag<br>tatgagtattcaacatttccgtgtcgcccttattcccttttttgcggcattttgccttcctgtttttgc<br>tcacccagaaacgctggtgaaagtaaaagatgctgaagatcagttgggtgcacgagtgggttacatcga<br>actggatctcaacagcggtaagatccttgagagttttcgccccgaagaacgttttccaatgatgagcac<br>ttttaaagttctgctatgtggcgcggtattatcccgtattgacgccgggcaagagcaactcggtcgccg<br>catacactattctcagaatgacttggagagtactcaccagtcacagaaaagcatcttacggatggcatg<br>acagtaagagaattatgcagtgctgccataaccatgagtgataacactgcggccaacttacttctgaca<br>acgatcggaggaccgaaggagctaaccgcttttttgcacaacatggggatcatgtaactcgccttgat<br>cgttgggaaccggagctgaatgaagccataccaaacgacgagcgtgacaccacgatgcctgtagcaatg<br>gcaacaacgttgcgcaaactattaactggcgaactacttactctagcttcccggcaacaattaatagac<br>tggatggaggcggataaagttgcaggaccacttctgcgctcggcccttccggctggctggtttattgct<br>gataaatctggagccggtgagcgtgggtctcgcggtatcattgcagcactggggccagatggtaagccc | |

| SEQ ID NO | Sequence | Description |
|---|---|---|
| | tcccgtatcgtagttatctacacgacggggagtcaggcaactatggatgaacgaaatagacagatcgct<br>gagataggtgcctcactgattaagcattggtaactgtcagaccaagtttactcatatatactttagatt<br>gatttaaaacttcattttaatttaaaaggatctaggtgaagatccttttttgataatctcatgaccaaa<br>atcccttaacgtgagttttcgttccactgagcgtcagaccccgtagaaaagatcaaaggatcttcttga<br>gatcctttttttctgcgcgtaatctgctgcttgcaaacaaaaaaaccaccgctaccagcggtggtttgt<br>ttgccggatcaagagctaccaactctttttccgaaggtaactggcttcagcagagcgcagataccaaat<br>actgttcttctagtgtagccgtagttaggccaccacttcaagaactctgtagcaccgcctacatacctc<br>gctctgctaatcctgttaccagtggctgctgccagtggcgataagtcgtgtcttaccgggttggactca<br>agacgatagttaccggataaggcgcagcggtcgggctgaacggggggttcgtgcacacagcccagcttg<br>gagcgaacgacctacaccgaactgagatacctacagcgtgagctatgagaaagcgccacgcttcccgaa<br>gggagaaaggcggacaggtatccggtaagcggcagggtcggaacaggagagcgcacgagggagcttcca<br>gggggaaacgcctggtatctttatagtcctgtcgggtttcgccacctctgacttgagcgtcgatttttg<br>tgatgctcgtcaggggggcggagcctatggaaaaacgccagcaacgcggcctttttacggttcctggcc<br>ttttgctggccttttgctcacatgttctttcctgcgttatcccctgattctgtggataaccgtattacc<br>gcctttgagtgagctgataccgctcgccgcagccgaacgaccgagcgcagcgagtcagtgagcgaggaa<br>gcggaagagcgcccaatacgcaaaccgcctctccccgcgcgttggccgattcattaatgcagctggcac<br>gacaggtttcccgactggaaagcgggcagtgagcgcaacgcaattaatgtgagttagctcactcattag<br>gcaccccaggctttacactttatgcttccggctcgtatgttgtgtggaattgtgagcggataacaattt<br>cacacaggaaacagctatgaccatgattacgccaagctcgaaattaaccctcactaaagggaacaaaag<br>ctggagctccaccgcggtggcgctcgaggtcgagatccgtcgaccagcaaccatagtcccgcccct<br>aactccgcccatcccgcccctaactccgcccagttccgcccattctccgccccatggctgactaatttt<br>ttttatttatgcagaggccgaggccgcctcggcctctgagctattccagaagtagtgaggaggcttttt<br>tggaggcctaggcttttgcaaaaagcttcgacggtatcgattggctcatgtccaacattaccgccatgt<br>ctgaattgattattgactagttattaatagtaatcaattacgggtcattagttcatagcccatatatg<br>gagttccgcgttacataacttacggtaaatggcccgcctggctgaccgcccaacgacccccgcccattg<br>acgtcaataatgacgtatgttcccatagtaacgccaatagggactttccattgacgtcaatgggtggag<br>tatttacggtaaactgcccacttggcagtacatcaagtgtatcatatgccaagtacgccccctattgac<br>gtcaatgacggtaaatggcccgcctggcattatgcccagtacatgaccttatgggactttcctacttgg<br>cagtacatctacgtattagtcatcgctattaccatggtgatgcggttttggcagtacatcaatgggcgt<br>ggatagcggtttgactcacggggatttccaagtctccaccccattgacgtcaatgggagtttgttttgg<br>caccaaaatcaacgggactttccaaaatgtcgtaacaactccgccccattgacgcaaatgggcggtagg<br>cgtgtacggaattcggagtggcgagccctcagatcctgcatataagcagctgcttttgcctgtactgg<br>gtctctctg | |
| 3 | VYATRSSAVRLRSSVP | Human vimentin peptide 60-75 |
| 4 | AYVTRSSAVRLRSSVP | Murine vimentin peptide 60-75 |
| 5 | gaggtgaaactaatagaatctgggggaggcttggttgagccagggcggtctctgagactcgcgtgtaca<br>acgtctggattcacctttgccgactacggtttgtcctggttccgccagggtcccggcaagggccttgaa<br>tgggtaggtttcactggaccgaaacacctcggtgagacaacagaatgcgcccgtctgtggaagacaga<br>tgcaccatctcaagagatgattccaaaagcaccgtctatctgcagatgcacaggctccaacacgaagac<br>acagccgtgtacttctgtgttggaccttggttcggcgacttattaatgtggggcagggaaccctggtc<br>accgtctcctcagctagctccggaggctcaacttctggctccggtaagccaggcagcggagaaggtagt<br>agtggatccgcgcgcgccatccagatgacccagtctccatcctccctgtctgcatctgttggagacaga<br>gtctccatcacttgccgggcaactcaggacatcagcacatctttaggctggtatcaccagagacccggg<br>aaagcccgaggctcctgatctatggtgcttcgaaggtacaaactggggtcccatcacgattcagcggc<br>agtgggtctggcacagagttcactctcaccatcagcagcctgcagcctgaagatatagggacttattat<br>tgtctacaagatgatggtttcccgttcactgttggccagggcaccaagctggacatcaaacgcgcggcc<br>gcaattgaagttatgtatcctcctccttacctagacaatgagaagagcaatggaaccattatccatgtg<br>aaagggaaacaccctttgtccaagtcccctatttcccggaccttctaagcccttctgggtgctggtggtg<br>gtcggaggcgtgctggcctgctacagcctgctggtcaccgtggccttcatcatcttttgggtgagggt<br>aagaggagcaggctcctgcacagtgactacatgaacatgactccccgccgcccgggccaccgcaag<br>cattaccagccctatgccccaccacgcgacttcgcagcctatcgctcccggtgaagttcagcagaagc<br>gccgacgccctgcctaccagcagggccagaatcagctgtacaacgagctgaacctgggcagaagggaa<br>gagtacgacgtcctggataagcggagaggccgggaccctgagatgggcggcaagcctcggcggaagaac<br>cccaggaaggcctgtataacgaactgcagaaagacaagatggccgaggcctacagcgagatcggcatg<br>aagggcgagcggaggcgggcaagggccacgacggcctgtatcagggcctgtccaccgccaccaaggat<br>acctacgacgccctgcacatgcaggccctgcccccaagg | Anti-CV CAR-CD28z, nucleotide |
| 6 | gaggtgaaactaatagaatctgggggaggcttggttgagccagggcggtctctgagactcgcgtgtaca<br>acgtctggattcacctttgccgactacggtttgtcctggttccgccagggtcccggcaagggccttgaa<br>tgggtaggtttcactggaccgaaacacctcggtgagacaacagaatgcgcccgtctgtggaagacaga<br>tgcaccatctcaagagatgattccaaaagcaccgtctatctgcagatgcacaggctccaacacgaagac<br>acagccgtgtacttctgtgttggaccttggttcggcgacttattaatgtggggccagggaaccctggtc<br>accgtctcctcagctagctccggaggctcaacttctggctccggtaagccaggcagcggagaaggtagt<br>agtggatccgcgcgcgccatccagatgacccagtctccatcctccctgtctgcatctgttggagacaga | Anti-CV CAR-41BBz, nucleotide |

SEQUENCE LISTING

| SEQ ID NO | Sequence | Description |
|---|---|---|
| | gtctccatcacttgccgggcaactcaggacatcagcacatctttaggctggtatcaccagagacccggg<br>aaagccccgaggctcctgatctatggtgcttcgaaggtacaaactggggtcccatcacgattcagcggc<br>aatgggtctggcacagagttcactctcaccatcagcagcctgcagcctgaagatatagggacttattat<br>tgtctacaagatgatggtttcccgttcactgttggccagggcaccaagctggacatcaaacgcgcggcc<br>gcaattgaagttatgtatcctcctccttacctagacaatgagaagagcaatggaaccattatccatgtg<br>aaagggaaacacctttgtccaagtcccctatttcccggaccttctaagccc<br>gtcggaggcgtgctggcctgctacagcctgctggtcaccgtggccttcatcatctttgggtgaaacgg<br>ggcagaaagaaactcctgtatatattcaaacaaccatttatgagaccagtacaaactactcaagaggaa<br>gatggctgtagctgccgatttccagaagaagaagaaggaggatgtgaactgcgggtgaagttcagcaga<br>agcgccgacgcccctgcctaccagcagggccagaatcagctgtacaacgagctgaacctgggcagaagg<br>gaagagtacgacgtcctgataagcggagaggccgggaccctgagtgggcggcaagcctcggcggaag<br>aacccccaggaagcctgtataacgaactgcagaaagacaagatggccgaggcctacagcgagatcggc<br>atgaagggcgagcggaggcggggcaagggccacgacggcctgtatcagggcctgtccaccgccaccaag<br>gataccctacgacgccctgcacatgcaggccctgccccaagg | |
| 7 | gaggtgaaactaatagaatctggggagcttggttgagccagggcggtctctgagactcgcgtgtaca<br>acgtctggattcacctttgccgactacggtttgtcctggttccgccagggtcccggcaagggccttgaa<br>tgggtaggttcactggaccgaaacacctcggtgagacaacagaatgcgcccgtctgtgaagacaga<br>tgcaccatctcaagagatgattccaaaagcaccgtctatctgcagatgcacaggctccaacacgaagac<br>acagccgtgtacttctgtgttggaccttggttcggcgacttattaatgtggggccagggaaccctggtc<br>accgtctcctcagctagctccggaggctcaacttctggctccggtaagccaggcagcggagaaggtagt<br>agtggatccgcgcgcgccatccagatgacccagtctccatcctccctgtctgcatctgttggagacaga<br>gtctccatcacttgccgggcaactcaggacatcagcacatctttaggctggtatcaccagagacccggg<br>aaagccccgaggctcctgatctatggtgcttcgaaggtacaaactggggtcccatcacgattcagcggc<br>aatgggtctggcacagagttcactctcaccatcagcagcctgcagcctgaagatatagggacttattat<br>tgtctacaagatgatggtttcccgttcactgttggccagggcaccaagctggacatcaaacgcgcggcc<br>gca | anti-CV scFv, nucleotide |
| 8 | attgaagttatgtatcctcctccttacctagacaatgagaagagcaatggaaccattatccatgtgaaa<br>gggaaacacctttgtccaagtcccctatttcccggaccttctaagccc | hCD28 spacer, nucleotide |
| 9 | ttctgggtgctggtggtggtcggaggcgtgctggcctgctacagcctgctggtcaccgtggccttcatc<br>atctttgggtg | CD28 TM domain, nucleotide |
| 10 | cgggtgaagttcagcagaagcgccgacgcccctgcctaccagcagggccagaatcagctgtacaacgag<br>ctgaacctgggcagaagggaagagtacgacgtcctggataagcggagaggccgggaccctgagatgggc<br>ggcaagcctcggcggaagaaccccaggaagcctgtataacgaactgcagaaagacaagatggccgag<br>gcctacagcgagatcggcatgaagggcgagcggaggcggggcaagggccacgacggcctgtatcagggc<br>ctgtccaccgccaccaaggataccctacgacgccctgcacatgcaggccctgccccaagg | CD3ζ intracellular domain, nucleotide |
| 11 | aggagtaagaggagcaggctcctgcacagtgactacatgaacatgactccccgccgccccgggcccacc<br>cgcaagcattaccagcccctatgccccaccacgcgacttcgcagcctatcgctcc | CD28 intracellular domain, nucleotide |
| 12 | aaacggggcagaaagaaactcctgtatatattcaaacaaccatttatgagaccagtacaaactactcaa<br>gaggaagatggctgtagctgccgatttccagaagaagaagaaggaggatgtgaactg | 41BB intracellular domain, nucleotide |
| 13 | EVKLIESGGGLVEPGRSLRLACTTSGFTFADYGLSWFRQGPGKGLEWVGFTGPKHLGE<br>TTECAPSVEDRCTISRDDSKSTVYLQMHRLQHEDTAVYFCVGPWFGDLLMWGQGTLV<br>TVSSASSGGSTSGSGKPGSGEGSSGSARAIQMTQSPSSLSASVGDRVSITCRATQDISTSL<br>GWYHQRPGKAPRLLIYGASKVQTGVPSRFSGNGSGTEFTLTISSLQPEDIGTYYCLQDD<br>GFPFTVGQGTKLDIKRAAAIEVMYPPPYLDNEKSNGTIIHVKGKHLCPSPLFPGPSKPFW<br>VLVVVGGVLACYSLLVTVAFIIFWVRSKRSLLHSDYMNMTPRRPGPTRKHYQPYAPP<br>RDFAAYRSRVKFSRSADAPAYQQGQNQLYNELNLGRREEYDVLDKRRGRDPEMGGK<br>PRRKNPQEGLYNELQKDKMAEAYSEIGMKGERRRGKGHDGLYQGLSTATKDTYDAL<br>HMQALPPR | Anti-CV CAR-CD28z, amino acid |

-continued

SEQUENCE LISTING

| SEQ ID NO | Sequence | Description |
|---|---|---|
| 14 | EVKLIESGGGLVEPGRSLRLACTTSGFTFADYGLSWFRQGPGKGLEWVGFTGPKHLGE TTECAPSVEDRCTISRDDSKSTVYLQMHRLQHEDTAVYFCVGPWFGDLLMWGQGTLV TVSSASSGGSTSGSGKPGSGEGSSGSARAIQMTQSPSSLSASVGDRVSITCRATQDISTSL GWYHQRPGKAPRLLIYGASKVQTGVPSRFSGNGSGTEFTLTISSLQPEDIGTYYCLQDD GFPFTVGQGTKLDIKRAAAIEVMYPPPYLDNEKSNGTIIHVKGKHLCPSPLFPGPSKPFW VLVVVGGVLACYSLLVTVAFIIFWVKRGRKKLLYIFKQPFMRPVQTTQEEDGCSCRFP EEEEGGCELRVKFSRSADAPAYQQGQNQLYNELNLGRREEYDVLDKRRGRDPEMGG KPRRKNPQEGLYNELQKDKMAEAYSEIGMKGERRRGKGHDGLYQGLSTATKDTYDA LHMQALPPR | Anti-CV CAR-41BBz, amino acid |
| 15 | EVKLIESGGGLVEPGRSLRLACTTSGFTFADYGLSWFRQGPGKGLEWVGFTGPKHLGE TTECAPSVEDRCTISRDDSKSTVYLQMHRLQHEDTAVYFCVGPWFGDLLMWGQGTLV TVSSASSGGSTSGSGKPGSGEGSSGSARAIQMTQSPSSLSASVGDRVSITCRATQDISTSL GWYHQRPGKAPRLLIYGASKVQTGVPSRFSGNGSGTEFTLTISSLQPEDIGTYYCLQDD GFPFTVGQGTKLDIKRAAA | anti-CV scFv, amino acid |
| 16 | IEVMYPPPYLDNEKSNGTIIHVKGKHLCPSPLFPGPSKP | hCD28 spacer, amino acid |
| 17 | FWVLVVVGGVLACYSLLVTVAFIIFWV | CD28 TM domain, amino acid |
| 18 | RVKFSRSADAPAYQQGQNQLYNELNLGRREEYDVLDKRRGRDPEMGGKPRRKNPQE GLYNELQKDKMAEAYSEIGMKGERRRGKGHDGLYQGLSTATKDTYDALHMQALPPR | CD3ζ intra-cellular domain, amino acid |
| 19 | RSKRSRLLHSDYMNMTPRRPGPTRKHYQPYAPPRDFAAYRS | CD28 intra-cellular domain, amino acid |
| 20 | KRGRKKLLYIFKQPFMRPVQTTQEEDGCSCRFPEEEEGGCEL | 41BB intra-cellular domain, amino acid |
| 21 | ValTyrAlaThrCitSerSerAlaValCitLeuCitSerSerValPro Cit = citrulline | Human CV peptide 60-75 |
| 22 | AlaTyrValThrCitSerSerAlaValCitLeuCitSerSerValPro Cit = citrulline | Murine CV peptide 60-75 |

What is claimed:

1. A chimeric antigen receptor (CAR) comprising an antigen specific binding domain, a hinge domain, a transmembrane domain, co-stimulatory domain, and a CD3ζ signaling domain, wherein the antigen specific binding domain specifically binds to antigens comprising citrullinated-vimentin (CV) polypeptides or peptides thereof having the amino acid sequence of SEQ ID NO: 21 or 22, and wherein the co-stimulatory domain comprises a CD28 or a 41BB polypeptide, and wherein the antigen binding domain comprises a single chain variable fragment (scFv) which specifically binds to citrullinated-vimentin (CV), wherein the scFv comprises the complementarity determining region (CDR) sequences of SEQ ID NO:15.

2. The chimeric antigen receptor of claim 1, wherein:
a) the hinge domain is encoded by a nucleic acid sequence of SEQ ID NO: 8;
b) the transmembrane domain is encoded by a nucleic acid sequence of SEQ ID NO: 9;
c) the CD3ζ signaling domain is encoded by a nucleic acid sequence of SEQ ID NO: 10; and/or;
d) the CD28 co-stimulatory domain is encoded by a nucleic acid sequence of SEQ ID NO: 11.

3. The chimeric antigen receptor of claim 1, wherein:
a) the hinge domain is encoded by a nucleic acid sequence of SEQ ID NO: 8;
b) the transmembrane domain is encoded by a nucleic acid sequence of SEQ ID NO: 9;
c) the CD3ζ signaling domain is encoded by a nucleic acid sequence of SEQ ID NO: 10; and/or;
d) the 41BB co-stimulatory domain is encoded by a nucleic acid sequence of SEQ ID NO: 12.

4. The chimeric antigen receptor of claim 1, wherein the CV-CAR specifically binds to a CV peptide of SEQ ID NO: 21 or 22.

5. An isolated T cell that is modified to express: a chimeric antigen receptor (CAR) comprising an antigen binding domain linked to at least one co-stimulatory domain and a CD3ζ signaling domain, wherein the co-stimulatory domain comprises a CD28 or a 41BB polypeptide, and wherein the antigen binding domain comprises a single chain variable fragment (scFv) which specifically binds to citrullinated-vimentin (CV), having the amino acid sequence of SEQ ID NO: 21 or 22, wherein the scFv comprises the complementarity determining region (CDR) sequences of SEQ ID NO: 15.

6. The isolated T cell of claim 5, wherein:
a) the CAR comprises a hinge domain encoded by the nucleic acid sequence of SEQ ID NO: 8;
b) the CAR comprises a transmembrane domain encoded by the nucleic acid sequence of SEQ ID NO: 9;
c) the CD3ζ signaling domain is encoded by the nucleic acid sequence of SEQ ID NO: 10; and/or;
d) the CD28 co-stimulatory domain is encoded by the nucleic acid sequence of SEQ ID NO: 11.

7. The isolated T cell of claim 5, wherein:
a) the CAR comprises a hinge domain encoded by the nucleic acid sequence of SEQ ID NO: 8;
b) the CAR comprises a transmembrane domain encoded by the nucleic acid sequence of SEQ ID NO: 9;
c) the CD3ζ signaling domain is encoded by the nucleic acid sequence of SEQ ID NO: 10; and/or;
d) the 41BB co-stimulatory domain is encoded by the nucleic acid sequence of SEQ ID NO: 12.

8. The isolated T cell of claim 5, wherein the T cell is a mammalian regulatory T cell (Treg).

9. The isolated T cell of claim 8, wherein the Treg cell is $CD4^+CD25^+ CD127^-FOXP3^+$.

10. An expression vector encoding a chimeric antigen receptor (CAR) comprising an antigen specific binding domain, a hinge domain, a transmembrane domain, co-stimulatory domain, and a CD3ζ signaling domain, wherein the antigen specific binding domain specifically binds to antigens comprising citrullinated-vimentin (CV) polypeptides or peptides thereof having the amino acid sequence of SEQ ID NO: 21 or 22, and wherein the co-stimulatory domain comprises a CD28 or a 41BB polypeptide, and wherein the antigen binding domain comprises a single chain variable fragment (scFv) which specifically binds to citrullinated-vimentin (CV), wherein the scFv comprises the complementarity determining region (CDR) sequences of SEQ ID NO:15.

11. A host cell comprising an expression vector encoding a chimeric antigen receptor (CAR) comprising an antigen specific binding domain, a hinge domain, a transmembrane domain, co-stimulatory domain, and a CD3ζ signaling domain, wherein the antigen specific binding domain specifically binds to antigens comprising citrullinated-vimentin polypeptides or peptides thereof having the amino acid sequence of SEQ ID NO: 21 or 22, and wherein the co-stimulatory domain comprises a CD28 or a 41BB polypeptide, and wherein the antigen binding domain comprises a single chain variable fragment (scFv) which specifically binds to citrullinated-vimentin (CV), wherein the scFv comprises the complementarity determining region (CDR) sequences of SEQ ID NO:15.

12. A method of treating a subject diagnosed with rheumatoid arthritis, comprising:
isolating T lymphocytes from a biological sample obtained from the subject;
separating $CD4^+$ T regulatory Cells (Treg) from conventional T cells (Tconv), wherein the Treg cells are $CD4^+CD25^+CD127^-$ and the Tconv are $CD4^+CD25^-CD127^+$;
transducing the Treg cells with an expression vector encoding a chimeric antigen receptor (CAR) comprising an antigen binding domain linked to at least one co-stimulatory domain and a CD3ζ signaling domain, wherein the co-stimulatory domain comprises a CD28 or a 41BB polypeptide, and wherein the antigen binding domain comprises a single chain variable fragment (scFv) which specifically binds to a citrullinated-vimentin (CV) antigen having the amino acid sequence of SEQ ID NO: 21 or 22, wherein the scFv comprises the complementarity determining region (CDR) sequences of SEQ ID NO:15;
expanding the transduced Treg with anti-CD3/CD28 beads at least once ex vivo to obtain expanded Treg cells specific for the CV antigen; and
reinfusing the Treg into the subject, thereby treating the subject.

13. The method of claim 12, wherein the Treg cells are autologous cells.

14. The method of claim 12, wherein:
a) the CAR comprises a hinge domain encoded by the nucleic acid sequence of SEQ ID NO: 8;
b) the CAR comprises a transmembrane domain encoded by the nucleic acid sequence of SEQ ID NO: 9;
c) the CD3ζ signaling domain is encoded by the nucleic acid sequence of SEQ ID NO: 10; and/or;
d) the CD28 co-stimulatory domain is encoded by the nucleic acid sequence of SEQ ID NO: 11.

15. The method of claim 12, wherein:
a) the CAR comprises a hinge domain encoded by the nucleic acid sequence of SEQ ID NO: 8;
b) the CAR comprises a transmembrane domain encoded by the nucleic acid sequence of SEQ ID NO: 9;
c) the CD3ζ signaling domain is encoded by the nucleic acid sequence of SEQ ID NO: 10; and/or;
d) the 41BB co-stimulatory domain is encoded by the nucleic acid sequence of SEQ ID NO: 12.

16. The method of claim 12, further comprising administering to the subject one or more anti-inflammatory agents and/or therapeutic agents.

17. The method of claim 16, wherein the anti-inflammatory agents comprise one or more antibodies which specifically bind to pro-inflammatory cytokines.

18. The method of claim 17, wherein the antibodies are anti-TNFα, anti-IL-6 or combinations thereof.

19. A chimeric antigen receptor (CAR) comprising an antigen binding domain, a hinge domain, a transmembrane domain, co-stimulatory domain, and a CD3ζ signaling domain, wherein the antigen specific domain comprises an antibody or antibody fragment, wherein the antibody fragment is a single chain variable fragment (scFv) which specifically binds to a citrullinated vimentin antigen, wherein the scFv comprises the complementarity determining region (CDR) sequences of SEQ ID NO: 15.

20. The chimeric antigen receptor of claim 19, wherein the co-stimulatory domain comprises a CD28 or a 41BB polypeptide.

* * * * *

SEQUENCE LISTING

<160> NUMBER OF SEQ ID NOS: 23

<210> SEQ ID NO 1
<211> LENGTH: 9484
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 1

-continued

```
gttagaccag atctgagcct gggagctctc tggctaacta gggaacccac tgcttaagcc      60
tcaataaagc ttgccttgag tgcttcaagt agtgtgtgcc cgtctgttgt gtgactctgg     120
taactagaga tccctcagac ccttttagtc agtgtggaaa atctctagca gtggcgcccg     180
aacagggact tgaaagcgaa agggaaacca gaggagctct ctcgacgcag gactcggctt     240
gctgaagcgc gcacggcaag aggcgagggg cggcgactgg tgagtacgcc aaaaattttg     300
actagcggag gctagaagga gagagatggg tgcgagagcg tcagtattaa gcggggagaa     360
attagatcga tgggaaaaaa ttcggttaag gccagggggga agaaaaaat ataaattaaa     420 acatatagta tgggcaagca gggagctaga acgattcgca gttaatcctg gcctgttaga     480
aacatcagaa ggctgtagac aaatactggg acagctacaa ccatcccttc agacaggatc     540
agaagaactt agatcattat ataatacagt agcaaccctc tattgtgtgc atcaaaggat     600
agagataaaa gacaccaagg aagctttaga caagatagag gaagagcaaa acaaaagtaa     660
gaaaaaagca cagcaagcag cagctgacac aggacacagc aatcaggtca gccaaaatta     720
ccctatagtg cagaacatcc aggggcaaat ggtacatcag gccatatcac ctagaacttt     780
aaatgcatgg gtaaaagtag tagaagagaa ggctttcagc ccagaagtga tacccatgtt     840
ttcagcatta tcagaaggag ccaccccaca agatttaaac accatgctaa acacagtggg     900
gggacatcaa gcagccatgc aaatgttaaa agagaccatc aatgaggaag ctgcaggcaa     960
agagaagagt ggtgcagaga gaaaaaagag cagtgggaat aggagctttg ttccttgggt    1020
tcttgggagc agcaggaagc actatgggcg cagcgtcaat gacgctgacg gtacaggcca    1080
gacaattatt gtctggtata gtgcagcagc agaacaattt gctgagggct attgaggcgc    1140
aacagcatct gttgcaactc acagtctggg gcatcaagca gctccaggca agaatcctgg    1200
ctgtggaaag atacctaaag gatcaacagc tcctggggat ttggggttgc tctggaaaac    1260
tcatttgcac cactgctgtg ccttggatct acaaatggca gtattcatcc acaattttaa    1320
aagaaaaggg gggattgggg ggtacagtgc aggggaaaga atagtagaca taatagcaac    1380
agacatacaa actaaagaat tacaaaaaca aattacaaaa attcaaaatt ttcgggttta    1440
ttacagggac agcagagatc cagtttgggg atcaattgca tgaagaatct gcttagggtt    1500
aggcgttttg cgctgcttcg cgaggatctg cgatcgctcc ggtgcccgtc agtgggcaga    1560
gcgcacatcg cccacagtcc ccgagaagtt ggggggaggg gtcggcaatt gaaccggtgc    1620
ctagagaagg tggcgcgggg taaactggga aagtgatgtc gtgtactggc tccgcctttt    1680
tcccgagggt gggggagaac cgtatataag tgcagtagtc gccgtgaacg ttcttttttcg    1740 caacgggttt gccgccagaa cacagctgaa gcttcgaggg gctcgcatct ctccttcacg    1800
cgcccgccgc cctacctgag gccgccatcc acgccggttg agtcgcgttc tgccgcctcc    1860
cgcctgtggt gcctcctgaa ctgcgtccgc cgtctaggta agtttaaagc tcaggtcgag    1920
accgggcctt tgtccggcgc tcccttggag cctacctaga ctcagccggc tctcacgct    1980 ttgcctgacc ctgcttgctc aactctacgt ctttgtttcg ttttctgttc tgcgccgtta    2040
cagatccaag ctgtgaccgg cgcctacggc tagcgccgcc accatgctgc tgctggtgac    2100
cagcctgctg ctgtgcgagc tgccccaccc cgcctttctg ctgatcccg aggtgaaact    2160 aatagaatct gggggaggct tggttgagcc agggcggtct ctgagactcg cgtgtacaac    2220
gtctggattc acctttgccg actacggttt gtcctggttc cgccagggtc ccggcaaggg    2280
ccttgaatgg gtaggtttca ctggaccgaa acacctcggt gagacaacag aatgcgcccc    2340
```

```
gtctgtggaa gacagatgca ccatctcaag agatgattcc aaaagcaccg tctatctgca    2400
gatgcacagg ctccaacacg aagacacagc cgtgtacttc tgtgttggac cttggttcgg    2460
cgacttatta atgtggggcc agggaaccct ggtcaccgtc tcctcagcta gctccggagg    2520
ctcaacttct ggctccggta agccaggcag cggagaaggt agtagtggat ccgcgcgcgc    2580
catccagatg acccagtctc catcctccct gtctgcatct gttggagaca gagtctccat    2640
cacttgccgg gcaactcagg acatcagcac atctttaggc tggtatcacc agagacccgg    2700
gaaagccccg aggctcctga tctatggtgc ttcgaaggta caaactgggg tcccatcacg    2760
attcagcggc aatgggtctg gcacagagtt cactctcacc atcagcagcc tgcagcctga    2820
agatatcggg acttattatt gtctacaaga tgatggtttc ccgttcactg ttggccaggg    2880
caccaagctg gacatcaaac gcgcggccgc aattgaagtt atgtatcctc ctccttacct    2940
agacaatgag aagagcaatg gaaccattat ccatgtgaaa gggaaacacc tttgtccaag    3000 tccccctattt ccggacctt ctaagccctt ctgggtgctg gtggtggtcg gaggcgtgct    3060
ggcctgctac agcctgctgg tcaccgtggc cttcatcatc ttttgggtga ggagtaagag    3120
gagcaggctc ctgcacagtg actacatgaa catgactccc cgccgccccg ggcccacccg    3180
caagcattac cagccctatg ccccaccacg cgacttcgca gcctatcgct cccgggtgaa    3240
gttcagcaga agcgccgacg cccctgccta ccagcagggc cagaatcagc tgtacaacga    3300
gctgaacctg ggcagaaggg aagagtacga cgtcctggat aagcggagag ccgggaccc    3360 tgagatgggc ggcaagcctc ggcggaagaa ccccaggaa ggcctgtata cgaactgca    3420 gaaagacaag atggccgagg cctacagcga gatcggcatg aagggcgagc ggaggcgggg    3480
caagggccac gacggcctgt atcagggcct gtccaccgcc accaaggata cctacgacgc    3540
cctgcacatg caggccctgc cccaaggct cgagggcggc ggagagggca gaggaagtct    3600
tctaacatgc ggtgacgtgg aggagaatcc cggccctagg atgcttctcc tggtgacaag    3660
ccttctgctc tgtgagttac cacacccagc attcctcctg atcccacgca agtgtgtaa    3720 cggaataggt attggtgaat ttaaagactc actctccata aatgctacga atattaaaca    3780
cttcaaaaac tgcacctcca tcagtggcga tctcccacatc ctgccggtgg catttagggg    3840
tgactccttc acacatactc ctcctctgga tccacaggaa ctggatattc tgaaaaccgt    3900
aaaggaaatc acagggtttt tgctgattca ggcttggcct gaaaacagga cggacctcca    3960
tgcctttgag aacctagaaa tcatacgcgg caggaccaag caacatggtc agttttctct    4020
tgcagtcgtc agcctgaaca taacatcctt gggattacgc tccctcaagg agataagtga    4080
tggagatgtg ataatttcag gaaacaaaaa tttgtgctat gcaaatacaa taaactggaa    4140
aaaactgttt gggaccctccg gtcagaaaac caaaattata agcaacgagg tgaaaacag    4200 ctgcaaggcc acaggccagg tctgccatgc cttgtgctcc cccgagggct gctggggccc    4260 ggagccagg gactgcgtct cttgccggaa tgtcagccga ggcagggaat gcgtggacaa    4320
gtgcaacctt ctggagggtg agccaaggga gtttgtggag aactctgagt gcatacagtg    4380
ccacccagag tgcctgcctc aggccatgaa catcacctgc acaggacggg gaccagacaa    4440
ctgtatccag tgtgcccact acattgacgg ccccactgc gtcaagacct gcccggcagg    4500
agtcatggga gaaaacaaca ccctggtctg gaagtacgca gacgccggcc atgtgtgcca    4560
cctgtgccat ccaaactgca cctacggatg cactgggcca ggtcttgaag ctgtccaac    4620 gaatgggcct aagatcccgt ccatcgccac tgggatggtg ggggccctcc tcttgctgct    4680
ggtggtggcc ctggggatcg gcctcttcat gtgagcggcc gctctagacc cgggctgcag    4740
```

```
gaattcgata tcaagcttat cgataatcaa cctctggatt acaaaatttg tgaaagattg    4800
actggtattc ttaactatgt tgctccttt  acgctatgtg gatacgctgc tttaatgcct    4860
ttgtatcatg ctattgcttc ccgtatggct ttcattttct cctccttgta taaatcctgg    4920
ttgctgtctc tttatgagga gttgtggccc gttgtcaggc aacgtggcgt ggtgtgcact    4980
gtgtttgctg acgcaacccc cactggttgg ggcattgcca ccacctgtca gctccttttcc   5040 gggactttcg ctttcccccct ccctattgcc acggcggaac tcatcgccgc ctgccttgcc   5100
cgctgctgga caggggctcg gctgttgggc actgacaatt ccgtggtgtt gtcgggaaa     5160 tcatcgtcct ttccttggct gctcgcctgt gttgccacct ggattctgcg cgggacgtcc    5220
ttctgctacg tcccttcggc cctcaatcca gcggaccttc cttcccgcgg cctgctgccg    5280
gctctgcggc ctcttccgcg tcttcgcctt cgccctcaga cgagtcggat ctcccttgg    5340 gccgcctccc cgcatcgata ccgtcgacta gccgtacctt aagaccaat gacttacaag     5400 gcagctgtag atcttagcca cttttaaaa gaaaagggg gactgaagg gctaattcac       5460 tcccaaagaa gacaagatct gctttttgcc tgtactgggt ctctctggtt agaccagatc    5520
tgagcctggg agctctctgg ctaactaggg aacccactgc ttaagcctca ataaagcttg    5580
ccttgagtgc ttcaagtagt gtgtgcccgt ctgttgtgtg actctggtaa ctagagatcc    5640
ctcagaccct tttagtcagt gtggaaaatc tctagcagaa ttcgatatca agcttatcga    5700
taccgtcgac ctcgaggggg ggcccggtac ccaattcgcc ctatagtgag tcgtattaca    5760
attcactggc cgtcgtttta caacgtcgtg actgggaaaa ccctggcgtt acccaactta    5820
atcgccttgc agcacatccc cctttcgcca gctggcgtaa tagcgaagag gcccgcaccg    5880 atcgccttc caacagttg cgcagcctga atggcgaatg gaaattgtaa gcgttaatat      5940
tttgttaaaa ttcgcgttaa attttgtta aatcagctca ttttttaacc aataggccga    6000
aatcggcaaa atcccttata atcaaaaga atagaccgag atagggttga gtgttgttcc    6060
agtttggaac aagagtccac tattaaagaa cgtggactcc aacgtcaaag ggcgaaaaac    6120
cgtctatcag ggcgatggcc cactacgtga accatcaccc taatcaagtt ttttggggtc    6180
gaggtgccgt aaagcactaa atcggaaccc taaagggagc ccccgattta gagcttgacg    6240
gggaaagccg gcgaacgtgg cgagaaagga agggaagaaa gcgaaaggag cgggcgctag    6300
ggcgctggca agtgtagcgg tcacgctgcg cgtaaccacc acaccccgccg cgcttaatgc    6360 gccgctacag ggcgcgtcag gtggcacttt tcggggaaat gtgcgcggaa cccctatttg    6420
tttatttttc taaatacatt caaatatgta tccgctcatg agacaataac cctgataaat    6480
gcttcaataa tattgaaaaa ggaagagtat gagtattcaa catttccgtg tcgcccttat    6540 tcccttttt  gcggcatttt gccttcctgt ttttgctcac ccagaaacgc tggtgaaagt    6600
aaaagatgct gaagatcagt tgggtgcacg agtgggttac atcgaactgg atctcaacag    6660
cggtaagatc cttgagagtt ttcgccccga agaacgtttt ccaatgatga gcacttttaa    6720
agttctgcta tgtggcgcgg tattatcccg tattgacgcc gggcaagagc aactcggtcg    6780
ccgcatacac tattctcaga atgacttggt tgagtactca ccagtcacag aaaagcatct    6840 tacgatggc atgacagtaa gagaattatg cagtgctgcc ataaccatga gtgataacac    6900
tgcggccaac ttacttctga caacgatcgg aggaccgaag gagctaaccg ctttttttgca   6960 caacatgggg gatcatgtaa ctcgccttga tcgttgggaa ccggagctga atgaagccat    7020
accaaacgac gagcgtgaca ccacgatgcc tgtagcaatg gcaacaacgt tgcgcaaact    7080
```

```
attaactggc gaactactta ctctagcttc ccggcaacaa ttaatagact ggatggaggc    7140
ggataaagtt gcaggaccac ttctgcgctc ggcccttccg gctggctggt ttattgctga    7200
taaatctgga gccggtgagc gtgggtctcg cggtatcatt gcagcactgg ggccagatgg    7260
taagccctcc cgtatcgtag ttatctacac gacggggagt caggcaacta tggatgaacg    7320
aaatagacag atcgctgaga taggtgcctc actgattaag cattggtaac tgtcagacca    7380
agtttactca tatatacttt agattgattt aaaacttcat ttttaattta aaaggatcta    7440
ggtgaagatc cttttttgata atctcatgac caaaatccct taacgtgagt tttcgttcca    7500
ctgagcgtca gacccgtag aaaagatcaa aggatcttct tgagatcctt ttttttctgcg    7560
cgtaatctgc tgcttgcaaa caaaaaaacc accgctacca gcggtggttt gtttgccgga    7620
tcaagagcta ccaactcttt ttccgaaggt aactggcttc agcagagcgc agataccaaa    7680
tactgttctt ctagtgtagc cgtagttagg ccaccacttc aagaactctg tagcaccgcc    7740
tacatacctc gctctgctaa tcctgttacc agtggctgct gccagtggcg ataagtcgtg    7800
tcttaccggg ttggactcaa gacgatagtt accggataag gcgcagcggt cgggctgaac    7860
ggggggttcg tgcacacagc ccagcttgga gcgaacgacc tacaccgaac tgagatacct    7920
acagcgtgag ctatgagaaa gcgccacgct cccgaaggg agaaaggcgg acaggtatcc    7980
ggtaagcggc agggtcggaa caggagagcg cacgagggag cttccagggg gaaacgcctg    8040
gtatctttat agtcctgtcg ggtttcgcca cctctgactt gagcgtcgat ttttgtgatg    8100
ctcgtcaggg gggcggagcc tatggaaaaa cgccagcaac gcggcctttt tacggttcct    8160
ggccttttgc tggccttttg ctcacatgtt ctttcctgcg ttatcccctg attctgtgga    8220
taaccgtatt accgcctttg agtgagctga taccgctcgc cgcagccgaa cgaccgagcg    8280
cagcgagtca gtgagcgagg aagcggaaga gcgcccaata cgcaaaccgc ctctccccgc    8340
gcgttggccg attcattaat gcagctggca cgacaggttt cccgactgga aagcgggcag    8400
tgagcgcaac gcaattaatg tgagttagct cactcattag gcaccccagg ctttacactt    8460
tatgcttccg gctcgtatgt tgtgtggaat tgtgagcgga taacaatttc acacaggaaa    8520
cagctatgac catgattacg ccaagctcga aattaaccct cactaaaggg aacaaaagct    8580
ggagctccac cgcggtggcg gcctcgaggt cgagatccgg tcgaccagca accatagtcc    8640
cgccctaac tccgcccatc ccgccctaa ctccgcccag ttccgcccat tctccgcccc    8700
atggctgact aattttttttt atttatgcag aggccgaggc cgcctcggcc tctgagctat    8760
tccagaagta gtgaggaggc ttttttggag gcctaggctt ttgcaaaaag cttcgacggt    8820
atcgattggc tcatgtccaa cattaccgcc atgttgacat tgattattga ctagttatta    8880
atagtaatca attacgggt cattagttca tagcccatat atggagttcc gcgttacata    8940
acttacggta aatggcccgc ctggctgacc gcccaacgac ccccgcccat tgacgtcaat    9000
aatgacgtat gttcccatag taacgccaat agggactttc cattgacgtc aatgggtgga    9060
gtatttacgg taaactgccc acttggcagt acatcaagtg tatcatatgc caagtacgcc    9120
ccctattgac gtcaatgacg gtaaatggcc cgcctggcat tatgcccagt acatgacctt    9180
atgggacttt cctacttggc agtacatcta cgtattagtc atcgctatta ccatggtgat    9240
gcggttttgg cagtacatca atgggcgtgg atagcggttt gactcacggg gatttccaag    9300
tctccacccc attgacgtca atgggagttt gttttggcac caaaatcaac gggactttcc    9360
aaaatgtcgt aacaactccg ccccattgac gcaaatgggc ggtaggcgtg tacggaattc    9420
ggagtggcga gccctcagat cctgcatata agcagctgct ttttgcctgt actgggtctc    9480
``` tctg                                                                 9484

<210> SEQ ID NO 2
<211> LENGTH: 9487
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
gttagaccag atctgagcct gggagctctc tggctaacta gggaacccac tgcttaagcc      60
tcaataaagc ttgccttgag tgcttcaagt agtgtgtgcc cgtctgttgt gtgactctgg     120
taactagaga tccctcagac ccttttagtc agtgtggaaa atctctagca gtggcgcccg     180
aacagggact tgaaagcgaa agggaaacca gaggagctct ctcgacgcag gactcggctt     240
gctgaagcgc gcacggcaag aggcgagggg cggcgactgg tgagtacgcc aaaaattttg     300
actagcggag gctagaagga gagagatggg tgcgagagcg tcagtattaa gcgggggaga     360
attagatcga tgggaaaaaa ttcggttaag gccaggggga aagaaaaaat ataaattaaa     420
acatatagta tgggcaagca gggagctaga acgattcgca gttaatcctg gcctgttaga     480
aacatcagaa ggctgtagac aaatactggg acagctacaa ccatcccttc agacaggatc     540
agaagaactt agatcattat ataatacagt agcaaccctc tattgtgtgc atcaaaggat     600
agagataaaa gacaccaagg aagctttaga caagatagag gaagagcaaa acaaaagtaa     660
gaaaaaagca cagcaagcag cagctgacac aggacacagc aatcaggtca gccaaaatta     720
ccctatagtg cagaacatcc aggggcaaat ggtacatcag gccatatcac ctagaacttt     780
aaatgcatgg gtaaaagtag tagaagagaa ggctttcagc ccagaagtga tacccatgtt     840
ttcagcatta tcagaaggag ccaccccaca agatttaaac accatgctaa acacagtggg     900
gggacatcaa gcagccatgc aaatgttaaa agagaccatc aatgaggaag ctgcaggcaa     960
agagaagagt ggtgcagaga aaaaaagag cagtgggaat aggagctttg ttccttgggt    1020
tcttgggagc agcaggaagc actatgggcg cagcgtcaat gacgctgacg gtacaggcca    1080
gacaattatt gtctggtata gtgcagcagc agaacaattt gctgagggct attgaggcgc    1140
aacagcatct gttgcaactc acagtctggg gcatcaagca gctccaggca agaatcctgg    1200
ctgtggaaag atacctaaag gatcaacagc tcctggggat ttggggttgc tctggaaaac    1260
tcatttgcac cactgctgtg ccttggatct acaaatggca gtattcatcc acaattttaa    1320
aagaaaaggg gggattgggg ggtacagtgc aggggaaaga atagtagaca taatagcaac    1380
agacatacaa actaaagaat tacaaaaaca aattacaaaa attcaaaatt tcgggttta    1440 ttacagggac agcagagatc cagtttgggg atcaattgca tgaagaatct gcttagggtt    1500
aggcgttttg cgctgcttcg cgaggatctg cgatcgctcc ggtgcccgtc agtgggcaga    1560
gcgcacatcg cccacagtcc ccgagaagtt ggggggaggg gtcggcaatt gaaccggtgc    1620
ctagagaagg tggcgcgggg taaactggga aagtgatgtc gtgtactggc tccgcctttt    1680
tcccgagggt gggggagaac cgtatataag tgcagtagtc gccgtgaacg ttctttttcg    1740
caacgggttt gccgccagaa cacagctgaa gcttcgaggg gctcgcatct ctccttcacg    1800
cgcccgccgc cctacctgag gccgccatcc acgccggttg agtcgcgttc tgccgcctcc    1860
cgcctgtggt gcctcctgaa ctgcgtccgc cgtctaggta agtttaaagc tcaggtcgag    1920
accgggcctt tgtccggcgc tcccttggag cctacctaga ctcagccggc tctccacgct    1980

```
ttgcctgacc ctgcttgctc aactctacgt ctttgtttcg ttttctgttc tgcgccgtta   2040
cagatccaag ctgtgaccgg cgcctacggc tagcgccgcc accatgctgc tgctggtgac   2100
cagcctgctg ctgtgcgagc tgccccaccc cgcctttctg ctgatccccg aggtgaaact   2160
aatagaatct gggggaggct tggttgagcc agggcggtct ctgagactcg cgtgtacaac   2220
gtctggattc acctttgccg actacggttt gtcctggttc cgccagggtc ccggcaaggg   2280
ccttgaatgg gtaggtttca ctggaccgaa acacctcggt gagacaacag aatgcgcccc   2340
gtctgtggaa gacagatgca ccatctcaag agatgattcc aaaagcaccg tctatctgca   2400
gatgcacagg ctccaacacg aagacacagc cgtgtacttc tgtgttggac cttggttcgg   2460
cgacttatta atgtggggcc agggaaccct ggtcaccgtc tcctcagcta gctccggagg   2520
ctcaacttct ggctccggta agccaggcag cggagaaggt agtagtggat ccgcgcgcgc   2580
catccagatg acccagtctc catcctccct gtctgcatct gttggagaca gagtctccat   2640
cacttgccgg gcaactcagg acatcagcac atctttaggc tggtatcacc agagacccgg   2700
gaaagccccg aggctcctga tctatggtgc ttcgaaggta caaactgggg tcccatcacg   2760
attcagcggc aatgggtctg gcacagagtt cactctcacc atcagcagcc tgcagcctga   2820
agatataggg acttattatt gtctacaaga tgatggtttc ccgttcactg ttggccaggg   2880
caccaagctg gacatcaaac gcgcggccgc aattgaagtt atgtatcctc ctccttacct   2940
agacaatgag aagagcaatg gaaccattat ccatgtgaaa gggaaacacc tttgtccaag   3000 tccectattt cccggacctt ctaagcccttt ctgggtgctg gtggtggtcg gaggcgtgct   3060
ggcctgctac agcctgctgg tcaccgtggc cttcatcatc ttttgggtga acggggcag   3120 aaagaaactc ctgtatatat tcaaacaacc atttatgaga ccagtacaaa ctactcaaga   3180
ggaagatggc tgtagctgcc gatttccaga agaagaagaa ggaggatgtg aactgcgggt   3240
gaagttcagc agaagcgccg acgccctgc ctaccagcag gccagaatc agctgtacaa   3300 cgagctgaac ctgggcagaa gggaagagta cgacgtcctg ataagcgga gaggccggga   3360 ccctgagatg ggcggcaagc ctcggcggaa gaaccccag gaaggcctgt ataacgaact   3420
gcagaaagac aagatggccg aggcctacag cgagatcggc atgaagggcg agcggaggcg   3480
gggcaagggc cacgacggcc tgtatcaggg cctgtccacc gccaccaagg atacctacga   3540
cgccctgcac atgcaggccc tgccccaag gctcgagggc ggcggagagg cagaggaag   3600 tcttctaaca tgcggtgacg tggaggagaa tcccggccct aggatgcttc tcctggtgac   3660
aagccttctg ctctgtgagt taccacaccc agcattcctc ctgatcccac gcaaagtgtg   3720
taacggaata ggtattggtg aatttaaaga ctcactctcc ataaatgcta cgaatattaa   3780
acacttcaaa aactgcacct ccatcagtgg cgatctccac atcctgccgg tgcatttag   3840 gggtgactcc ttcacacata tcctcctct ggatccacag gaactggata ttctgaaaac   3900
cgtaaaggaa atcacagggt ttttgctgat tcaggcttgg cctgaaaaca ggacggacct   3960
ccatgccttt gagaacctag aaatcatacg cggcaggacc aagcaacatg gtcagttttc   4020
tcttgcagtc gtcagcctga acataacatc cttgggatta gctccctca aggagataag   4080 tgatggagat gtgataattt caggaaacaa aatttgtgc tatgcaaata caataaactg   4140
gaaaaaactg tttgggaccct ccggtcagaa aaccaaaatt ataagcaaca gaggtgaaaa   4200
cagctgcaag gccacaggcc aggtctgcca tgccttgtgc tcccccgagg ctgctgggg   4260 cccggagccc agggactgcg tctcttgccg gaatgtcagc cgaggcaggg aatgcgtgga   4320
```

```
caagtgcaac cttctggagg gtgagccaag ggagtttgtg gagaactctg agtgcataca    4380
gtgccaccca gagtgcctgc ctcaggccat gaacatcacc tgcacaggac ggggaccaga    4440
caactgtatc cagtgtgccc actacattga cggcccccac tgcgtcaaga cctgcccggc    4500
aggagtcatg ggagaaaaca acaccctggt ctggaagtac gcagacgccg gccatgtgtg    4560
ccacctgtgc catccaaact gcacctacgg atgcactggg ccaggtcttg aaggctgtcc    4620
aacgaatggg cctaagatcc cgtccatcgc cactgggatg gtgggggccc tcctcttgct    4680
gctggtggtg gccctgggga tcggcctctt catgtgagcg gccgctctag acccgggctg    4740
caggaattcg atatcaagct tatcgataat caacctctgg attacaaaat tgtgaaagat    4800
tgactggta ttcttaacta tgttgctcct tttacgctat gtggatacgc tgctttaatg     4860
cctttgtatc atgctattgc ttcccgtatg gctttcattt tctcctcctt gtataaatcc    4920
tggttgctgt ctctttatga ggagttgtgg cccgttgtca ggcaacgtgg cgtggtgtgc    4980
actgtgtttg ctgacgcaac ccccactggt tggggcattg ccaccacctg tcagctcctt    5040
tccgggactt tcgctttccc cctccctatt gccacggcgg aactcatcgc cgcctgcctt    5100
gcccgctgct ggacaggggc tcggctgttg ggcactgaca attccgtggt gttgtcgggg    5160
aaatcatcgt ccttccttg gctgctcgcc tgtgttgcca cctggattct gcgcgggacg    5220
tccttctgct acgtcccttc ggccctcaat ccagcggacc ttccttcccg cggcctgctg    5280
ccggctctgc ggcctcttcc gcgtcttcgc cttcgccctc agacgagtcg gatctccctt    5340
tgggccgcct ccccgcatcg ataccgtcga ctagccgtac ctttaagacc aatgacttac    5400
aaggcagctg tagatcttag ccactttta aaagaaaagg ggggactgga agggctaatt     5460
cactcccaaa gaagacaaga tctgcttttt gcctgtactg ggtctctctg gttagaccag    5520
atctgagcct gggagctctc tggctaacta gggaacccac tgcttaagcc tcaataaagc    5580
ttgccttgag tgcttcaagt agtgtgtgcc cgtctgttgt gtgactctgg taactagaga    5640
tccctcagac ccttttagtc agtgtggaaa atctctagca gaattcgata tcaagcttat    5700
cgataccgtc gacctcgagg gggggcccgg tacccaattc gccctatagt gagtcgtatt    5760
acaattcact ggccgtcgtt ttacaacgtc gtgactggga aaaccctggc gttacccaac    5820
ttaatcgcct tgcagcacat ccccctttcg ccagctggcg taatagcgaa gaggcccgca    5880
ccgatcgccc ttcccaacag ttgcgcagcc tgaatggcga atggaaattg taagcgttaa    5940
tattttgtta aaattcgcgt taaatttttg ttaaatcagc tcatttttta accaataggc    6000
cgaaatcggc aaaatccctt ataaatcaaa agaatagacc gagatagggt tgagtgttgt    6060
tccagtttgg aacaagagtc cactattaaa gaacgtggac tccaacgtca agggcgaaa    6120
aaccgtctat cagggcgatg gcccactacg tgaaccatca ccctaatcaa gttttttggg    6180
gtcgaggtgc cgtaaagcac taaatcggaa ccctaaaggg agcccccgat ttagagcttg    6240
acggggaaag ccggcgaacg tggcgagaaa ggaagggaag aaagcgaaag gagcgggcgc    6300
tagggcgctg gcaagtgtag cggtcacgct gcgcgtaacc accacacccg ccgcgcttaa    6360
tgcgccgcta cagggcgcgt caggtggcac ttttcgggga aatgtgcgcg gaacccctat    6420
ttgtttattt ttctaaatac attcaaatat gtatccgctc atgagacaat aaccctgata    6480
aatgcttcaa taatattgaa aaaggaagag tatgagtatt caacatttcc gtgtcgccct    6540
tattcccttt tttgcggcat tttgccttcc tgttttttgct cacccagaaa cgctggtgaa    6600
agtaaaagat gctgaagatc agttgggtgc acgagtgggt tacatcgaac tggatctcaa    6660
cagcggtaag atccttgaga gttttcgccc cgaagaacgt tttccaatga tgagcacttt    6720
```

```
taaagttctg ctatgtggcg cggtattatc ccgtattgac gccgggcaag agcaactcgg    6780
tcgccgcata cactattctc agaatgactt ggttgagtac tcaccagtca cagaaaagca    6840
tcttacggat ggcatgacag taagagaatt atgcagtgct gccataacca tgagtgataa    6900
cactgcggcc aacttacttc tgacaacgat cggaggaccg aaggagctaa ccgcttttt    6960 gcacaacatg ggggatcatg taactcgcct tgatcgttgg gaaccggagc tgaatgaagc    7020
cataccaaac gacgagcgtg acaccacgat gcctgtagca atggcaacaa cgttgcgcaa    7080
actattaact ggcgaactac ttactctagc ttcccggcaa caattaatag actggatgga    7140
ggcggataaa gttgcaggac cacttctgcg ctcggccctt ccggctggct ggtttattgc    7200
tgataaatct ggagccggtg agcgtgggtc tcgcggtatc attgcagcac tggggccaga    7260
tggtaagccc tcccgtatcg tagttatcta cacgacgggg agtcaggcaa ctatggatga    7320
acgaaataga cagatcgctg agataggtgc ctcactgatt aagcattggt aactgtcaga    7380
ccaagtttac tcatatatac tttagattga tttaaaactt catttttaat ttaaaaggat    7440
ctaggtgaag atcctttttg ataatctcat gaccaaaatc ccttaacgtg agttttcgtt    7500
ccactgagcg tcagaccccg tagaaaagat caaaggatct tcttgagatc ctttttttct    7560
gcgcgtaatc tgctgcttgc aaacaaaaaa accaccgcta ccagcggtgg tttgtttgcc    7620
ggatcaagag ctaccaactc tttttccgaa ggtaactggc ttcagcagag cgcagatacc    7680
aaatactgtt cttctagtgt agccgtagtt aggccaccac ttcaagaact ctgtagcacc    7740
gcctacatac ctcgctctgc taatcctgtt accagtggct gctgccagtg gcgataagtc    7800
gtgtcttacc gggttggact caagacgata gttaccggat aaggcgcagc ggtcgggctg    7860
aacggggggt tcgtgcacac agcccagctt ggagcgaacg acctacaccg aactgagata    7920
cctacagcgt gagctatgag aaagcgccac gcttcccgaa gggagaaagg cggacaggta    7980
tccggtaagc ggcagggtcg gaacaggaga gcgcacgagg gagcttccag ggggaaacgc    8040
ctggtatctt tatagtcctg tcgggtttcg ccacctctga cttgagcgtc gatttttgtg    8100
atgctcgtca ggggggcgga gcctatggaa aaacgccagc aacgcggcct ttttacggtt    8160
cctggccttt tgctggcctt tgctcacat gttctttcct gcgttatccc ctgattctgt    8220
ggataaccgt attaccgcct ttgagtgagc tgataccgct cgccgcagcc gaacgaccga    8280
gcgcagcgag tcagtgagcg aggaagcgga agagcgccca tacgcaaac cgcctctccc    8340 cgcgcgttgg ccgattcatt aatgcagctg gcacgacagg tttcccgact ggaaagcggg    8400
cagtgagcgc aacgcaatta atgtgagtta gctcactcat taggcacccc aggctttaca    8460
ctttatgctt ccggctcgta tgttgtgtgg aattgtgagc ggataacaat ttcacacagg    8520
aaacagctat gaccatgatt acgccaagct cgaaattaac cctcactaaa gggaacaaaa    8580
gctggagctc caccgcggtg gcggcctcga ggtcgagatc cggtcgacca gcaaccatag    8640
tcccgcccct aactccgccc atcccgcccc taactccgcc cagttccgcc cattctccgc    8700
cccatggctg actaatttt tttatttatg cagaggccga ggccgcctcg gcctctgagc    8760
tattccagaa gtagtgagga ggctttttg gaggcctagg cttttgcaaa aagcttcgac    8820
ggtatcgatt ggctcatgtc caacattacc gccatgttga cattgattat tgactagtta    8880
ttaatagtaa tcaattacgg ggtcattagt tcatagccca tatatggagt tccgcgttac    8940
ataacttacg gtaaatggcc cgcctggctg accgcccaac gacccccgcc cattgacgtc    9000
aataatgacg tatgttccca tagtaacgcc aatagggact ttccattgac gtcaatgggt    9060
```

```
ggagtattta cggtaaactg cccacttggc agtacatcaa gtgtatcata tgccaagtac    9120
gcccccuatt gacgtcaatg acggtaaatg ccccgcctgg cattatgccc agtacatgac    9180
cttatgggac tttcctactt ggcagtacat ctacgtatta gtcatcgcta ttaccatggt    9240
gatgcggttt tggcagtaca tcaatgggcg tggatagcgg tttgactcac ggggatttcc    9300
aagtctccac cccattgacg tcaatgggag tttgttttgg caccaaaatc aacgggactt    9360
tccaaaatgt cgtaacaact ccgccccatt gacgcaaatg gcggtaggc gtgtacggaa      9420 ttcggagtgg cgagccctca gatcctgcat ataagcagct gcttttgcc tgtactgggt    9480 ctctctg                                                              9487
```

<210> SEQ ID NO 3
<211> LENGTH: 16
<212> TYPE: PRT
<213> ORGANISM: Homo sapiens

<400> SEQUENCE: 3

Val Tyr Ala Thr Arg Ser Ser Ala Val Arg Leu Arg Ser Ser Val Pro
1               5                   10                  15

<210> SEQ ID NO 4
<211> LENGTH: 16
<212> TYPE: PRT
<213> ORGANISM: Mus sp.

<400> SEQUENCE: 4

Ala Tyr Val Thr Arg Ser Ser Ala Val Arg Leu Arg Ser Ser Val Pro
1               5                   10                  15

<210> SEQ ID NO 5
<211> LENGTH: 1419
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

```
gaggtgaaac taatagaatc tgggggaggc ttggttgagc cagggcggtc tctgagactc      60
gcgtgtacaa cgtctggatt cacctttgcc gactacggtt tgtcctggtt ccgccagggt     120
cccggcaagg gccttgaatg ggtaggtttc actggaccga acacctcgg tgagacaaca      180 gaatgcgccc cgtctgtgga agacagatgc accatctcaa gagatgattc caaaagcacc    240
gtctatctgc agatgcacag gctccaacac gaagacacag ccgtgtactt ctgtgttgga    300
ccttggttcg gcgacttatt aatgtggggc cagggaaccc tggtcaccgt ctcctcagct    360
agctccggag gctcaacttc tggctccggt aagccaggca gcgagaagg tagtagtgga     420 tccgcgcgcg ccatccagat gacccagtct ccatcctccc tgtctgcatc tgttggagac    480
agagtctcca tcacttgccg ggcaactcag gacatcagca catctttagg ctggtatcac    540
cagagacccg ggaaagcccc gaggctcctg atctatggtg cttcgaaggt acaaactggg    600
gtcccatcac gattcagcgg caatgggtct ggcacagagt tcactctcac catcagcagc    660
ctgcagcctg aagatatagg gacttattat tgtctacaag atgatggttt cccgttcact    720
gttggccagg gcaccaagct ggacatcaaa cgcgcggccg caattgaagt tatgtatcct    780
cctccttacc tagacaatga gaagagcaat ggaaccatta ccatgtgaa agggaaacac     840 ctttgtccaa gtcccctatt tcccggacct tctaagccct ctgggtgct ggtggtggtc     900
```

```
ggaggcgtgc tggcctgcta cagcctgctg gtcaccgtgg ccttcatcat cttttgggtg      960
aggagtaaga ggagcaggct cctgcacagt gactacatga acatgactcc ccgccgcccc     1020
gggcccaccc gcaagcatta ccagccctat gccccaccac gcgacttcgc agcctatcgc     1080
tcccgggtga agttcagcag aagcgccgac gcccctgcct accagcaggg ccagaatcag     1140
ctgtacaacg agctgaacct gggcagaagg gaagagtacg acgtcctgga taagcggaga     1200
ggccgggacc ctgagatggg cggcaagcct cggcggaaga accccagga aggcctgtat     1260 aacgaactgc agaaagacaa gatggccgag gcctacagcg agatcggcat gaagggcgag     1320
cggaggcggg gcaagggcca cgacggcctg tatcagggcc tgtccaccgc caccaaggat     1380
acctacgacg ccctgcacat gcaggccctg cccccaagg                            1419
```

<210> SEQ ID NO 6
<211> LENGTH: 1422
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

```
gaggtgaaac taatagaatc tggggaggc ttggttgagc cagggcggtc tctgagactc       60
gcgtgtacaa cgtctggatt cacctttgcc gactacggtt tgtcctggtt ccgccagggt      120
cccggcaagg gccttgaatg ggtaggtttc actggaccga acacctcggt gagacaaca      180 gaatgcgccc cgtctgtgga agacagatgc accatctcaa gagatgattc caaaagcacc     240
gtctatctgc agatgcacag gctccaacac gaagacacag ccgtgtactt ctgtgttgga     300
ccttggttcg gcgacttatt aatgtggggc cagggaaccc tggtcaccgt ctcctcagct     360
agctccggag gctcaacttc tggctccggt aagccaggca gcggagaagg tagtagtgga     420
tccgcgcgcg ccatccagat gacccagtct ccatcctccc tgtctgcatc tgttggagac     480
agagtctcca tcacttgccg ggcaactcag gacatcagca catctttagg ctggtatcac     540
cagagacccg ggaaagcccc gaggctcctg atctatggtg cttcgaaggt acaaactggg     600
gtcccatcac gattcagcgg caatgggtct ggcacagagt tcactctcac catcagcagc     660
ctgcagcctg aagatatagg gacttattat tgtctacaag atgatggttt cccgttcact     720
gttggccagg gcaccaagct ggacatcaaa cgcgcggccg caattgaagt tatgtatcct     780
cctccttacc tagacaatga aagagcaat ggaaccatta tccatgtgaa agggaaacac     840 cttttgtccaa gtccctatt tcccggacct tctaagccct tctgggtgct ggtggtggtc     900
ggaggcgtgc tggcctgcta cagcctgctg gtcaccgtgg ccttcatcat cttttgggtg     960
aaacggggca gaaagaaact cctgtatata ttcaaacaac catttatgag accagtacaa    1020
actactcaag aggaagatgg ctgtagctgc cgatttccag aagaagaaga aggaggatgt    1080
gaactgcggg tgaagttcag cagaagcgcc gacgcccctg cctaccagca gggccagaat    1140
cagctgtaca acgagctgaa cctgggcaga agggaagagt acgacgtcct ggataagcgg    1200
agaggccggg accctgagat gggcggcaag cctcggcgga agaacccca ggaaggcctg    1260 tataacgaac tgcagaaaga caagatggcc gaggcctaca gcgagatcgg catgaagggc    1320
gagcggaggc ggggcaaggg ccacgacggc ctgtatcagg gcctgtccac cgccaccaag    1380
gatacctacg acgccctgca catgcaggcc ctgccccaa gg                        1422
```

<210> SEQ ID NO 7

<211> LENGTH: 762
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 7

```
gaggtgaaac taatagaatc tgggggaggc ttggttgagc cagggcggtc tctgagactc      60
gcgtgtacaa cgtctggatt caccttttgcc gactacggtt tgtcctggtt ccgccagggt    120
cccggcaagg gccttgaatg gtaggtttc actggaccga acacctcgg tgagacaaca       180
gaatgcgccc cgtctgtgga agacagatgc accatctcaa gagatgattc caaaagcacc    240
gtctatctgc agatgcacag gctccaacac gaagacacag ccgtgtactt ctgtgttgga    300
ccttggttcg gcgacttatt aatgtgggc caggaaccc tggtcaccgt ctcctcagct      360
agctccggag gctcaacttc tggctccggt aagccaggca gcggagaagg tagtagtgga    420
tccgcgcgcg ccatccagat gacccagtct ccatcctccc tgtctgcatc tgttggagac    480
agagtctcca tcacttgccg ggcaactcag gacatcagca catctttagg ctggtatcac    540
cagagacccg ggaaagcccc gaggctcctg atctatggtg cttcgaaggt acaaactggg    600
gtcccatcac gattcagcgg caatgggtct ggcacagagt tcactctcac catcagcagc    660
ctgcagcctg aagatatagg gacttattat tgtctacaag atgatggttt cccgttcact    720
gttggccagg gcaccaagct ggacatcaaa cgcgcggccg ca                        762
```

<210> SEQ ID NO 8
<211> LENGTH: 117
<212> TYPE: DNA
<213> ORGANISM: Homo sapiens

<400> SEQUENCE: 8

```
attgaagtta tgtatcctcc tccttaccta gacaatgaga agagcaatgg aaccattatc     60
catgtgaaag ggaaacacct ttgtccaagt cccctatttc ccggaccttc taagccc       117
```

<210> SEQ ID NO 9
<211> LENGTH: 81
<212> TYPE: DNA
<213> ORGANISM: Homo sapiens

<400> SEQUENCE: 9

```
ttctgggtgc tggtggtggt cggaggcgtg ctggcctgct acagcctgct ggtcaccgtg     60
gccttcatca tcttttgggt g                                               81
```

<210> SEQ ID NO 10
<211> LENGTH: 336
<212> TYPE: DNA
<213> ORGANISM: Homo sapiens

<400> SEQUENCE: 10

```
cgggtgaagt tcagcagaag cgccgacgcc cctgcctacc agcagggcca gaatcagctg     60
tacaacgagc tgaacctggg cagaagggaa gagtacgacg tcctggataa gcggagaggc    120
cgggaccctg agatgggcgg caagcctcgg cggaagaacc cccaggaagg cctgtataac    180
gaactgcaga agacaagat ggccgaggcc tacagcgaga tcggcatgaa gggcgagcgg    240
aggcggggca aggccacga cggcctgtat cagggcctgt ccaccgccac caaggatacc    300
tacgacgccc tgcacatgca ggccctgccc ccaagg                              336
```

-continued

<210> SEQ ID NO 11
<211> LENGTH: 123
<212> TYPE: DNA
<213> ORGANISM: Homo sapiens

<400> SEQUENCE: 11
aggagtaaga ggagcaggct cctgcacagt gactacatga acatgactcc ccgccgcccc      60
gggcccaccc gcaagcatta ccagccctat gccccaccac gcgacttcgc agcctatcgc     120
tcc                                                                   123

<210> SEQ ID NO 12
<211> LENGTH: 126
<212> TYPE: DNA
<213> ORGANISM: Homo sapiens

<400> SEQUENCE: 12
aaacggggca gaaagaaact cctgtatata ttcaaacaac catttatgag accagtacaa      60
actactcaag aggaagatgg ctgtagctgc cgatttccag aagaagaaga aggaggatgt     120
gaactg                                                                126

<210> SEQ ID NO 13
<211> LENGTH: 473
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Glu Val Lys Leu Ile Glu Ser Gly Gly Gly Leu Val Glu Pro Gly Arg
1               5                   10                  15

Ser Leu Arg Leu Ala Cys Thr Thr Ser Gly Phe Thr Phe Ala Asp Tyr
            20                  25                  30

Gly Leu Ser Trp Phe Arg Gln Gly Pro Gly Lys Gly Leu Glu Trp Val
        35                  40                  45

Gly Phe Thr Gly Pro Lys His Leu Gly Glu Thr Thr Glu Cys Ala Pro
    50                  55                  60

Ser Val Glu Asp Arg Cys Thr Ile Ser Arg Asp Asp Ser Lys Ser Thr
65                  70                  75                  80

Val Tyr Leu Gln Met His Arg Leu Gln His Glu Asp Thr Ala Val Tyr
                85                  90                  95

Phe Cys Val Gly Pro Trp Phe Gly Asp Leu Leu Met Trp Gly Gln Gly
            100                 105                 110

Thr Leu Val Thr Val Ser Ser Ala Ser Ser Gly Gly Ser Thr Ser Gly
        115                 120                 125

Ser Gly Lys Pro Gly Ser Gly Glu Gly Ser Ser Gly Ser Ala Arg Ala
    130                 135                 140

Ile Gln Met Thr Gln Ser Pro Ser Ser Leu Ser Ala Ser Val Gly Asp
145                 150                 155                 160

Arg Val Ser Ile Thr Cys Arg Ala Thr Gln Asp Ile Ser Thr Ser Leu
                165                 170                 175

Gly Trp Tyr His Gln Arg Pro Gly Lys Ala Pro Arg Leu Leu Ile Tyr
            180                 185                 190

Gly Ala Ser Lys Val Gln Thr Gly Val Pro Ser Arg Phe Ser Gly Asn
        195                 200                 205

Gly Ser Gly Thr Glu Phe Thr Leu Thr Ile Ser Ser Leu Gln Pro Glu

```
                    210                 215                 220
Asp Ile Gly Thr Tyr Tyr Cys Leu Gln Asp Asp Gly Phe Pro Phe Thr
225                 230                 235                 240

Val Gly Gln Gly Thr Lys Leu Asp Ile Lys Arg Ala Ala Ala Ile Glu
                    245                 250                 255

Val Met Tyr Pro Pro Tyr Leu Asp Asn Glu Lys Ser Asn Gly Thr
                260                 265                 270

Ile Ile His Val Lys Gly Lys His Leu Cys Pro Ser Pro Leu Phe Pro
                275                 280                 285

Gly Pro Ser Lys Pro Phe Trp Val Leu Val Val Val Gly Gly Val Leu
            290                 295                 300

Ala Cys Tyr Ser Leu Leu Val Thr Val Ala Phe Ile Ile Phe Trp Val
305                 310                 315                 320

Arg Ser Lys Arg Ser Arg Leu Leu His Ser Asp Tyr Met Asn Met Thr
                    325                 330                 335

Pro Arg Arg Pro Gly Pro Thr Arg Lys His Tyr Gln Pro Tyr Ala Pro
                340                 345                 350

Pro Arg Asp Phe Ala Ala Tyr Arg Ser Arg Val Lys Phe Ser Arg Ser
            355                 360                 365

Ala Asp Ala Pro Ala Tyr Gln Gln Gly Gln Asn Gln Leu Tyr Asn Glu
                370                 375                 380

Leu Asn Leu Gly Arg Arg Glu Glu Tyr Asp Val Leu Asp Lys Arg Arg
385                 390                 395                 400

Gly Arg Asp Pro Glu Met Gly Gly Lys Pro Arg Arg Lys Asn Pro Gln
                    405                 410                 415

Glu Gly Leu Tyr Asn Glu Leu Gln Lys Asp Lys Met Ala Glu Ala Tyr
                420                 425                 430

Ser Glu Ile Gly Met Lys Gly Glu Arg Arg Arg Gly Lys Gly His Asp
            435                 440                 445

Gly Leu Tyr Gln Gly Leu Ser Thr Ala Thr Lys Asp Thr Tyr Asp Ala
450                 455                 460

Leu His Met Gln Ala Leu Pro Pro Arg
465                 470

<210> SEQ ID NO 14
<211> LENGTH: 474
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Glu Val Lys Leu Ile Glu Ser Gly Gly Gly Leu Val Glu Pro Gly Arg
1               5                   10                  15

Ser Leu Arg Leu Ala Cys Thr Thr Ser Gly Phe Thr Phe Ala Asp Tyr
                20                  25                  30

Gly Leu Ser Trp Phe Arg Gln Gly Pro Gly Lys Gly Leu Glu Trp Val
            35                  40                  45

Gly Phe Thr Gly Pro Lys His Leu Gly Glu Thr Thr Glu Cys Ala Pro
        50                  55                  60

Ser Val Glu Asp Arg Cys Thr Ile Ser Arg Asp Asp Ser Lys Ser Thr
65                  70                  75                  80

Val Tyr Leu Gln Met His Arg Leu Gln His Glu Asp Thr Ala Val Tyr
                85                  90                  95
```

```
Phe Cys Val Gly Pro Trp Phe Gly Asp Leu Leu Met Trp Gly Gln Gly
                100                 105                 110

Thr Leu Val Thr Val Ser Ser Ala Ser Ser Gly Gly Ser Thr Ser Gly
            115                 120                 125

Ser Gly Lys Pro Gly Ser Gly Glu Gly Ser Ser Gly Ser Ala Arg Ala
        130                 135                 140

Ile Gln Met Thr Gln Ser Pro Ser Ser Leu Ser Ala Ser Val Gly Asp
145                 150                 155                 160

Arg Val Ser Ile Thr Cys Arg Ala Thr Gln Asp Ile Ser Thr Ser Leu
                165                 170                 175

Gly Trp Tyr His Gln Arg Pro Gly Lys Ala Pro Arg Leu Leu Ile Tyr
            180                 185                 190

Gly Ala Ser Lys Val Gln Thr Gly Val Pro Ser Arg Phe Ser Gly Asn
        195                 200                 205

Gly Ser Gly Thr Glu Phe Thr Leu Thr Ile Ser Ser Leu Gln Pro Glu
    210                 215                 220

Asp Ile Gly Thr Tyr Tyr Cys Leu Gln Asp Asp Gly Phe Pro Phe Thr
225                 230                 235                 240

Val Gly Gln Gly Thr Lys Leu Asp Ile Lys Arg Ala Ala Ile Glu
                245                 250                 255

Val Met Tyr Pro Pro Pro Tyr Leu Asp Asn Glu Lys Ser Asn Gly Thr
            260                 265                 270

Ile Ile His Val Lys Gly Lys His Leu Cys Pro Ser Pro Leu Phe Pro
        275                 280                 285

Gly Pro Ser Lys Pro Phe Trp Val Leu Val Val Val Gly Gly Val Leu
    290                 295                 300

Ala Cys Tyr Ser Leu Leu Val Thr Val Ala Phe Ile Ile Phe Trp Val
305                 310                 315                 320

Lys Arg Gly Arg Lys Lys Leu Leu Tyr Ile Phe Lys Gln Pro Phe Met
                325                 330                 335

Arg Pro Val Gln Thr Thr Gln Glu Glu Asp Gly Cys Ser Cys Arg Phe
            340                 345                 350

Pro Glu Glu Glu Glu Gly Gly Cys Glu Leu Arg Val Lys Phe Ser Arg
        355                 360                 365

Ser Ala Asp Ala Pro Ala Tyr Gln Gln Gly Gln Asn Gln Leu Tyr Asn
    370                 375                 380

Glu Leu Asn Leu Gly Arg Arg Glu Glu Tyr Asp Val Leu Asp Lys Arg
385                 390                 395                 400

Arg Gly Arg Asp Pro Glu Met Gly Gly Lys Pro Arg Arg Lys Asn Pro
                405                 410                 415

Gln Glu Gly Leu Tyr Asn Glu Leu Gln Lys Asp Lys Met Ala Glu Ala
            420                 425                 430

Tyr Ser Glu Ile Gly Met Lys Gly Glu Arg Arg Gly Lys Gly His
        435                 440                 445

Asp Gly Leu Tyr Gln Gly Leu Ser Thr Ala Thr Lys Asp Thr Tyr Asp
    450                 455                 460

Ala Leu His Met Gln Ala Leu Pro Pro Arg
465                 470
```

<210> SEQ ID NO 15
<211> LENGTH: 254
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 15

Glu Val Lys Leu Ile Glu Ser Gly Gly Gly Leu Val Glu Pro Gly Arg
1               5                   10                  15

Ser Leu Arg Leu Ala Cys Thr Thr Ser Gly Phe Thr Phe Ala Asp Tyr
            20                  25                  30

Gly Leu Ser Trp Phe Arg Gln Gly Pro Gly Lys Gly Leu Glu Trp Val
        35                  40                  45

Gly Phe Thr Gly Pro Lys His Leu Gly Glu Thr Thr Glu Cys Ala Pro
    50                  55                  60

Ser Val Glu Asp Arg Cys Thr Ile Ser Arg Asp Asp Ser Lys Ser Thr
65                  70                  75                  80

Val Tyr Leu Gln Met His Arg Leu Gln His Glu Asp Thr Ala Val Tyr
                85                  90                  95

Phe Cys Val Gly Pro Trp Phe Gly Asp Leu Leu Met Trp Gly Gln Gly
            100                 105                 110

Thr Leu Val Thr Val Ser Ser Ala Ser Ser Gly Ser Thr Ser Gly
        115                 120                 125

Ser Gly Lys Pro Gly Ser Gly Glu Gly Ser Ser Gly Ala Arg Ala
    130                 135                 140

Ile Gln Met Thr Gln Ser Pro Ser Ser Leu Ser Ala Ser Val Gly Asp
145                 150                 155                 160

Arg Val Ser Ile Thr Cys Arg Ala Thr Gln Asp Ile Ser Thr Ser Leu
                165                 170                 175

Gly Trp Tyr His Gln Arg Pro Gly Lys Ala Pro Arg Leu Leu Ile Tyr
            180                 185                 190

Gly Ala Ser Lys Val Gln Thr Gly Val Pro Ser Arg Phe Ser Gly Asn
        195                 200                 205

Gly Ser Gly Thr Glu Phe Thr Leu Thr Ile Ser Ser Leu Gln Pro Glu
    210                 215                 220

Asp Ile Gly Thr Tyr Tyr Cys Leu Gln Asp Asp Gly Phe Pro Phe Thr
225                 230                 235                 240

Val Gly Gln Gly Thr Lys Leu Asp Ile Lys Arg Ala Ala Ala
                245                 250

<210> SEQ ID NO 16
<211> LENGTH: 39
<212> TYPE: PRT
<213> ORGANISM: Homo sapiens

<400> SEQUENCE: 16

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro
        35

<210> SEQ ID NO 17
<211> LENGTH: 27
<212> TYPE: PRT
<213> ORGANISM: Homo sapiens

<400> SEQUENCE: 17

Phe Trp Val Leu Val Val Val Gly Gly Val Leu Ala Cys Tyr Ser Leu
1               5                   10                  15

```
Leu Val Thr Val Ala Phe Ile Ile Phe Trp Val
            20                  25

<210> SEQ ID NO 18
<211> LENGTH: 112
<212> TYPE: PRT
<213> ORGANISM: Homo sapiens

<400> SEQUENCE: 18

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 19
<211> LENGTH: 41
<212> TYPE: PRT
<213> ORGANISM: Homo sapiens

<400> SEQUENCE: 19

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 20
<211> LENGTH: 42
<212> TYPE: PRT
<213> ORGANISM: Homo sapiens

<400> SEQUENCE: 20

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 21
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Citrulline
```

```
<220> FEATURE:
<221> NAME/KEY: MOD_RES
<222> LOCATION: (10)..(10)
<223> OTHER INFORMATION: Citrulline
<220> FEATURE:
<221> NAME/KEY: MOD_RES
<222> LOCATION: (12)..(12)
<223> OTHER INFORMATION: Citrulline

<400> SEQUENCE: 21

Val Tyr Ala Thr Xaa Ser Ser Ala Val Xaa Leu Xaa Ser Ser Val Pro
1               5                   10                  15

<210> SEQ ID NO 22
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Citrulline
<220> FEATURE:
<221> NAME/KEY: MOD_RES
<222> LOCATION: (10)..(10)
<223> OTHER INFORMATION: Citrulline
<220> FEATURE:
<221> NAME/KEY: MOD_RES
<222> LOCATION: (12)..(12)
<223> OTHER INFORMATION: Citrulline

<400> SEQUENCE: 22

Ala Tyr Val Thr Xaa Ser Ser Ala Val Xaa Leu Xaa Ser Ser Val Pro
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Gly Gly Gly Ser Gly Gly Gly Gly Ser Gly Gly Gly Gly Ser
1               5                   10                  15
```